(12) United States Patent
Li et al.

(10) Patent No.: US 11,408,897 B2
(45) Date of Patent: Aug. 9, 2022

(54) MASS DEFECT-BASED MULTIPLEX DIMETHYL PYRIMIDINYL ORNITHINE (DIPYRO) TAGS FOR HIGH-THROUGHPUT QUANTITATIVE PROTEOMICS AND PEPTIDOMICS

(71) Applicant: Wisconsin Alumni Research Foundation, Madison, WI (US)

(72) Inventors: Lingjun Li, Madison, WI (US); Dustin Frost, Madison, WI (US); Amanda Buchberger Jones, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 649 days.

(21) Appl. No.: 15/768,299

(22) PCT Filed: Oct. 14, 2016

(86) PCT No.: PCT/US2016/057156
§ 371 (c)(1),
(2) Date: Apr. 13, 2018

(87) PCT Pub. No.: WO2017/066650
PCT Pub. Date: Apr. 20, 2017

(65) Prior Publication Data
US 2018/0299464 A1   Oct. 18, 2018

Related U.S. Application Data

(60) Provisional application No. 62/241,590, filed on Oct. 14, 2015.

(51) Int. Cl.
G01N 33/68 (2006.01)
C07D 239/42 (2006.01)

(52) U.S. Cl.
CPC ....... *G01N 33/6848* (2013.01); *C07D 239/42* (2013.01); *G01N 33/6812* (2013.01); *G01N 2458/15* (2013.01)

(58) Field of Classification Search
CPC ............. C07D 239/42; G01N 33/6812; G01N 33/6848; G01N 2458/15; C07K 1/13
See application file for complete search history.

(56) References Cited

U.S. PATENT DOCUMENTS

2006/0172319 A1   8/2006 Yan et al.
2008/0242838 A1  10/2008 Peters et al.
(Continued)

FOREIGN PATENT DOCUMENTS

JP   2005-514404   5/2005
JP   2009-503485   1/2009
JP   2009-526998   7/2009

OTHER PUBLICATIONS

European Office Action, dated Feb. 6, 2020, corresponding to European Application No. 16856326.0, 4 pp.
(Continued)

*Primary Examiner* — Jennifer Wecker
*Assistant Examiner* — Michelle Adams
(74) *Attorney, Agent, or Firm* — Leydig, Voit & Mayer, Ltd.

(57) ABSTRACT

The use of mass defect signatures to impart milliDalton mass differences between isotopically labeled peptides at the $MS^1$-level allows multiplex quantification without the increased mass spectral complexity that occurs with mass difference approaches. Provided herein is a mass defect-based chemical tag, dimethyl pyrimidinyl ornithine (DiPyrO), that is compact and easy to synthesize at high purity in few steps using commercially available starting
(Continued)

materials. The multiplex DiPyrO tags are amine-reactive and can impart a mass difference onto labeled peptides and through calculated substitution of heavy isotopes. DiPyrO offers up to 10-plex quantification on current Orbitrap or FT-ICR platforms without increasing mass spectral complexity. The synthesis of the DiPyrO tag is provided along with viability of the DiPyrO tag for labeling complex proteomics samples using yeast extract digests and its effect on labeled peptides during LC-MS$^2$ analysis. Labeling and quantification of glycans and metabolites using the DiPyrO tag is also demonstrated.

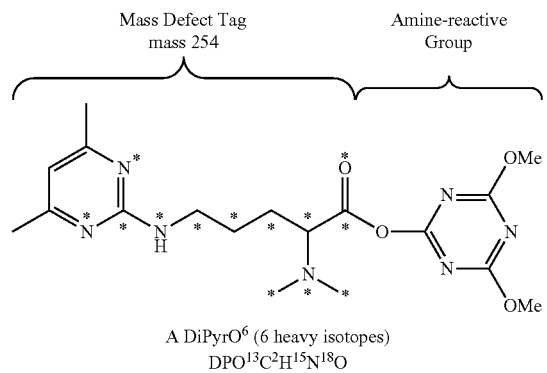

A DiPyrO$^6$ (6 heavy isotopes)
DPO$^{13}$C$^2$H$^{15}$N$^{18}$O

21 Claims, 30 Drawing Sheets

(56) References Cited

U.S. PATENT DOCUMENTS

| 2010/0178710 | A1 | 7/2010 | Hamon et al. | |
|---|---|---|---|---|
| 2013/0078728 | A1* | 3/2013 | Li | C07D 207/46 436/86 |
| 2014/0120565 | A1* | 5/2014 | Coon | G01N 33/6848 435/23 |

OTHER PUBLICATIONS

Hebert et al. (2013) "Amine-reactive Neutron-encoded Labels for Highly Plexed Proteomic Quantitation", Mol. Cell Proteomeics, 12(11):3360-3369.
Extended European Search Report, dated May 10, 2019, corresponding to International Application No. PCT/US2016/057156 (filed Oct. 14, 2016), 9 pp.
Frost et al. (2017) "Mass Defect-Based Dimethyl Pyrimidinyl Ornithine (DiPyrO) Tags for Multiplex Quantitative Proteomics," Anal. Chem. 89(20): 10798-10805.
Gurbuz et al. (2014) "LC-MS investigations on interactions between isolated [beta]-lactoglobulin peptides and lipid oxidation product malondi," Food Chemistry, Elsevier LTD 175: 300-305.
Shemyakin et al. (1970) "Mass-spectrometric determination of amino acid sequences in peptides. XIII. Fragmentation of peptides containing asparagine and glutamine groups," Zhurnal Obshchei Khimii, Nauka, RU 40(2): 407-429.
Boersema et al., "Multiplex peptide stable isotope dimethyl labeling for quantitative proteomics", Nat. Protoc., 4:484-494 (2009).
Choe et al., "8-plex quantitation of changes in cerebrospinal fluid protein expression in subjects undergoing intravenous immunoglobulin treatment for Alzheimer's disease", Proteomics, 7(20):36513660 (2007).

Dayon et al., "Relative Quantification of Proteins in Human Cerebrospinal Fluids by MS/MS Using 6-Plex Isobaric Tags", Anal. Chem., 80(8):2921-2931 (2018).
Dikler et al., "Improving mass spectrometric sequencing of arginine-containing peptides by derivatization with acetylacetone", J. Mass Spectrom., 32(12):1337-1349 (1997).
Dongre et al., "Influence of peptide composition, gas-phase basicity, and chemical modification on fragmentation efficiency: Evidence for the mobile proton model", J. Am. Chem. Soc., 118: 8365-8374 (1996).
Foettinger et al., "Derivatisation of arginine residues with malondialdehyde for the analysis of peptides and protein digests by LC-ESI-MS/MS", J. Mass Spectrom., 41: 623-632. (2006).
Frost et al., "Development and characterization of novel 8-plex DiLeu isobaric labels for quantitative proteomics and peptidomics", Rapid Common. Mass Spectrom., 29:1115-1124 (2015).
Greer, "Novel isotopic N,N-dimethyl leucine (iDiLeu) reagents enable absolute quantification of peptides and proteins using a standard curve approach", J. Am. Soc. Mass. Spectrom., 26:107-119 (2015).
Gygi et al., "Quantitative analysis of complex protein mixtures using isotope-coded affinity tags", Nat. Biotechnol., 17:994-999 (1999).
Hebert et al., "Amine-reactive Neutron-encoded Labels for Highly Proteomic Quantitation", Mol. Cell Proteomeics, 12:3360-3369 (2013).
Hebert et al., "Neutron-encoded mass signatures for multiplexed proteome quantification", Nat. Meth., 10:332-334 (2013).
Hebert et al., "FTMS enabled neturon-encoded chemical tags: 4, 12, and 36 plexes," Presentation, pp. 1-79 (2013).
Hsu et al., "Stable-isotope dimethyl labeling for quantitative proteomics", Anal. Chem., 75:6843-6852 (2003).
Kuyama et al., "An improved method for de novo sequencing of arginine-containing, Nalphatris (2,4,6-trimethoxyphenyl) phosphonium-acetylated peptides", Rapid Commun. Mass Spectrom., 22: 2063-2072 (2008).
Leitner et al., "Improving fragmentation of poorly fragmenting peptides and phosphopeptides during collision-induced dissociation by malondialdehyde modification of arginine residues", J. Mass Spectrom., 42: 950-959 (2007).
Leitner et al., "Probing of arginine residues in peptides and proteins using selective tagging and electrospray ionization mass spectrometry", J. Mass Spectrom., 38: 891-899 (2003).
Leitner et al., "Effects of an arginine-selective tagging procedure on the fragmentation behavior of peptides studied by electrospray ionization tandem mass spectrometry (ESI-MS/MS," Anal. Chim. Acta., 528: 165-173 (2005).
McAlister et al., "MultiNotch MS3 Enables Accurate, Sensitive, and Multiplexed Detection of Differential Expression across Cancer Cell Line Proteomes" Anal. Chem., 86(14):7150-7158 (2014).
McClatchy et al., "15N Metabolic Labeling of Mammalian Tissue with Slow Protein Turnover", J. Proteome Res., 6:2005-2010 (2007).
Merrill et al., "NeuCode labels for relative protein quantification", Mol. Cell Proteomics, 13:2503-2512 (2014).
Molina et al., "Temporal profiling of the adipocyte proteome during differentiation using a five-plex SILAC based strategy", J. Proteome Res., 8: 48-58 (2009).
Morris et al., "Studies towards the complete sequence determination of proteins by mass spectrometry: Derivatisation of methionine, cysteine and arginine containing peptides," Biochem. and Biophys. Res. Comm., 51: 247-255. (1973).
Oda et al., "Accurate quantitation of protein expression and site-specific phosphorylation", Proc. Natl. Acad. Sci., 96: 6591-6596, Rockefeller University, New York, USA (Jun. 1999).
Ong et al., "Stable Isotope Labeling by Amino Acids in Cell Culture, SILAC, as a Simple and Accurate Approach to Expression Proteomics", Molecular & Cellular Proteomics, 1:376-386, The Am. Soc. for Biochem. and Mol. Bio., (May 1, 2002).
Onofrejova et al., "Malondialdehyde tagging improves the analysis of arginine oligomers and arginine-containing dendrimers by HPLC-MS", J. Sep. Sci., 31: 499-506 (2008).

(56) References Cited

OTHER PUBLICATIONS

Ow et al., iTRAQ underestimation in simple and complex mixtures: "the good, the bad and the ugly", *J. Proteome Res.*, 8:5347-5355 (2009).
Pan et al., "Single peptide-based protein identification in human proteome through MALDI-TOF MS coupled with amino acids coded mass tagging", *Anal. Chem.*, 75: 1316-1324 (2003).
Rauniyar et al., "Stable isotope labeling of mammals (SILAM) for in vivo quantitative proteomic analysis", *Methods*, 61:260-268 (2013).
Rhoads et al., "Neutron-Encoded Mass Signatures for Quantitative Top-Down Proteomics", *Anal. Chem.*, 86: 2314-2319 (2014).
Richards et al., "Neutron-encoded Signatures Enable Product Ion Annotation From Tandem Mass Spectra", *Mol. Cell Proteomics*, 12:3812-3823 (2013).
Rose et al., "NeuCode Mouse: Multiplexed Proteomics Analysis Reveals Tissue Specific Effects of Deubiquitinase Deletion", pp. 1-65, Presentation in Baltimore, MD (2014).
Rose et al., "Neutorn Encoded Labeling for Peptide Identification", *Anal. Chem.*, 85: 5129-5137 (2013).
Ross et al., "Multiplexed protein quantitation in *Saccharomyces cerevisiae* using amine-reactive isobaric tagging reagents", 3(12):1154-1169 (2004).
Sheng et al., "Preprocessing Significantly Improves the Peptide/Protein Identification Sensitivity of High-Resolution Isobarically Labeled Tandem Mass Spectrometry Data", *Mol. Cell Proteomics*, 14: 405-417 (2015).
Sullivan et al., "The exploitation of selective cleavage of singly protonated peptide ions adjacent to aspartic acid residues using a quadrupole orthogonal time-of-flight mass spectrometer equipped with a matrix-assisted laser desorption/ionization source", *Int. J. Mass Spectrom.*, 210-211: 665-676 (2001).
Swaney et al., "Decision Tree-Driven Tandem Mass Spectrometry for Shotgun Proteomics", *Nat. Meth.*, 5: 959-964 (2008).
Tang et al., "Fragmentation reactions of multiply-protonated peptides and implications for sequencing by tandem mass spectrometry with low-energy collision-induced dissociation", *Anal. Chem.*, 65:2824-2834 (1993).
Thompson et al., "Tandem Mass Tags: A Novel Quantification Strategy for Comparative Analysis of Complex Protein Mixtures by MS/MS", *Anal. Chem.*, 75:1895-1904 (2003).
Ting et al., "MS3 eliminates ratio distortion in isobaric multiplexed quantitative proteomics," *Nat. Meth.*, 8:937-940 (Oct. 2011).
Ulbrich et al., "Organic Acid Quantitation by NeuCode Methylamidation", *Anal. Chem.*, 86: 4402-4408 (2014).
Ulbrich et al., "Neutron-encoded protein quantification by peptide carbamylation", *J. Am. Soc. Mass Spectrom.*, 25(1):6-9 (2014).
Vincent, et al., "Automated gas-phase purification for accurate, multiplexed quantification on a stand-alone ion-trap mass spectrometer", *Anal. Chem.*, 85:2079-2086 (2013).
Wenger et al., "Gas-phase purification enables accurate, multiplexed proteome quantification with isobaric tagging", *Nat. Meth.*, 8:933-935 (2011).
Wu et al., "Metabolic Labeling of Mammalian Organisms with Stable Isotopes for Quantitative Proteomic Analysis", *Anal. Chem.*, 76: 4951-4959 (2004).
Xiang et al., "N,N-dimethyl Leucines as Novel Isobaric Tandem Mass Tags for Quantitative Proteomics and Peptidomics", *Anal. Chem.*, 82:2817-2825 (2010).
Zhang et al., "Controlling Deuterium Isotope effects in Comparative Proteomics", *Anal. Chem.*, 74:3662-3669 (2002).
Zhou et al., "Mass defect-based pseudo-isobaric dimethyl labeling for proteome quantification", *Anal. Chem.*, 85: 10658-10663 (2013).
International Search Report and Written Opinion, dated Dec. 22, 2016, in Application No. PCT/US2016/057156 (filed Oct. 14, 2016), 7 pp.
Burlet et al. (1993) "Decompositions of cationized heterodimers of amino acids in relation to charge location in peptide ions," J Am Soc Mass Spectrom 4(6):461-469.
Japanese Office Action, dated Sep. 29, 2020, corresponding to Japanese Patent Application No. P2018-513641, 9 pp.
Shek et al. (2006) "Fragmentations of Protonated Arginine, Lysine and Their Methylated Derivatives: Concomitant Losses of Carbon Monoxide or Carbon Dioxide and an Amine," J. Phys. Chem. A 110(27):8282-8296.

* cited by examiner

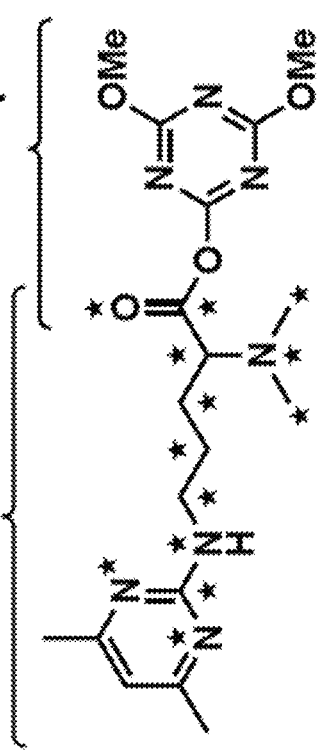
Figures 1A-1F

DiPyrO² (2 heavy isotopes)

| 2-plex | DiPyrO label | Stable Isotopes ¹³C | ²H | ¹⁵N | ¹⁸O | Isotope mass | Δ mDa |
|---|---|---|---|---|---|---|---|
| | DPO₀₀₂₀ | 0 | 0 | 2 | 0 | 1.99407 | 0 |
| | DPO₀₂₀₀ | 0 | 2 | 0 | 0 | 2.01255 | 18.48 |
| 3-plex | DPO₀₀₂₀ | 0 | 0 | 2 | 0 | 1.99407 | 0 |
| | DPO₀₀₀₁ | 0 | 0 | 0 | 1 | 2.00424 | 10.17 |
| | DPO₀₂₀₀ | 0 | 2 | 0 | 0 | 2.01255 | 8.31 |
| 4-plex | DPO₀₀₂₀ | 0 | 0 | 2 | 0 | 1.99407 | 0 |
| | DPO₁₀₁₀ | 1 | 0 | 1 | 0 | 2.00039 | 6.32 |
| | DPO₂₀₀₀ | 2 | 0 | 0 | 0 | 2.00671 | 6.32 |
| | DPO₀₂₀₀ | 0 | 2 | 0 | 0 | 2.01255 | 5.84 |

Labeled yeast digest – Resolving power comparison

DiPyrO Tags *(Lys-C digest)*

NeuCode SILAC *(Lys-C digest)*

| | DiPyrO label | Stable Isotopes | | | | Isotope mass | Δ mDa |
|---|---|---|---|---|---|---|---|
| | | $^{13}C$ | $^{2}H$ | $^{15}N$ | $^{18}O$ | | |
| 9-plex | DPO$_{0020}$ | 0 | 0 | 2 | 0 | 1.99407 | 0 |
| | DPO$_{0200}$ | 0 | 2 | 0 | 0 | 2.01255 | 18.48 |
| | DPO$_{0041}$ | 0 | 0 | 4 | 1 | 5.99238 | 0 |
| | DPO$_{2220}$ | 2 | 2 | 2 | 0 | 6.01333 | 20.95 |
| | DPO$_{0600}$ | 0 | 6 | 0 | 0 | 6.03766 | 24.33 |
| | DPO$_{6040}$ | 6 | 0 | 4 | 0 | 10.00827 | 0 |
| | DPO$_{0640}$ | 0 | 6 | 4 | 0 | 10.02580 | 17.53 |
| | DPO$_{6400}$ | 6 | 4 | 0 | 0 | 10.04524 | 19.44 |
| | DPO$_{0X00}$ | 0 | 10 | 0 | 0 | 10.06277 | 17.53 |

Figure 22

DiPyrO² Isotopic Structures 3.2

¹⁸O 2.0042 Da 2.1
3.1
4.1

¹⁵N₂ 1.9941 Da 4.3

¹³C₂ 2.0067 Da 4.2

¹³C¹⁵N 2.0004 Da 2.2
3.3
4.4

²H₂ 2.0126 Da

DiPyrO¹⁰ Isotopic Structures 3.1
4.1
5.1
6.1
9.1
10.1

$^{13}C_6{}^{15}N_4$
10.0083 Da 5.1

$^{13}C_8{}^{15}N_2$
10.0209 Da 10.2

$^{13}C_4{}^2H_2{}^{15}N_4$
10.0141 Da 4.2
9.3
10.4

$^2H_6{}^{15}N_4$
10.0258 Da 6.1
9.1

$^2H_4{}^{15}N_4{}^{18}O$
10.0175 Da 6.3

$^{13}C_2{}^2H_4{}^{15}N_2{}^{18}O$
10.0301 Da 10.3

$^{13}C_2{}^2H_4{}^{15}N_4$
10.0200 Da 9.4

$^{13}C_8{}^{18}O$
10.0311 Da

MASS DEFECT-BASED MULTIPLEX DIMETHYL PYRIMIDINYL ORNITHINE (DIPYRO) TAGS FOR HIGH-THROUGHPUT QUANTITATIVE PROTEOMICS AND PEPTIDOMICS

CROSS-REFERENCE TO RELATED APPLICATIONS

This application is a U.S. National Stage Application filed under 35 U.S.C. § 371 of International Application No. PCT/US2016/057156, filed Oct. 14, 2016, which claims the benefit of U.S. Provisional Application No. 62/241,590, filed Oct. 14, 2015. Both of these applications are hereby incorporated by reference in their entireties.

STATEMENT REGARDING FEDERALLY SPONSORED RESEARCH OR DEVELOPMENT

This invention was made with government support under DK071801 awarded by the National Institutes of Health. The government has certain rights in the invention.

BACKGROUND OF INVENTION

Stable-isotope labeling is a core technology for MS-based quantitative proteomics that has seen rapid advances in recent years. Heavy carbon, hydrogen, nitrogen, and oxygen atoms are incorporated onto peptides either metabolically or chemically to impart mass differences that can be detected in mass spectra to differentiate the samples and allow comparison of ion intensities for relative quantification (Oda et al., PNAS, 1999, 96:6591-6596; Ong et al., Mol Cell Proteomics, 2002, 1:376-386; Pan et al., Anal Chem, 2003, 75: 1316-1324; Wu et al., Anal Chem, 2004, 76: 4951-4959; Gygi et al., Nat Biotechnol, 1999, 17:994-999; Thompson et al., Anal Chem, 2003, 75:1895-1904; Ross et al., Mol Cell Proteomics, 2004, 3:1154-1169; Hsu et al., Anal Chem, 2003, 75:6843-6852; and Boersema et al., Nat Protoc, 2009, 4:484-494).

There are numerous approaches to introduce stable isotopes into peptides, such as stable isotope labeling by amino acids in cell culture (SILAC), isobaric tagging (TMT/iTRAQ), and iCAT. In most conventional approaches, however, these methods incorporate heavy isotopes to increase mass by at least 1 Da.

In conventional methods, a mass difference of 4 Da or greater is ideal in order to minimize overlap between isotopic clusters in $MS^1$ spectra. The incremental increase of spectral complexity resulting from the increase in multiplexing, which consequently reduces proteomic coverage, has generally limited mass difference approaches, namely SILAC, to triplex comparisons, though 5-plex SILAC and 5-plex dimethyl labeling techniques, under special considerations, have been reported (Molina et al., J Proteome Res, 2009, 8: 48-58; and Wu et al., Chem Commun, 2014, 50:1708).

High levels of multiplexing have been achieved by isobaric chemical labeling approaches such as iTRAQ, TMT, and DiLeu isobaric tags, which provide quantification at the $MS^2$ level without increasing $MS^1$ spectral complexity (Ross et al., Mol Cell Proteomics, 2004, 3:1154-1169; Choe et al., Proteomics, 2007, 7:3651-3660; Thompson et al., Anal Chem, 2003, 75:1895-1904; Dayon et al., Anal Chem 2008, 80:2921-2931; Xiang et al., Anal Chem, 2010, 82:2817-2825; and Frost et al., Rapid Commun Mass Spectrom 2015, 29:1115-1124).

Isobaric labeling addresses the problem of increases in mass spectra complexity by concealing the quantitative information in the $MS^1$ scan, thereby permitting a higher level of multiplexing than obtained via conventional SILAC methods. However, isobaric labeling suffers from ratio suppression and imprecision due to rampant co-isolation of precursors in complex samples (Ow et al., J Proteome Res, 2009, 8:5347-5355), and proposed solutions of employing ion/ion reactions to 'purify' precursors (QuantMode) (Wenger et al., Nat Meth, 2011, 8:933-935; and Rensvold et al., Anal Chem, 2013, 85:2079-2086) or using $MS^3$-based reporter ion quantification (Ting et al., Nat Meth, 2011, 8:937-940; and McAlister et al., Anal Chem, 2014, 86:7150-7158) both reduce instrument duty cycle and sensitivity with the consequence of greatly reduced numbers of identifications and quantified peptides. The flagship Orbitrap Fusion tribrid mass spectrometer is equipped with synchronous precursor selection of multiple $MS^2$ fragment ions for HCD $MS^3$ analysis to specifically address this issue and provide accurate reporter ion signals without steep penalty to sensitivity or quantification rate.

The increased accessibility of high-resolution MS platforms has enabled increases in the multiplexing capabilities of the aforementioned strategies through the use of mass defects. The isobaric 6-plex TMT reagents were increased to 8-plex by exploiting subtle relative mass differences between $^{12}C/^{13}C$ and $^{14}N/^{15}N$ isotopes—by substituting a $^{15}N$ in place of a $^{14}N$ atom and a $^{13}C$ in place of a $^{12}C$ atom. The resulting reporter isotopologues differ in mass by 6.32 mDa and can be distinguished at an MS' resolving power of 30K (at m/z 400). The TMT reagents are now offered as a 10-plex set with four mass defect-based isotopologues, and the multiplexing capacity of isobaric DiLeu reagents have been tripled from 4-plex to 12-plex with the addition of eight mass defect-based isotopologues. Pseudo-isobaric dimethyl labeling (pIDL) uses mass defects between isotopes of C and H and high-resolution $MS^2$ for quantification (Zhou et al., Anal Chem, 2013, 85: 10658-10663). Neutron-encoding, or NeuCode, is a term coined by Coon and coworkers for mass defect-based isotope labeling quantification at the $MS^1$ level (Hebert et al., Nat Meth, 2013, 10:332-334).

NeuCode SILAC is a cell culture metabolic labeling strategy that exploits mass defects between isotopes of C, H, and N in lysine isotopologues that carry eight isotopes in different configurations, which result in mass differences ranging from as little as 5.8 mDa to as much as 36 mDa (Hebert et al., Nat Meth, 2013, 10:332-334; and Merrill et al., Mol Cell Proteomics, 2014, 13:2503-2512). The mDa mass defect signatures of peptides incorporating NeuCode lysines are concealed at low to moderate $MS^1$ resolving powers but are revealed at high resolving powers (>200K). Thus, the strategy permits multiplexing without the increased spectral complexity that accompanies traditional SILAC, and since quantification is done at the $MS^1$ level, it doesn't suffer from poor quantitative accuracy due to precursor coisolation like isobaric labeling does. The multiplexing ability of NeuCode scales with $MS^1$ resolution-duplex quantification using 36 mDa lysines requires a resolving power of 240K for quantification of >85% of a sample's proteome, while triplex and 4-plex quantification using 18 mDa and 12 mDa lysines requires resolving powers of 480K and 960K, respectively. Such high resolutions require the most sophisticated Fourier transform ion cyclotron resonance (FT-ICR) instruments or Orbitrap platforms employing ultra-high field detectors, and as such, the technology is not yet widely usable for a majority of researchers.

NeuCode lysines have been used in both SILAC and SILAM applications, which are limited to metabolic labeling of organisms (Hebert et al., Nat Meth, 2013, 10:332-334; Merrill et al., Mol Cell Proteomics, 2014, 13:2503-2512; Rose et al., Anal Chem, 2013, 85: 5129-5137; Richards et al., Mol Cell Proteomics, 2013, 12:3812-3823; Rhoads et al., Anal Chem, 2014, 86: 2314-2319; and Rose et al., "NeuCode Mouse: Multiplexed Proteomics Analysis Reveals Tissue Specific Effects of Deubiquitinase Deletion", presentation in Baltimore, Md., 2014, pp. 1-65).

Mass defect-based chemical labeling approaches reported by Coon and coworkers under the NeuCode moniker include duplex quantification via carbamylation (Ulbrich et al., J Am Soc Mass Spectrom, 2014, 25:6-9) and methylamination (Ulbrich et al., Anal Chem, 2014, 86: 4402-4408) as well as multiplex quantification via amine-reactive tags (Hebert et al., Mol Cell Proteomeics, 2013, 12:3360-3369). The amine-reactive NeuCode tags employ six heavy isotopes ($^{13}$C and $^{15}$N) in differing configurations to create a 4-plex set of tags differing in mass by 12.6 mDa. However, the tag consists of three amino acids and is consequently extremely large at 431 Da. One of the amino acids is arginine, which inhibits backbone fragmentation due to charge sequestration (Tang et al., Anal Chem, 1993, 65:2824-2834; and Dikler et al., J Mass Spectrom, 1997, 32:1337-1349). While useful for demonstrating the concept of a multiplexed mass defect-based tag for quantitative proteomics, the aforementioned limitations may make it somewhat impractical for its intended application.

Accordingly, improved mass defect-based tagging reagents are desired for incorporation into quantitative proteomics workflows that are small in size and do not compromise fragmentation of labeled peptides.

SUMMARY OF THE INVENTION

The present invention provides novel mass defect-based chemical tags based on dimethyl pyrimidinyl ornithine (DiPyrO) and derivatives thereof. These mass defect tags are beneficial in that they are compact, enhance fragmentation of labeled peptides, and are generally easy to synthesize at high purity in just a few steps using commercially available starting materials.

As generally used herein, the terms "DiPyrO mass defect tags" and "DiPyrO tags" include substituted and unsubstituted structures derived from dimethyl pyrimidinyl ornithine such as described in the structures and formulas below. The DiPyrO tags can impart a very small mass difference, (for example, in an embodiment, up to 45.3 mDa or as little as 5.8 mDa) onto labeled samples, thereby allowing the labeled samples to be analyzed by high-resolution MS in parallel and peak areas to be compared to permit relative quantification of the samples from a single LC-MS experiment. Similar mass-difference strategies, such as SILAC or dimethyl labeling, which impart several Da mass differences between samples, increase mass spectral complexity in proportion to the number of quantitative channels, which has the consequence of reducing instrument efficiency, resulting in fewer numbers of peptide and protein identifications. In contrast, the mDa mass differences used by the current mass defect-based strategy are indistinguishable at low to moderate resolutions (<10 k @ m/z 400) and do not significantly increase mass spectral complexity, retaining high rates of identification. The mDa differences can be resolved with a high-resolution (>120 k) MS$^1$ scan to reveal the labeled sample peaks.

As generally used herein, the terms describing the DiPyrO tags may also indicate the number of heavy stable isotopes that can be incorporated into the structure of the DiPyrO tags. For example, the term "DiPyrO$^6$" indicates that six heavy stable isotopes (i.e., $^{13}$C, $^2$H, $^{15}$N, $^{18}$O) can be incorporated into the structure of the tag with the proviso that $^{18}$O isotopes are counted as two heavy isotopes because $^{18}$O is approximately 2 Da heavier than $^{16}$O.

In certain embodiments, the DiPyrO tags are synthesized at high purity in few steps using established and simple chemistry and commercial reagents and isotopes. This makes the technology affordable to produce at high yield in a short time scale. The synthetic route makes it possible to formulate numerous isotopologue variants. For example, through calculated substitution of heavy isotopes in the tag structure, DiPyrO tags provide 10-plex quantification on current Orbitrap platforms without increasing mass spectral complexity.

In an embodiment, the invention provides a composition comprising an isotopically enriched compound for use as a labeling reagent in mass spectrometry analysis, said compound having the formula (FX1):

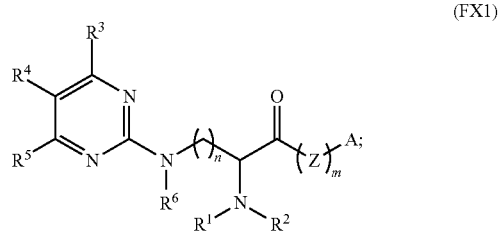

(FX1)

wherein A is an amine reactive group, carbonyl reactive group, or thiol reactive group; wherein Z is a linking group; wherein each of R$^3$-R$^5$ is independently a hydrogen, C$_1$-C$_4$ alkyl or C$_1$-C$_4$ acetyl, or wherein at least two of R$^3$-R$^5$ combine to form an 5 or 6 membered aromatic or alicyclic ring; wherein each of R$^1$, R$^2$ and R$^6$ is independently a hydrogen, C$_1$-C$_4$ alkyl or C$_1$-C$_4$ acetyl; wherein any number of carbons in the compound are $^{12}$C or $^{13}$C; wherein any number of nitrogens in the compound are $^{14}$N or $^{15}$N; wherein any number of hydrogens in the compound are $^1$H or $^2$H; wherein any number of oxygens in the compound are $^{16}$O or $^{18}$O; wherein n is an integer selected from the range of 1 to 5; wherein m is 0 or 1; provided that at least two atoms of formula (FX1) independently selected from a carbon atom, nitrogen atom, oxygen atom and hydrogen atom that is independently a heavy isotope; and wherein the isotopically enriched compound is present in an amount in excess of the natural isotopic abundance.

In some embodiments, the amine reactive group, carbonyl reactive group, or thiol reactive group of formula (FX1) is selected from the group consisting of: a triazine ester, a N-hydroxysuccinimide (NHS) NHS ester, a tetrafluorophenyl (TFP) ester, an isothiocyanate, an isocyanate, a hydrazide, an aminooxy, and iodoacetyl.

In some embodiments, the DiPyrO tags comprise an amine reactive group and can bind to both the N-terminus of a peptide as well as any lysine side chains. For example, in at least one experiment, the labelling efficiency of complex yeast protein extract digests with DiPyrO tags has been observed at a rate of >99% (either N-terminus or lysine) using a 1 hr labeling reaction.

Different isotopically enriched compounds of the invention can have a number of stable heavy isotopes selected over a wide range for different applications. As used herein isotopically enriched compound refers to compound having one or more stable heavy isotopes functioning as an isotopic label. In an embodiment, for example, the isotopically enriched compounds have a number of stable heavy isotopes selected from the group consisting of 2, 3, 4, 5, 6, 7, 8, 9, 10, 11, and 12. In an embodiment, for example, the isotopically enriched compounds have a number of stable heavy isotopes equal to or greater than 1, and optionally for some applications a number of stable heavy isotopes equal to or greater than 4, and optionally for some applications a number of stable heavy isotopes equal to or greater than 10.

Optionally, at least five atoms of formula (FX1) as described herein independently selected from a carbon atom, a nitrogen atom, an oxygen atom and a hydrogen atom are independently heavy isotopes. In an embodiment, the isotopically enriched compound characterized by formula (FX1) as described herein has: at least two $^{13}C$ isotopes; or at least one $^{13}C$ isotope and at least one $^{15}N$ isotope; or at least one $^{13}C$ isotope and at least one 2H isotope; or at least one $^{18}O$ isotope and at least two $^{18}O$ isotope; or at least two $^{15}N$ isotopes; or at least one $^{15}N$ isotope and at least one $^{2}H$ isotope; or at least one $^{15}N$ isotope and at least one $^{18}O$ isotope; or at least two $^{2}H$ isotopes; or at least one $^{2}H$ isotope and at least one $^{18}O$ isotope; or at least two $^{18}O$ isotopes; or at least one $^{13}C$ isotope, at least one $^{15}N$ isotope and at least one $^{2}H$ isotope; or at least one $^{13}C$ isotope, at least one $^{15}N$ isotope and at least one $^{18}O$ isotope.

Optionally, the isotopically enriched compound characterized by formula (FX1) as described herein has: at least two $^{13}C$ isotopes; or at least four $^{13}C$ isotopes; or at least six $^{13}C$ isotopes; or at least four $^{13}C$ isotopes and at least one $^{18}O$ isotope; or at least four $^{13}C$ isotopes and at least two $^{15}N$ isotopes; or at least four $^{13}C$ isotopes and at least two $^{2}H$ isotopes; or at least two $^{15}N$ isotopes; or at least four $^{15}N$ isotopes; or at least four $^{15}N$ isotopes and at least one $^{18}O$ isotope; or at least four $^{15}N$ isotopes and at least two $^{13}C$ isotopes; or at least four $^{15}N$ isotopes and at least two $^{2}H$ isotopes; or at least two $^{15}N$ isotopes, at least two $^{2}H$ isotopes and at least one $^{18}O$ isotope; or at least two $^{15}N$ isotopes, at least two $^{13}C$ isotopes and at least one $^{18}O$ isotope; or at least two $^{15}N$ isotopes, at least two $^{2}H$ isotopes and at least two $^{13}C$ isotopes; or at least two $^{15}N$ isotopes and at least two $^{2}H$ isotopes; or at least two $^{2}H$ isotopes and at least one $^{18}O$ isotope; or at least two $^{13}C$ isotopes and at least two $^{2}H$ isotopes; or at least two $^{2}H$ isotopes; or at least four $^{2}H$ isotopes; or at least six $^{2}H$ isotopes.

In an embodiment, the isotopically enriched compound is characterized by formula (FX2):

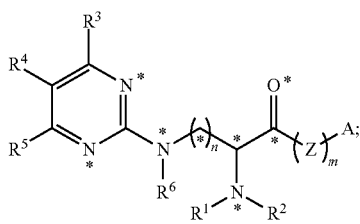

(FX2)

wherein each * symbol independently designates an atom that may be one of the heavy isotopes.

In an embodiment, the isotopically enriched compound is characterized by formula (FX3):

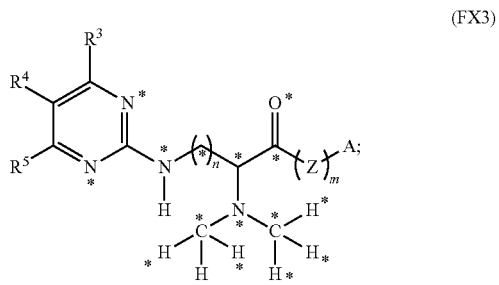

(FX3)

wherein each * symbol independently designates an atom that may be one of the heavy isotopes.

In an embodiment, the isotopically enriched compound is characterized by formula (FX4):

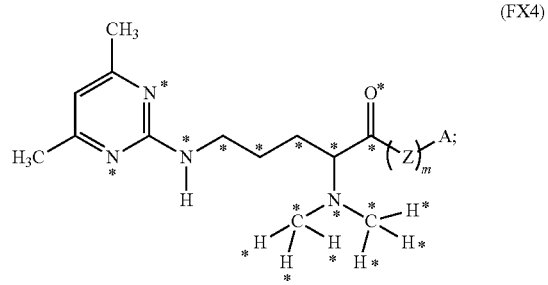

(FX4)

wherein each * symbol independently designates an atom that may be one of said heavy isotopes.

In an embodiment, the isotopically enriched compound is characterized by formula (FX5),

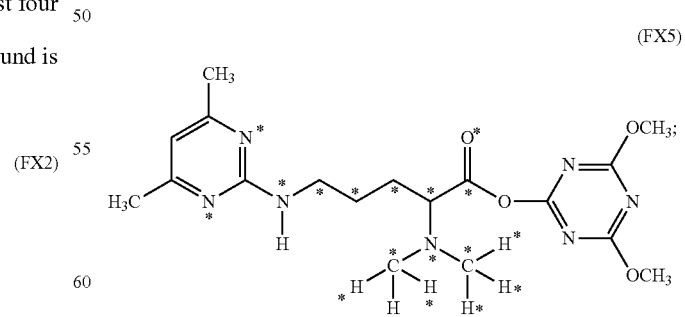

(FX5)

wherein each * symbol independently designates an atom that may be one of said heavy isotopes.

In an embodiment, the isotopically enriched compound is characterized by formula (FX6)
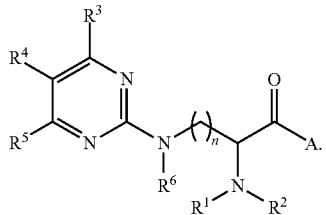
(FX6)
In a further embodiment, the isotopically enriched compound is characterized by formula (FX7), (FX8), (FX9), (FX10), (FX11), (FX12), (FX13), (FX14), (FX15), (FX16) or (FX17):
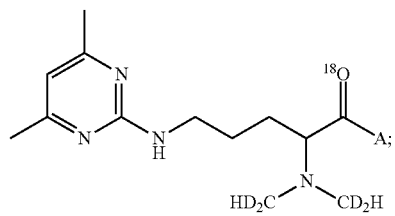
(FX7)
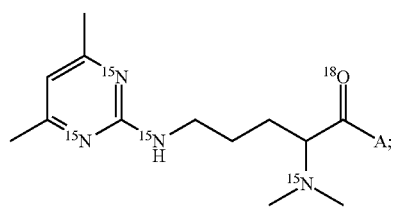
(FX8)
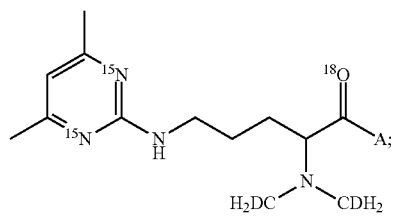
(FX9)
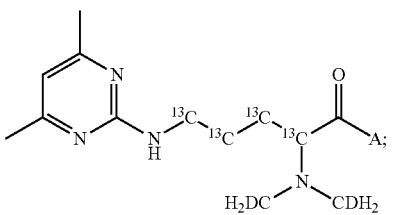
(FX10)
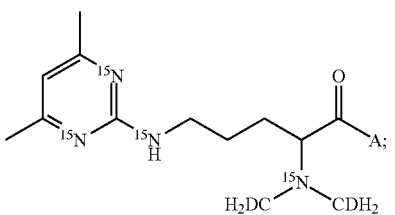
(FX11)
-continued
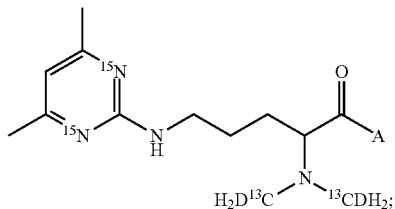
(FX12)
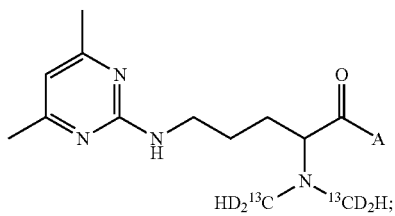
(FX13)
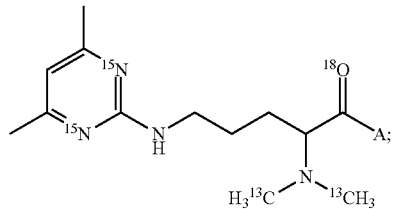
(FX14)
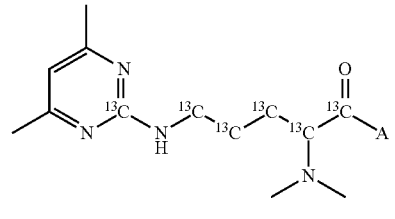
(FX15)
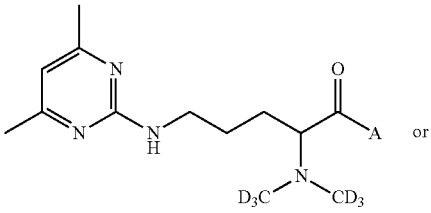
(FX16) or
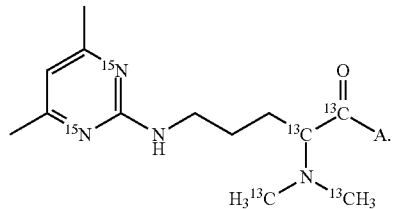
(FX17)

In an embodiment, the isotopically enriched compound is characterized by formula (FX22), (FX23), (FX24), (FX25), or (FX26):

(FX22)
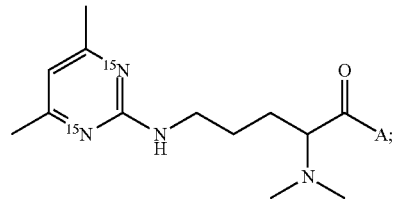

(FX23)
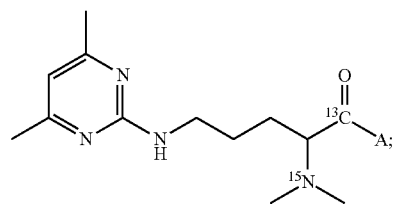

(FX24)
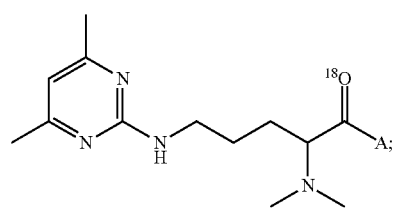

(FX25)
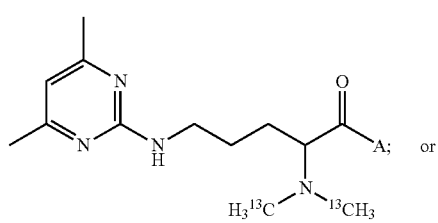

or (FX26)
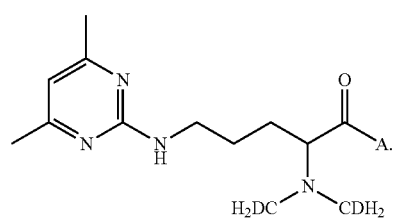

In an embodiment, the isotopically enriched compound is characterized by formula (FX18) or (FX19):

(FX18)
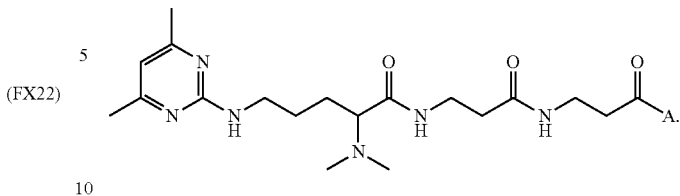
or (FX19)
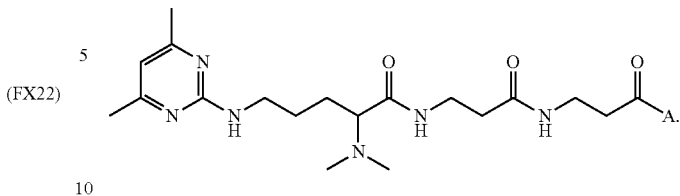

In some embodiments, Z of formula (FX1) is not present or is a linking group having one or more carbon atoms including but not limited to substituted and unsubstituted alkylene groups. In certain embodiments, Z of formula (FX1) is a group corresponding to an amino acid or peptide, including but not limited to beta-alanine or a glycine. In some embodiments, the linking group provides additional sites which can incorporate a heavy isotope label thereby enabling increased multiplexing via mass difference, such as shown formula (FX18) and formula (FX19) wherein each * symbol independently designates an atom that may be one of the heavy isotopes:

(FX18)
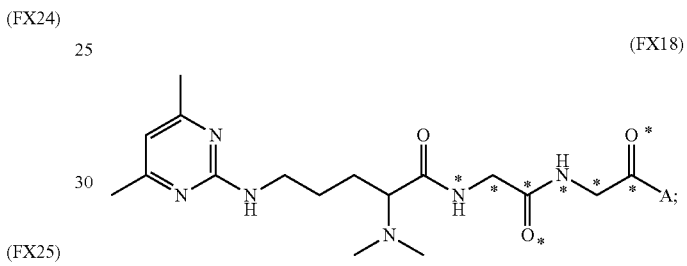

(FX19)
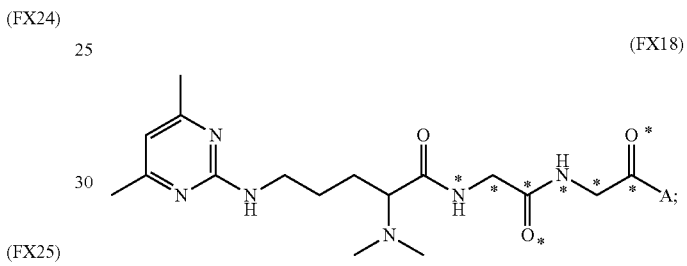

For example, formula (FX18) incorporates a glycine-glycine linker which can be used to incorporate C, N, and O heavy isotopes to achieve +4 Da and +8 Da mass differences, and formula (FX19) incorporates a beta-alanine-beta-alanine linker which can be used to incorporate C and N heavy isotopes to achieve +4 Da and +8 Da mass differences.

In some embodiments, $R^3$ and $R^4$ or $R^4$ and $R^5$ of formula (FX1) combine to form a 6 membered aromatic ring. In certain embodiments, aromatic derivatives of DiPyrO allow for more sensitive fluorescence detection of labeled species. For example, $R^3$ and $R^4$ or $R^4$ and $R^5$ of formula (FX1) combine to form a group corresponding to a benzene according to the following scheme:

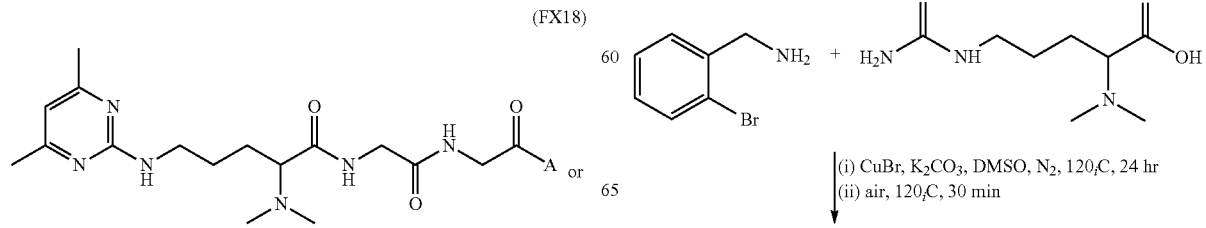

(i) CuBr, $K_2CO_3$, DMSO, $N_2$, 120°C, 24 hr
(ii) air, 120°C, 30 min

-continued

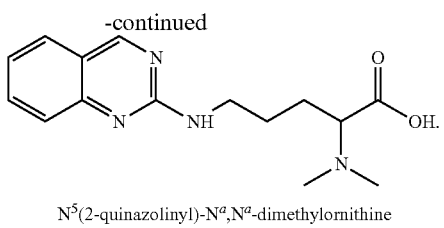

N⁵(2-quinazolinyl)-Nᵃ,Nᵃ-dimethylornithine

In an embodiment, the isotopically enriched compound is characterized by formula (FX20) or formula (FX21):

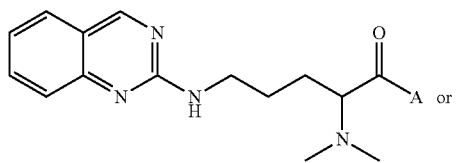

(FX20)

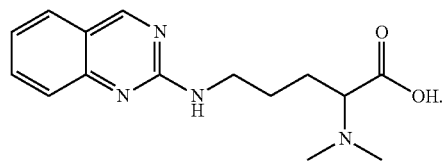

(FX21)

An embodiment of the present invention provides a composition comprising a plurality of different isotopically enriched compounds each independently having the formula (FX1); wherein the different isotopically enriched compounds are isotopologues.

In an embodiment, the invention provides a kit comprising a plurality of different isotopically enriched isotopologues for use as labeling reagents for mass spectrometry analysis, said isotopically enriched isotopologues independently having the formula (FX1):

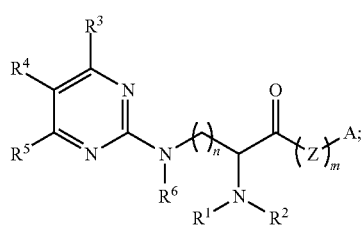

(FX1)

wherein A is an amine reactive group, carbonyl reactive group, or thiol reactive group; wherein Z is a linking group; wherein each of $R^3$-$R^5$ is independently a hydrogen, $C_1$-$C_4$ alkyl or $C_1$-$C_4$ acetyl, or wherein at least two of $R^3$-$R^5$ combine to form an 5 or 6 membered aromatic or alicyclic ring; wherein each of $R^1$, $R^2$ and $R^6$ is independently a hydrogen, $C_1$-$C_4$ alkyl or $C_1$-$C_4$ acetyl; wherein any number of carbons in the compound are $^{12}C$ or $^{13}C$; wherein any number of nitrogens in the compound are $^{14}N$ or $^{15}N$; wherein any number of hydrogens in the compound are $^1H$ or $^2H$; wherein any number of oxygens in the compound are $^{16}O$ or $^{18}O$; wherein n is an integer selected from the range of 1 to 5; wherein m is 0 or 1; wherein at least a portion of said isotopologues are characterized by a mass difference that is less than or equal to 50 mDa; and wherein the isotopically enriched isotopologues are present in an amount in excess of the natural isotopic abundance.

In a further embodiment, the kit comprises 2, 3, 4, 5, 6, 7, 8, 9, 10 or more of said different isotopically enriched isotopologues. Optionally, at least a portion of said isotopologues are characterized by mass differences selected over the range of 5 mDa to 55 mDa, preferably characterized by mass differences less than or equal to 25 mDa.

In an embodiment, at least a portion of the isotopologues are characterized by a mass differences resolvable using a mass spectrometry analysis technique providing a resolving power equal to or greater than 100,000, a resolving power equal to or greater than 120,000, a resolving power equal to or greater than 240,000, or a resolving power equal to or greater than 480,000. The mass spectrometry analysis comprises a $MS^1$ technique, a multiplex technique, a proteomic analysis technique, a glycomic analysis technique, or a metabolomic analysis technique. At least a portion of the isotopologues is reactive with: the amine group, carbonyl group, or thiol group of a peptide, protein, glycan, or metabolite.

In an embodiment, the invention provides a method of labeling a target molecule containing one or more amine groups, said method comprising:
 a) providing said target molecules; and
 b) reacting said target molecules with an isotopically enriched compound, thereby generating isotopically labeled target molecules; wherein each isotopically enriched isotopologue independently has the formula (FX1):

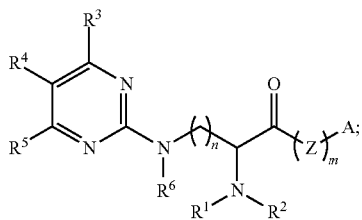

(FX1)

wherein A is an amine reactive group, carbonyl reactive group, or thiol reactive group; wherein Z is a linking group; wherein each of $R^3$-$R^5$ is independently a hydrogen, $C_1$-$C_4$ alkyl or $C_1$-$C_4$ acetyl, or wherein at least two of $R^3$-$R^5$ combine to form an 5 or 6 membered aromatic or alicyclic ring; wherein each of $R^1$, $R^2$ and $R^6$ is independently a hydrogen, $C_1$-$C_4$ alkyl or $C_1$-$C_4$ acetyl; wherein any number of carbons in the compound are $^{12}C$ or $^{13}C$; wherein any number of nitrogens in the compound are $^{14}N$ or $^{15}N$; wherein any number of hydrogens in the compound are $^1H$ or $^2H$; wherein any number of oxygens in the compound are $^{16}O$ or $^{18}O$; wherein n is an integer selected from the range of 1 to 5; wherein m is 0 or 1; provided that at least two atoms of formula (FX1) independently selected from a carbon atom, nitrogen atom, oxygen atom and hydrogen atom that is independently a heavy isotope.

In an embodiment, the invention provides a method of analyzing target molecules using a mass spectrometry technique, said method comprising:
 a) providing said target molecules in a plurality of different samples; and
 b) reacting said target molecules in each sample with a different isotopically enriched isotopologue, thereby generating samples comprising isotopically labeled target molecules, wherein each of said different isotopically enriched isotopologues independently has the formula (FX1):

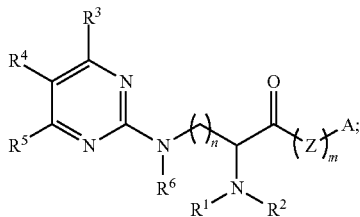

(FX1)

wherein A is an amine reactive group, carbonyl reactive group, or thiol reactive group; wherein Z is a linking group; wherein each of $R^3$-$R^5$ is independently a hydrogen, $C_1$-$C_4$ alkyl or $C_1$-$C_4$ acetyl, or wherein at least two of $R^3$-$R^5$ combine to form an 5 or 6 membered aromatic or alicyclic ring; wherein each of $R^1$, $R^2$ and $R^6$ is independently a hydrogen, $C_1$-$C_4$ alkyl or $C_1$-$C_4$ acetyl; wherein any number of carbons in the compound are $^{12}C$ or $^{13}C$; wherein any number of nitrogens in the compound are $^{14}N$ or $^{15}N$; wherein any number of hydrogens in the compound are $^1H$ or $^2H$; wherein any number of oxygens in the compound are $^{16}O$ or $^{18}O$; wherein n is an integer selected from the range of 1 to 5; wherein m is 0 or 1; provided that at least two atoms of formula (FX1) independently selected from a carbon atom, a nitrogen atom, an oxygen atom and a hydrogen atom are independently heavy isotopes; and wherein at least a portion of said isotopologues are characterized by a mass difference that is less than or equal to 50 mDa; and c) analyzing said isotopically labeled target molecules for each sample using said mass spectrometry technique.

Preferably, 2, 3, 4, 5, 6, 7, 8, 9, 10 or more different samples are reacted with different isotopically enriched isotopologues. Optionally, at least a portion of said isotopologues are characterized by mass differences selected over the range of 5 mDa to 55 mDa, preferably characterized by mass differences less than or equal to 25 mDa.

In an embodiment, the step of analyzing said isotopically labeled analytes for each sample using said mass spectrometry technique is carried out using a mass spectrometry analysis technique providing a resolving power equal to or greater than 100,000, a resolving power equal to or greater than 120,000, a resolving power equal to or greater than 240,000, or a resolving power equal to or greater than 480,000. The mass spectrometry analysis comprises a $MS^1$ technique, a 2-plex, 3-plex, 4-plex, 5-plex, 6-plex, 7-plex, 8-plex, 9-plex or 10-plex multiplex mass spectrometry technique. Optionally, the mass spectrometry analysis comprises a proteomic analysis technique, a glycomic analysis technique, or a metabolomic analysis technique. At least a portion of the isotopologues is reactive with: the amine group, carbonyl group, or thiol group of a peptide, protein, glycan, or metabolite.

In an embodiment, the methods further comprise the step of quantifying the relative amounts of the labeled target molecules in said different samples. Optionally, relative quantification is performed by measuring fluorescence from the labeled target molecules. Relative quantification can be performed at the $MS^1$-level, and unlike isobaric labeling where the quantification is performed at the $MS^2$-level, the measured quantitative ratios are not susceptible to compression due to co-isolation of interfering precursor ions. Iso-baric labeling requires that the peptide be sampled by $MS^2$ in order to generate reporter ions for quantification, while the mass defect strategy does not, since quantitative information is gleaned from relative peak areas of peptide precursors in a high-resolution $MS^1$ scan.

In an embodiment, each of the isotopically enriched isotopologues is independently characterized by formula (FX2):

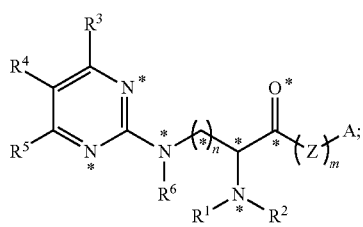

(FX2)

wherein each * symbol independently designates an atom that may be one of the heavy isotopes.

In an embodiment, each of the isotopically enriched isotopologues is independently characterized by formula (FX3):

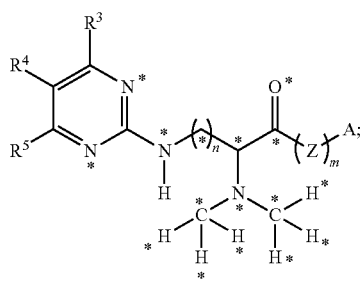

(FX3)

wherein each * symbol independently designates an atom that may be one of the heavy isotopes.

In an embodiment, each of the isotopically enriched isotopologues is independently characterized by formula (FX4):

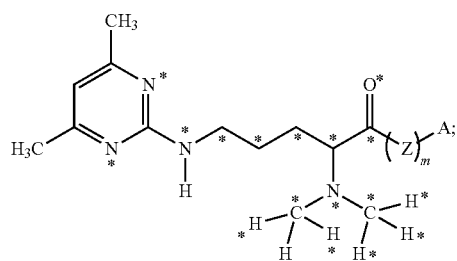

(FX4)

wherein each * symbol independently designates an atom that may be one of said heavy isotopes.

In an embodiment, each of the isotopically enriched isotopologues is independently characterized by formula (FX5), (FX5)

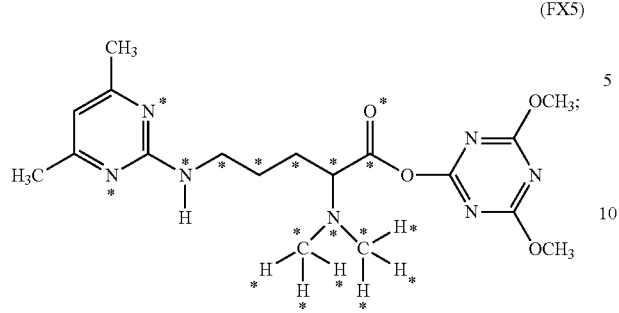

wherein each * symbol independently designates an atom that may be one of said heavy isotopes.

In an embodiment, each of the isotopically enriched isotopologues is independently characterized by formula (FX6)

(FX6)

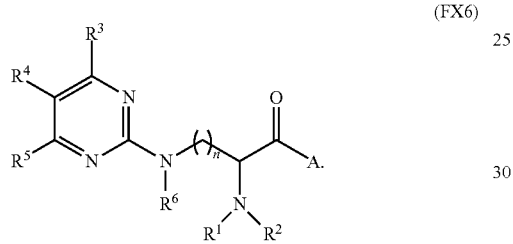

In a further embodiment, each of the isotopically enriched isotopologues is independently characterized by formula (FX7), (FX8), (FX9), (FX10), (FX11), (FX12), (FX13), (FX14), (FX15), (FX16) or (FX17):

(FX7)

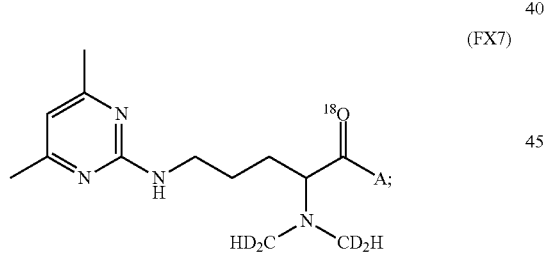

(FX8)

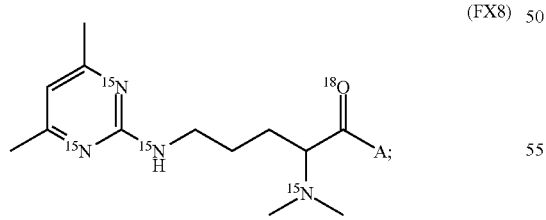

(FX9)

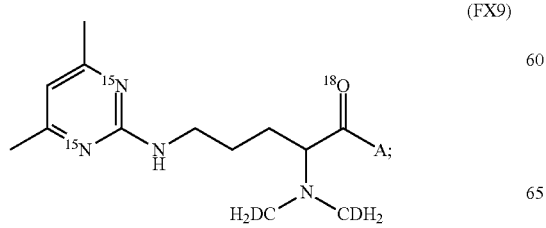

(FX10)

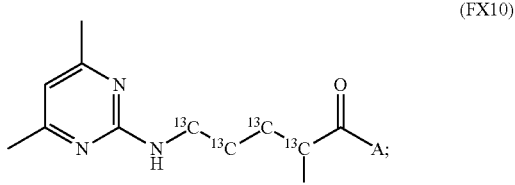

(FX11)

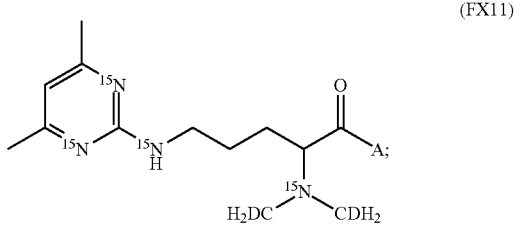

(FX12)

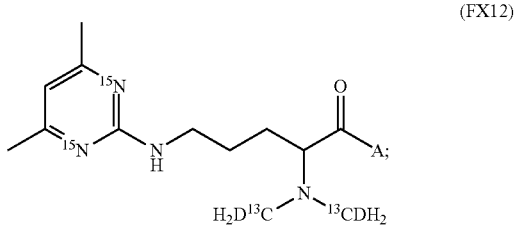

(FX13)

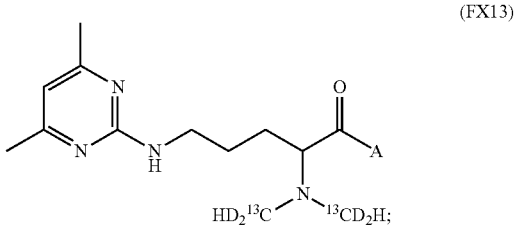

(FX14)

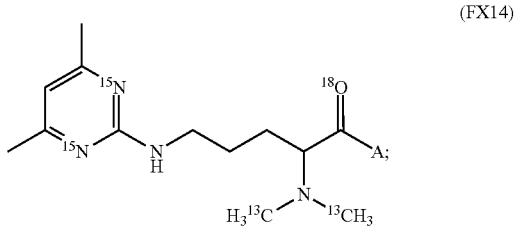

(FX15)

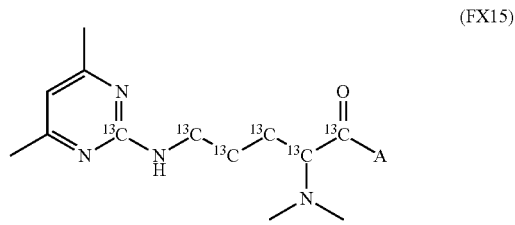

(FX16)

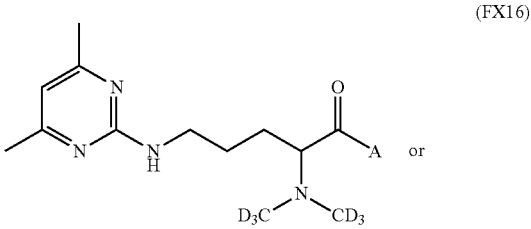

or

-continued

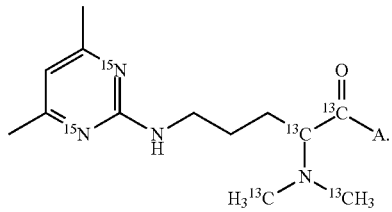
(FX17)

In an embodiment, each of the isotopically enriched isotopologues is independently characterized by formula (FX18) or (FX19):

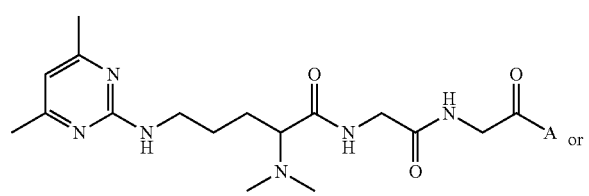
(FX18)

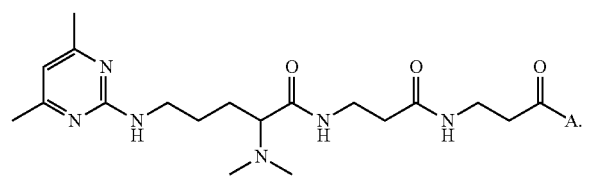
(FX19)

In an embodiment, each of the isotopically enriched isotopologues is independently characterized by formula (FX20) or formula (FX21):

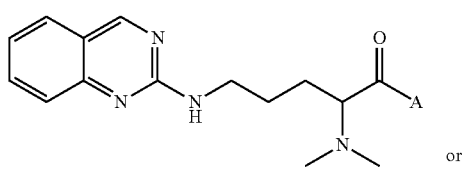
(FX20)

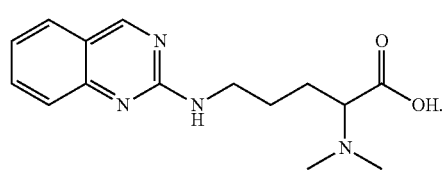
(FX21)

In an embodiment, each of the isotopically enriched isotopologues is independently characterized by formula (FX22), (FX23), (FX24), (FX25), or (FX26):

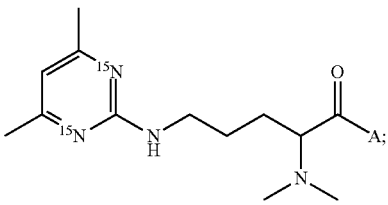
(FX22)

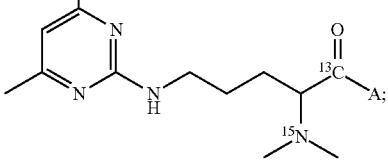
(FX23)

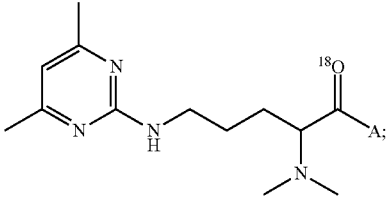
(FX24)

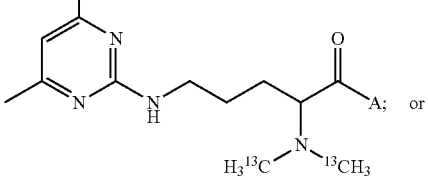
(FX25)

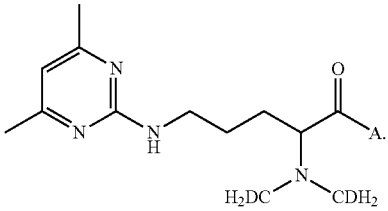
(FX26)

In an embodiment, the present invention provides a method of making an isotopically enriched labeling reagent comprising the steps of: providing an amino acid precursor; chemically reacting said amino acid precursor with a first reagent so as to provide an optionally substituted pyrimidine group; and chemically reacting the carboxylic acid group of said amino acid precursor with a second reagent to provide an amine reactive group, carbonyl reactive group, or thiol reactive group to form said isotopically enriched labeling reagent having the formula:

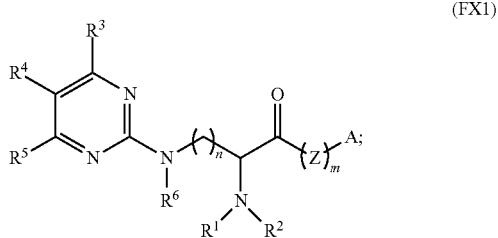

(FX1)

wherein A is an amine reactive group, carbonyl reactive group, or thiol reactive group; wherein Z is a linking group; wherein each of $R^3$-$R^5$ is independently a hydrogen, $C_1$-$C_4$ alkyl or $C_1$-$C_4$ acetyl, or wherein at least two of $R^3$-$R^5$ combine to form an 5 or 6 membered aromatic or alicyclic ring; wherein each of $R^1$, $R^2$ and $R^6$ is independently a hydrogen, $C_1$-$C_4$ alkyl or $C_1$-$C_4$ acetyl; wherein any number of carbons in the compound are $^{12}$C or $^{13}$C; wherein any number of nitrogens in the compound are $^{14}$N or $^{15}$N; wherein any number of hydrogens in the compound are $^1$H or $^2$H; wherein any number of oxygens in the compound are $^{16}$O or $^{18}$O; wherein n is an integer selected from the range of 1 to 5; wherein m is 0 or 1; provided that at least two atoms of formula (FX1) independently selected from a carbon atom, nitrogen atom, oxygen atom and hydrogen atom are independently a heavy isotope; and wherein the isotopically enriched isotopologue is present in an amount in excess of the natural isotopic abundance.

Preferably, the amino acid precursor is an isotopically enriched amino acid precursor, such as isotopically enriched arginine, characterized in that said amino acid precursor contains at least two atoms that are heavy isotopes, wherein said heavy isotopes are present in an amount in excess of the natural isotopic abundance. The first reagent or said second reagent is preferably an isotopically enriched reagent characterized in that said reagent contains at least two atoms that are heavy isotopes, wherein said heavy isotopes are present in an amount in excess of the natural isotopic abundance.

In an embodiment, the carboxylic acid group of said amino acid precursor is reacted to form a triazine ester. In an embodiment, the amino acid precursor is arginine and the method further comprises the step of derivatizing the guanidine group of the arginine to form the optionally substituted pyrimidine group. In a further embodiment, the method further comprises the step of performing palladium-catalyzed dimethylation with formaldehyde on said amino acid precursor prior to forming the optionally substituted pyrimidine group.

In an embodiment, the compound of the invention is characterized by any of formula (FX1)-(FX4) wherein m is equal to 1. In an embodiment, the compound of the invention is characterized by any of formula (FX1)-(FX4) wherein m is equal to 0. As used herein, compounds having formula (FX1)-(FX4) wherein m is equal to 1 refer to compounds that include linking group Z. As used herein, compounds having formula (FX1)-(FX4) wherein m is equal to 0 refers to compounds that do not include linking group Z, for example, wherein amine reactive group A is directly bonded to the carbonyl group of the backbone.

An important aspect of the present methods is use of a series of isotopically enriched compounds having differences in mass that can be resolved using a mass spectrometry analysis technique providing a resolving power equal to or greater than 100,000, a resolving power equal to or greater than 120,000, a resolving power equal to or greater than 240,000, or a resolving power equal to or greater than 480,000. Use of at least a portion of the isotopically enriched compounds having small differences in molecular mass (e.g., less than or equal to 300 mDa) is beneficial in some embodiments for accessing high multiplexing capabilities. In some embodiments, for example, the step of analyzing isotopically enriched compounds comprises resolving differences of the mass to charge ratios and/or molecular masses of the isotopically enriched compounds. In some embodiments, for example, the difference of the molecular masses of a first isotopically enriched compound and a second isotopically enriched compound is less than or equal to 100 mDa. For some applications the difference of the molecular masses of the first isotopically enriched compound and the second isotopically enriched compound is less than or equal to 50 mDa and optionally for some applications the difference of the molecular masses of the first isotopically enriched compound and the second isotopically enriched compound is greater than or equal to 10 mDa. In some embodiments, for example, the difference of the molecular masses of the first isotopically enriched compound and the second isotopically enriched compound is selected over the range of 100 mDa to 1 mDa, and optionally for some applications the difference of the molecular masses of the first isotopically enriched compound and the second isotopically enriched compound is selected over the range of 50 mDa to 1 mDa, and optionally for some applications the difference of the molecular masses of the first isotopically enriched compound and the second isotopically enriched compound is selected over the range of 50 mDa to 5 mDa, and optionally for some applications the difference of the molecular masses of the first isotopically enriched compound and the second isotopically enriched compound is selected over the range of 50 mDa to 1 mDa. In some embodiments, for example, each of isotopically enriched compounds have a molecular mass within 100 mDa to 1 mDa of another isotopically enriched compound, and optionally for some applications each of the isotopically enriched compounds have a molecular mass within 50 mDa to 1 mDa of another isotopically enriched compound, and optionally for some applications each of the isotopically enriched compounds have a molecular mass within 10 mDa to 1 mDa of another isotopically enriched compound. In some embodiments, for example, the molecular masses of all of the isotopically enriched compounds are within a range of 1000 mDa to 1 mDa, and optionally for some applications the molecular masses of all of the isotopically enriched compounds are within a range of 100 mDa to 1 mDa, and optionally for some applications the molecular masses of all of the isotopically enriched compounds are within a range of 50 mDa to 5 mDa.

BRIEF DESCRIPTION OF THE DRAWINGS

FIGS. 1A-1F illustrate a DiPyrO mass defect labeling reagent in an embodiment of the present invention comprising a dimethyl pyrimidinyl ornithine tag (nominal mass of 254 Da) and an amine-reactive triazine ester group. A total of up to 6 heavy stable isotopes ($^{13}$C, $^2$H, $^{15}$N, $^{18}$O) are incorporated into the structure of the mass defect-based tag DiPyrO$^6$ (FIG. 1A) in differing configurations to create a 2-plex set (FIG. 1B), a 3-plex set (FIG. 1C), a 4-plex set (FIG. 1D), a 6-plex set (FIG. 1E), and an 8-plex set (FIG. 1F) with minimum mass defects of 45.28 mDa, 20.95 mDa, 12.64 mDa, 8.31 mDa, and 5.84 mDa, respectively.

Figure 2A:
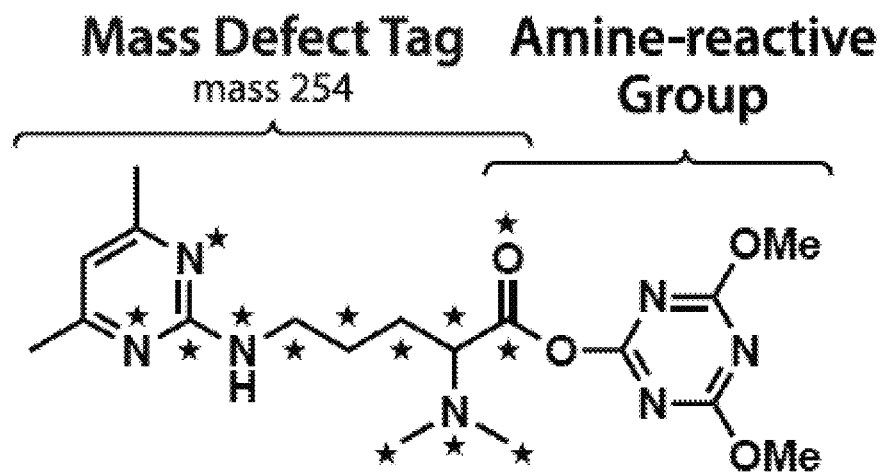
FIG. 2 illustrates DiPyrO mass defect labeling reagents in an embodiment of the present invention similar to FIGS.
Figure 2B:
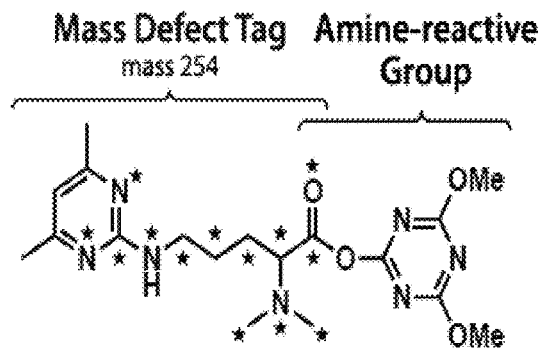

1B-1F but where 2 (FIG. 2A) or 10 (FIG. 2B) heavy stable isotopes ($^{13}$C, $^2$H, $^{15}$N, $^{18}$O) are incorporated into the structure of the mass defect based tag in differing configurations to create additional multiplex sets with nominal tag masses of 250 Da (DiPyrO$^2$) and 258 Da (DiPyrO$^{10}$). Multiplex DiPyrO$^2$, DiPyrO$^6$, and DiPyrO$^{10}$ sets may be used in conjunction in a single experiment to increase multiplexing via three clusters, spaced 4 Da apart, of mass defect-based quantitative channels.

Figure 3:
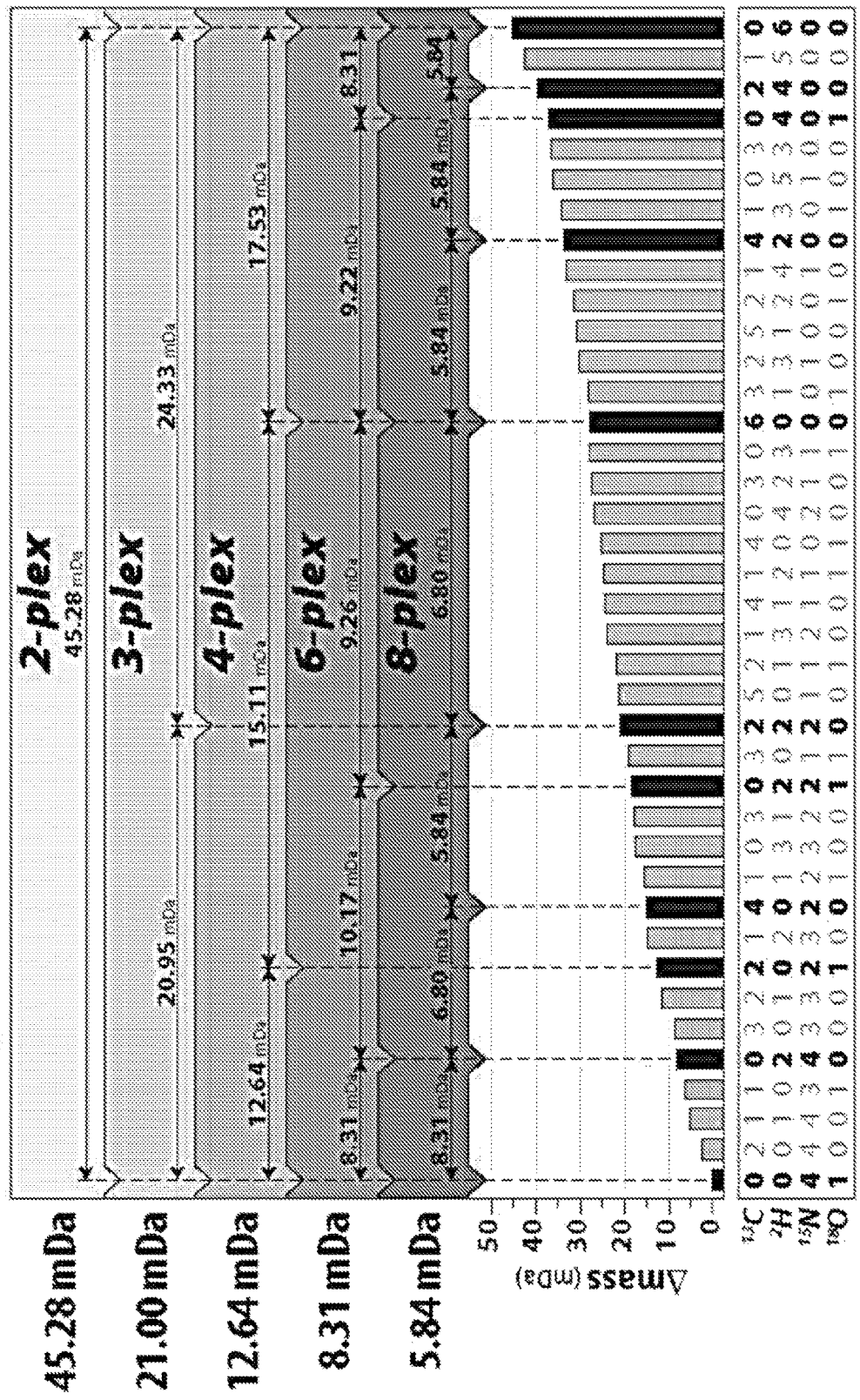

FIG. 3 illustrates possible heavy isotope configurations of the DiPyrO$^6$ 2-plex, 3-plex, 4-plex, 6-plex and 8-plex sets of FIGS. 1B-1F.

Figure 4:
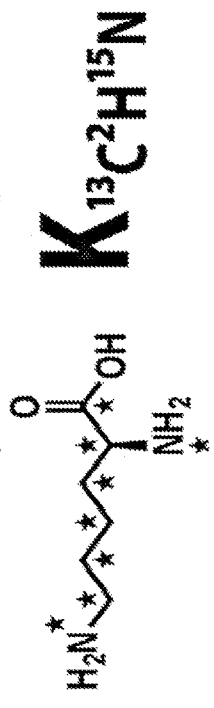
Figure 4:
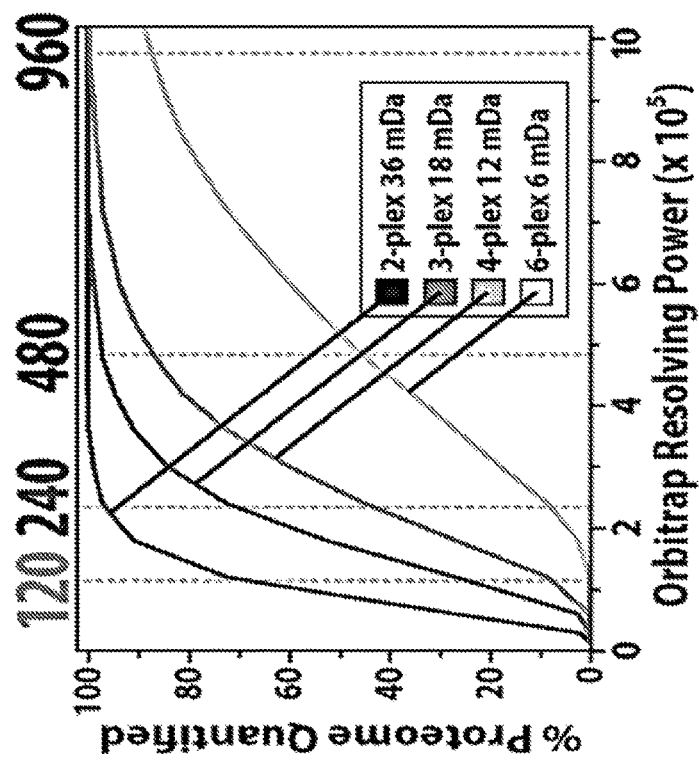
Figure 4:
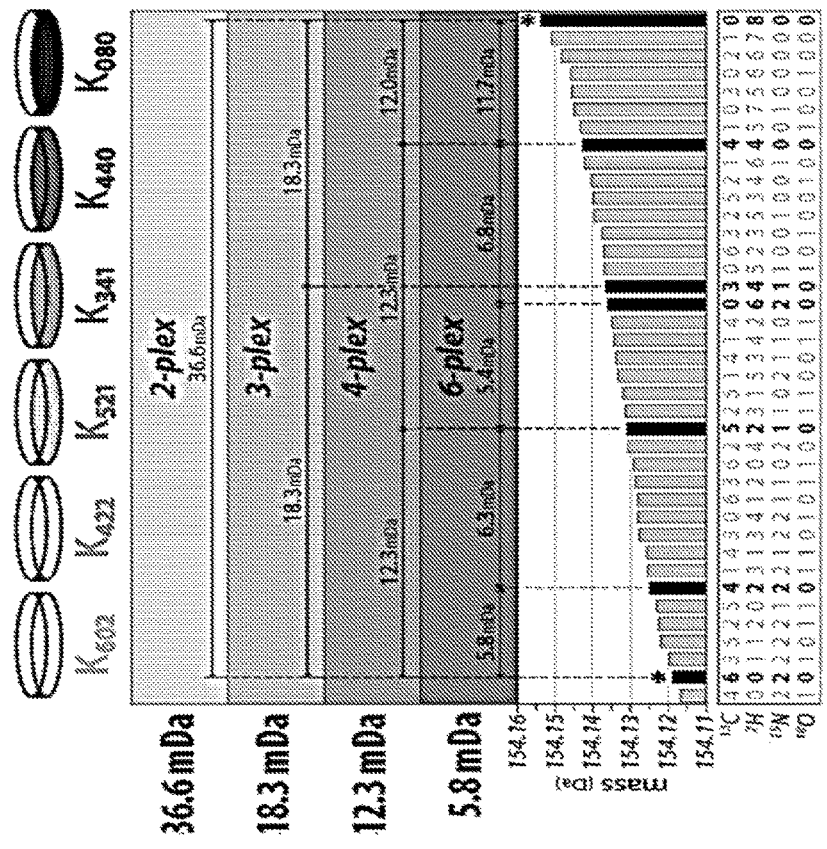

FIG. 4 shows heavy isotope configurations of an isotopically labeled lysine (K) able to be used in NeuCode SILAC and the resolving power necessary to identify different amounts of a yeast proteome using the NeuCode-labeled lysines.

Figure 5:
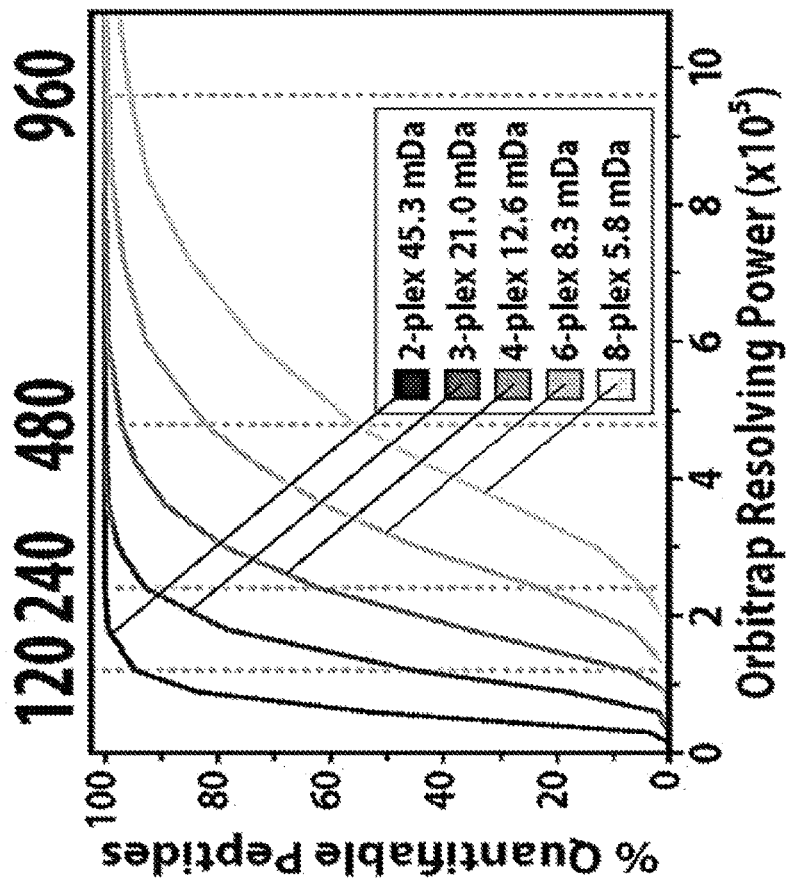

FIG. 5 describes the resolving power requirements necessary to identify different amounts of a yeast proteome using DiPyrO$^6$-labeled tryptic peptides.

Figure 6:
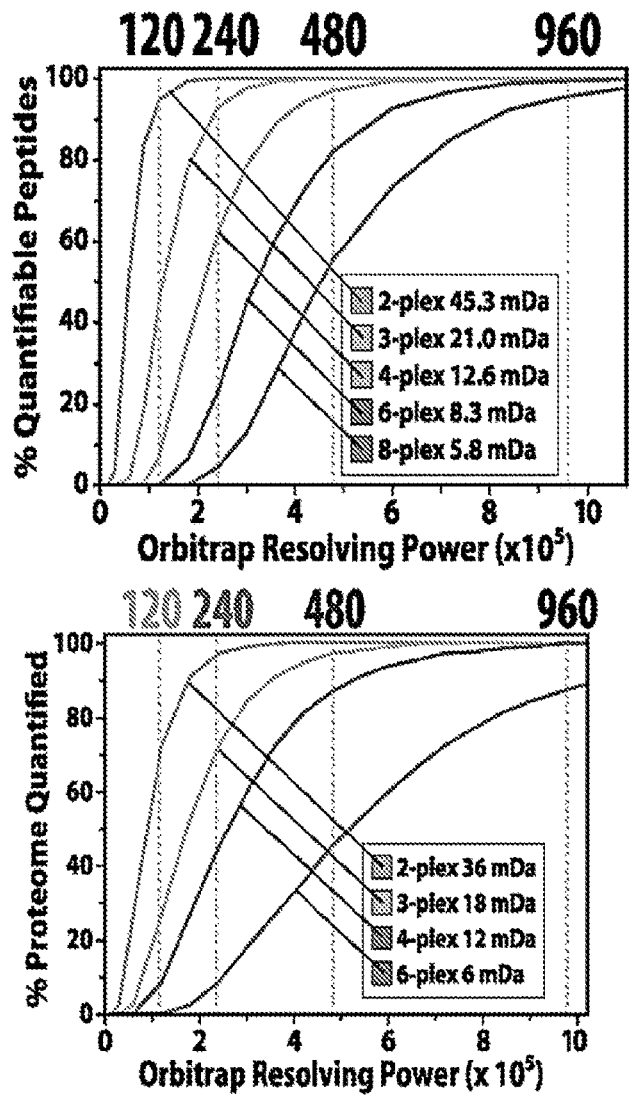

FIG. 6 shows a resolving power comparison between a DiPyrO$^6$-labeled yeast tryptic digest and a NeuCode SILAC yeast Lys-C digest.

Figure 7:
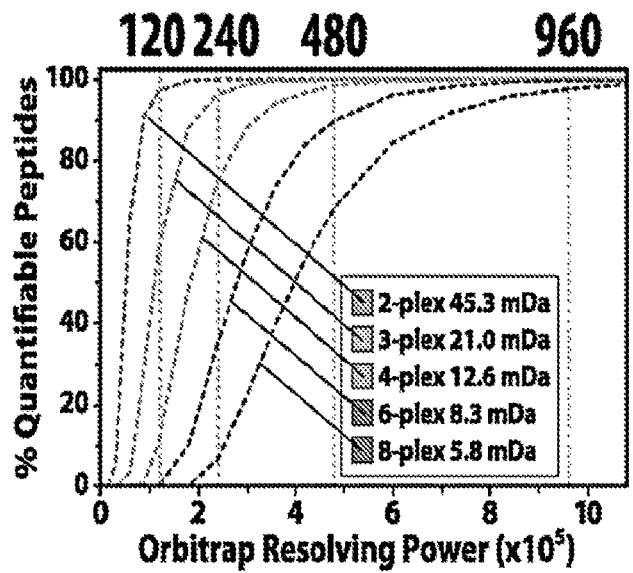
Figure 7:
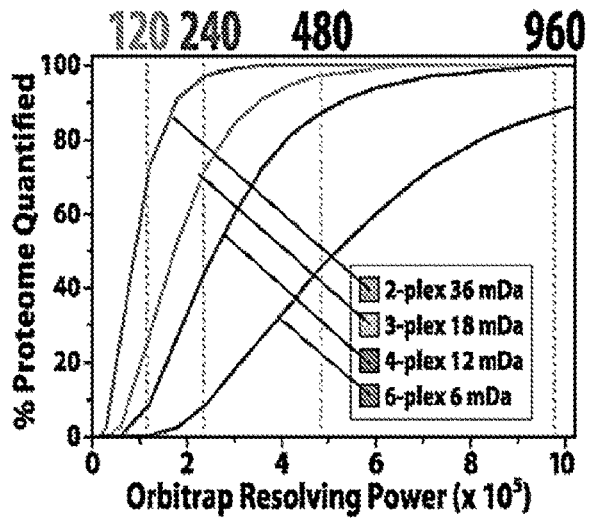

FIG. 7 shows a resolving power comparison between a DiPyrO$^6$-labeled yeast Lys-C digest and a NeuCode SILAC yeast Lys-C digest.

Figure 8:
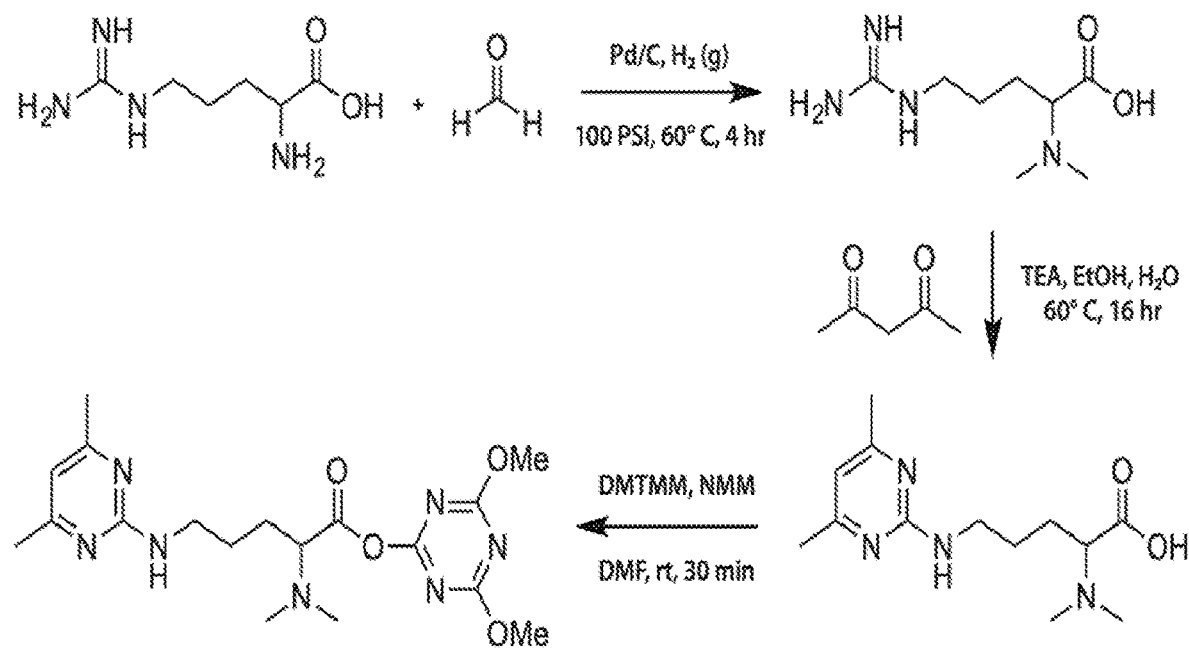

FIG. 8 illustrates the synthesis of a DiPyrO reagent in an embodiment of the invention. Arginine undergoes palladium-catalyzed dimethylation with formaldehyde in H$_2$ atmosphere followed by derivatization of the guanidino to a pyrimidine. The carboxylic acid is activated to the triazine ester to produce the DiPyrO labeling reagent.

Figure 9:
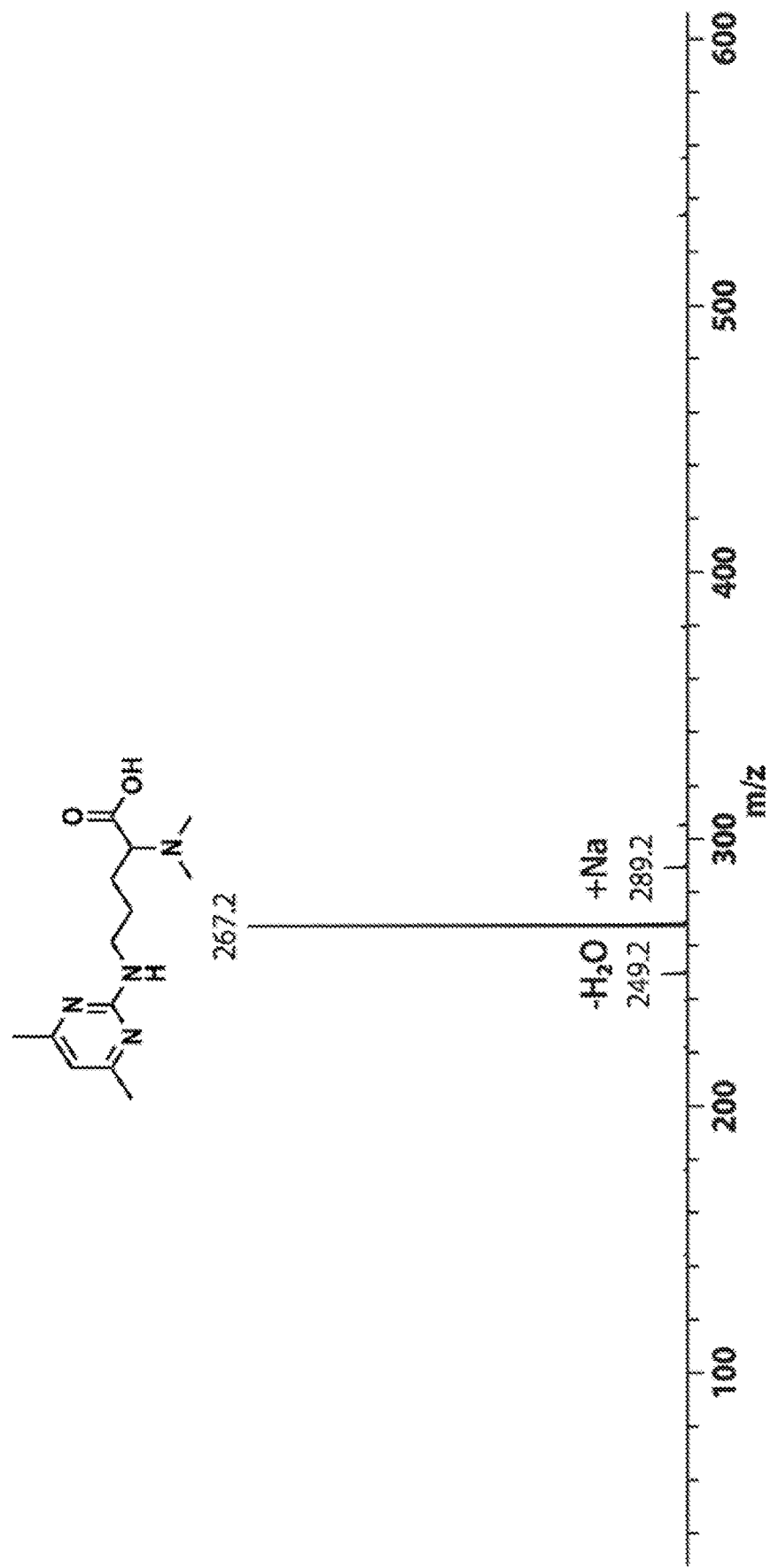

FIG. 9 shows a mass spectrum of an isolated DiPyrO tagging reagent following direct infusion MS of the synthesized DiPyrO tagging reagent. Following flash column chromatography, DiPyrO was recovered with high purity.

Figures 10A, 10B:
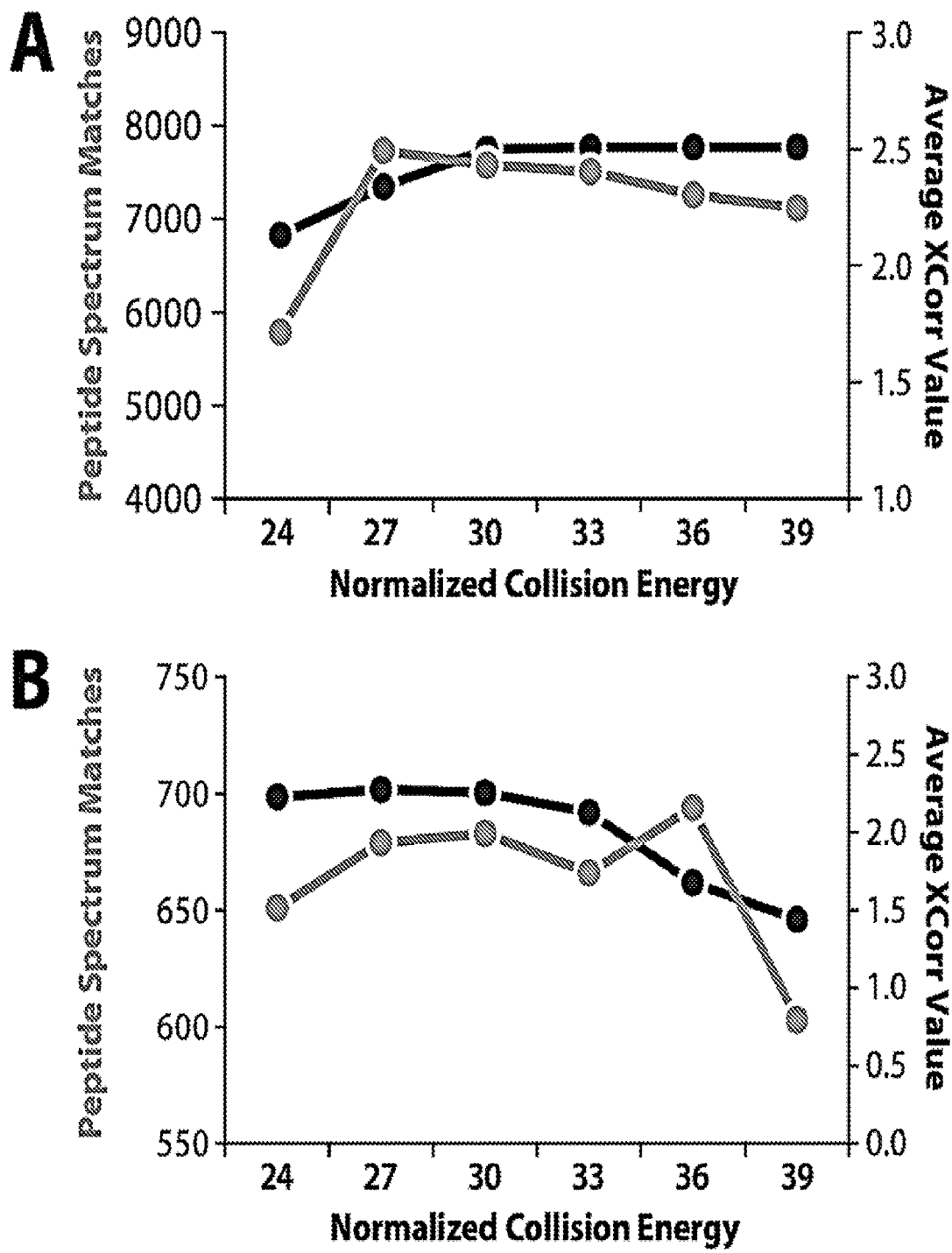

FIGS. 10A and 10B show HCD normalized collision energy optimization. DiPyrO-labeled yeast tryptic digest sample and bovine serum albumin (BSA) tryptic digest were analyzed via nanoLC-MS$^2$ with 120 min and 30 min elution gradients, respectively, on the Orbitrap Elite using (FIG. 10A) CID (for yeast) and (FIG. 10B) HCD (for BSA) with NCE values of 24, 27, 30, 33, 36, and 39. The number of identified peptide spectral matches (bottom line, in gray) and median XCorr values (top line, in black) were plotted as functions of NCE. An NCE of 29 or 30 was chosen for subsequent experiments based on the greater number of high-quality MS$^2$ spectra.

Figure 11:
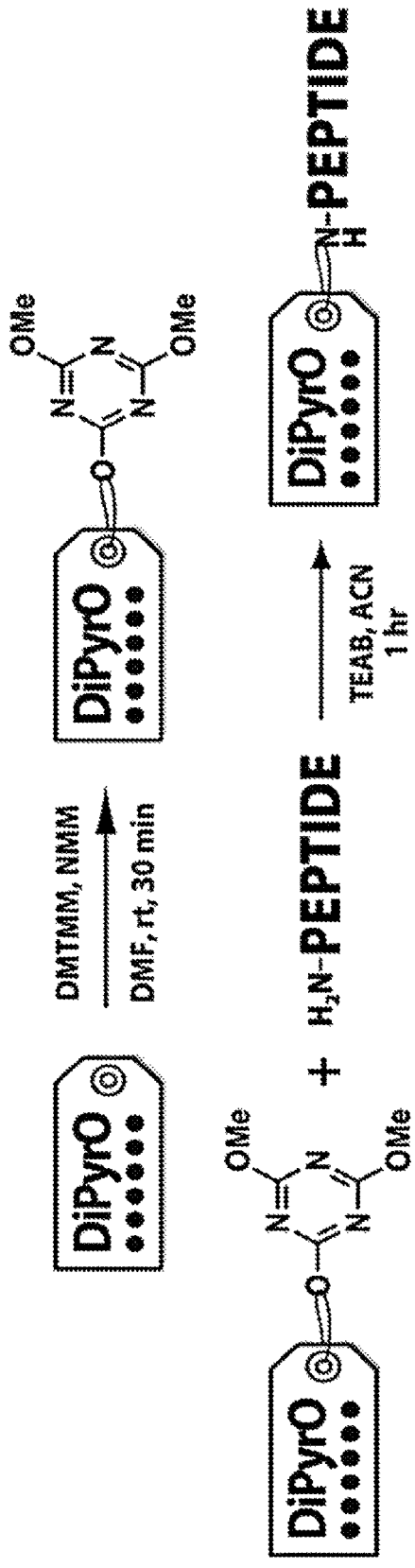

FIG. 11 provides labeling efficiency data at varying label to peptide ratios and for N-terminus labeling (N) and/or lysine labeling (K). The DiPyrO tags labeled trypsin- and Lys C-generated peptides with at least one tag with >99% efficiency at a label:peptide ratio of 50:1 (w/w) in 1 hr. Trypsin- and Lys C-generated peptides containing lysine were labeled with two tags, at both the N-terminus and lysine residue, with 99% and 94% efficiency, respectively.

Figures 12A, 12B, 12C:
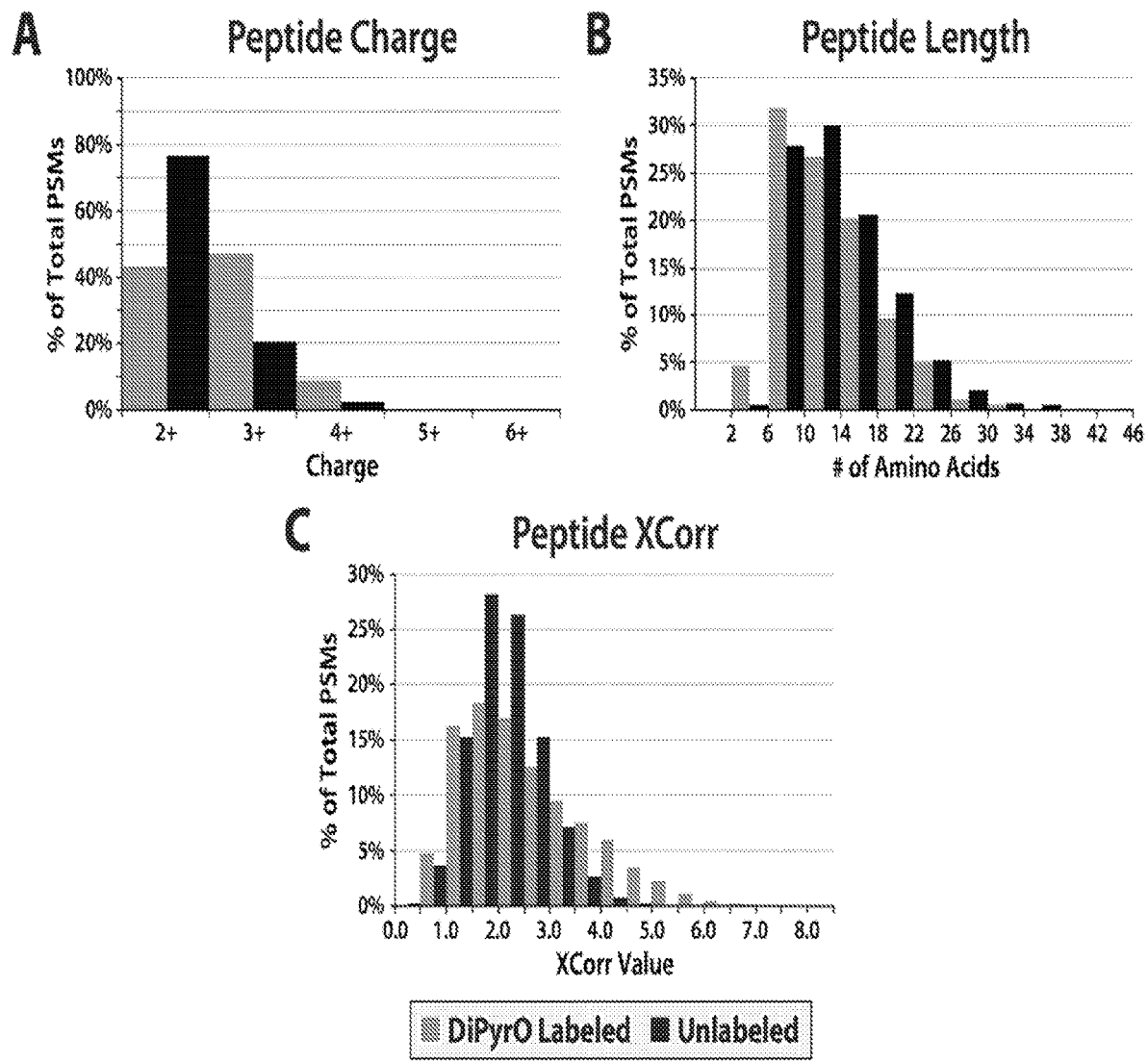

FIGS. 12A-12C show the effects of DiPyrO labeling on peptide identification. DiPyrO-labeled and unlabeled yeast tryptic digest samples were analyzed via nanoLC-MS$^2$ on the Orbitrap Elite using HCD fragmentation (NCE 29 and 35, respectively). The distribution of peptide charge state (FIG. 12A), peptide length (FIG. 12B), and XCorr (FIG. 11C) values of the labeled PSMs from the labeled sample were plotted against those from the unlabeled sample.

Figure 13:
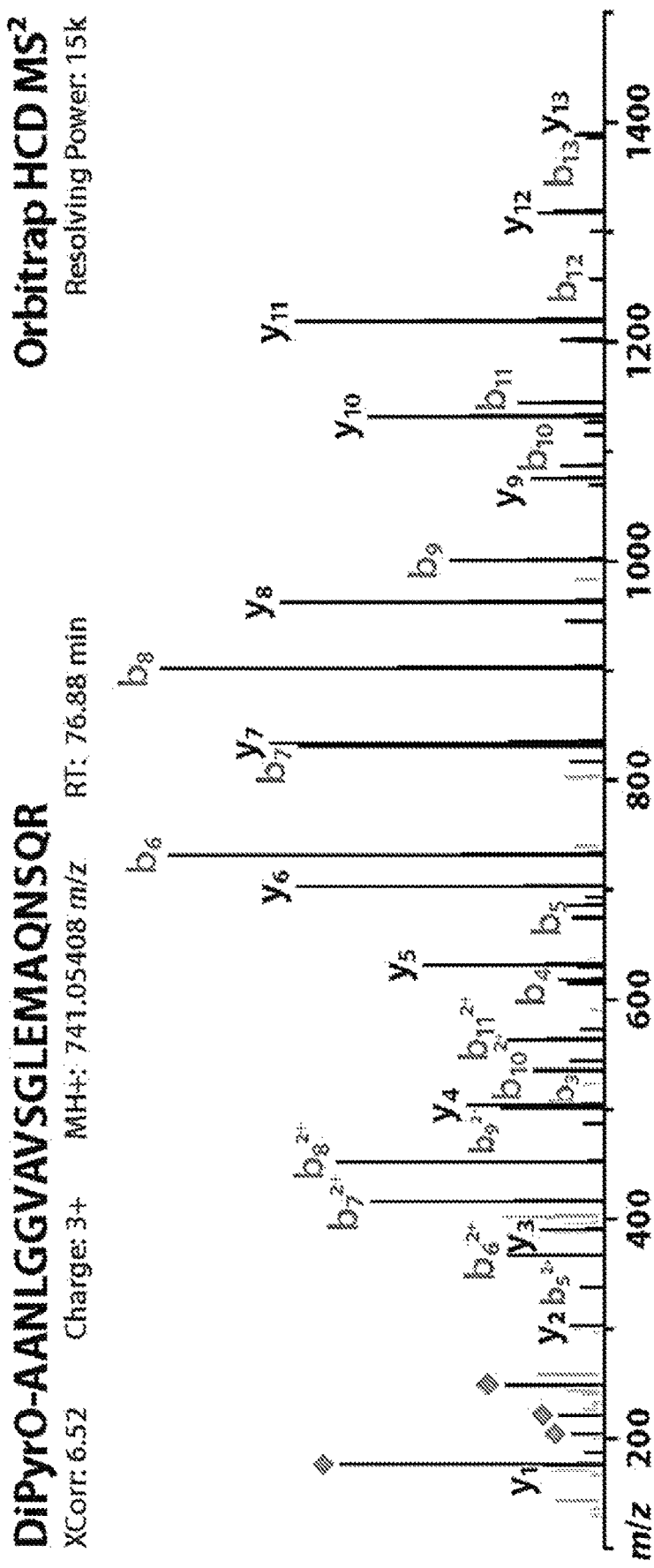

FIG. 13 shows an MS$^2$ spectrum of a DiPyrO-labeled yeast tryptic peptide acquired in the Orbitrap following HCD fragmentation (NCE 29). A wealth of b- and y-ions are observed for confident peptide sequence identification. Signature ions in the low mass region produced by fragmentation of the DiPyrO tag are marked by diamonds.

Figure 14A:
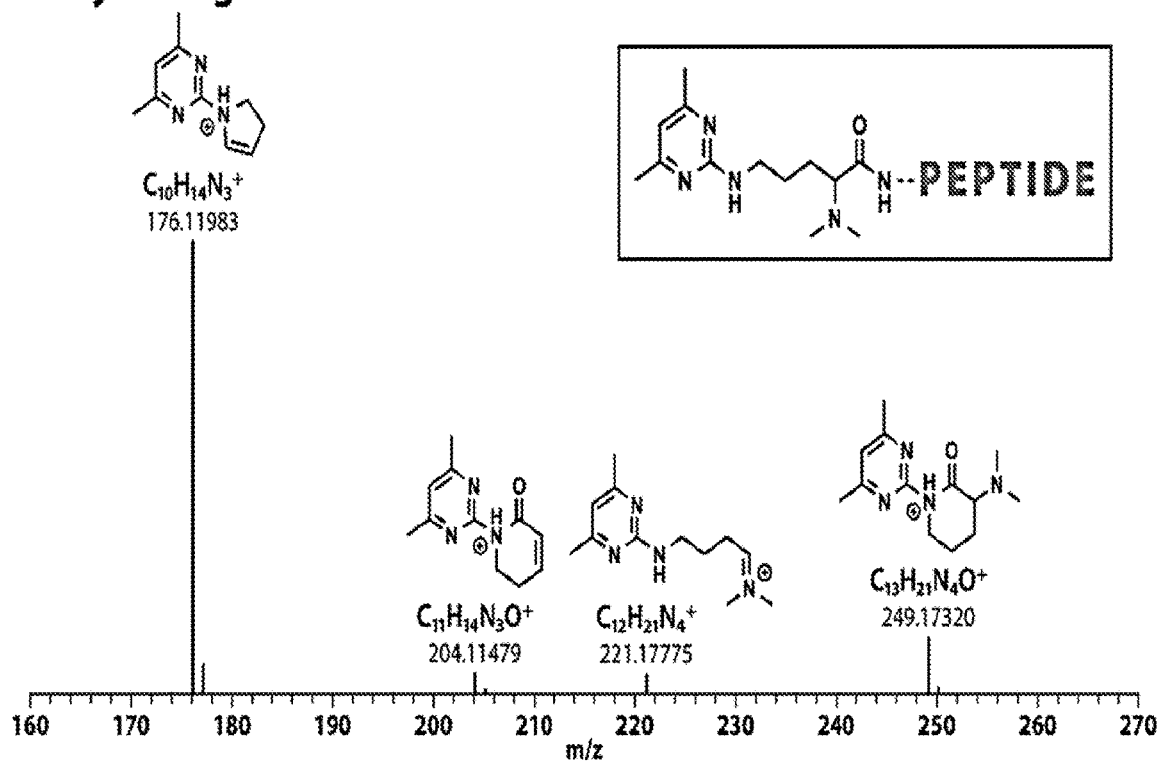
Figure 14B:
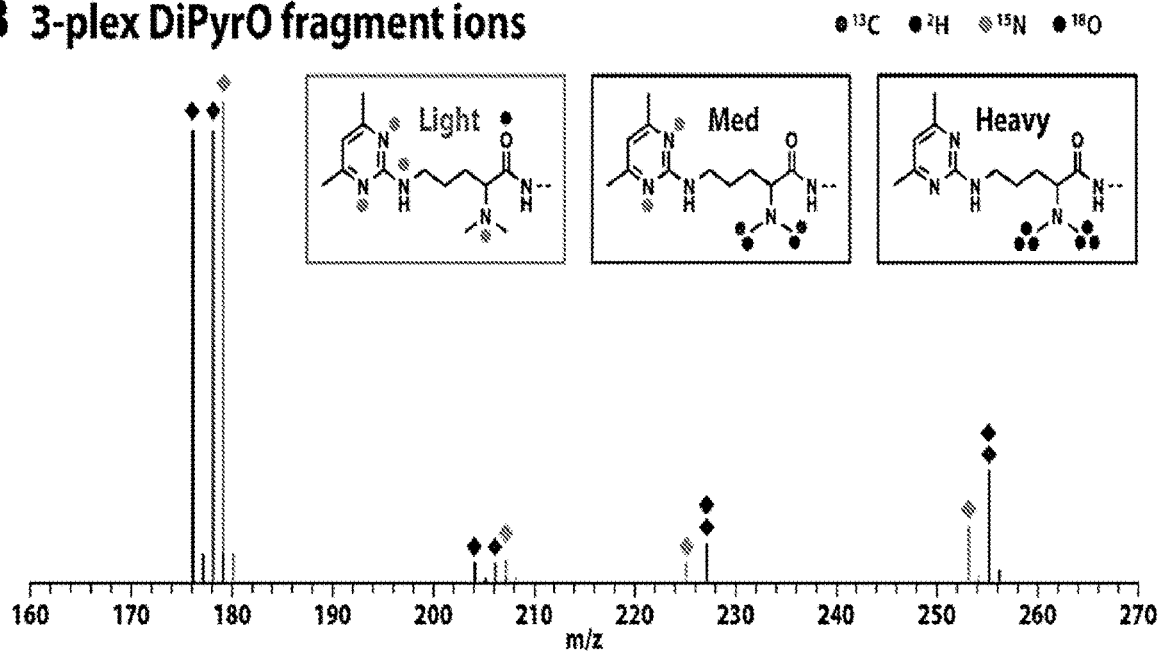

FIGS. 14A and 14B show characteristic DiPyrO fragment ions (FIG. 14A). Collision-induced dissociation of DiPyrO-labeled peptides produces four characteristic 'reporter' ions in the low mass region of MS$^2$ spectra. Based on the measured masses of the ions, potential structures are shown (FIG. 14B). A theoretical MS$^2$ spectra illustrates that the 3-plex DiPyrO$^6$ mass defect isotopologues give rise to additional ions, resulting in four clusters of ions.

Figure 15:
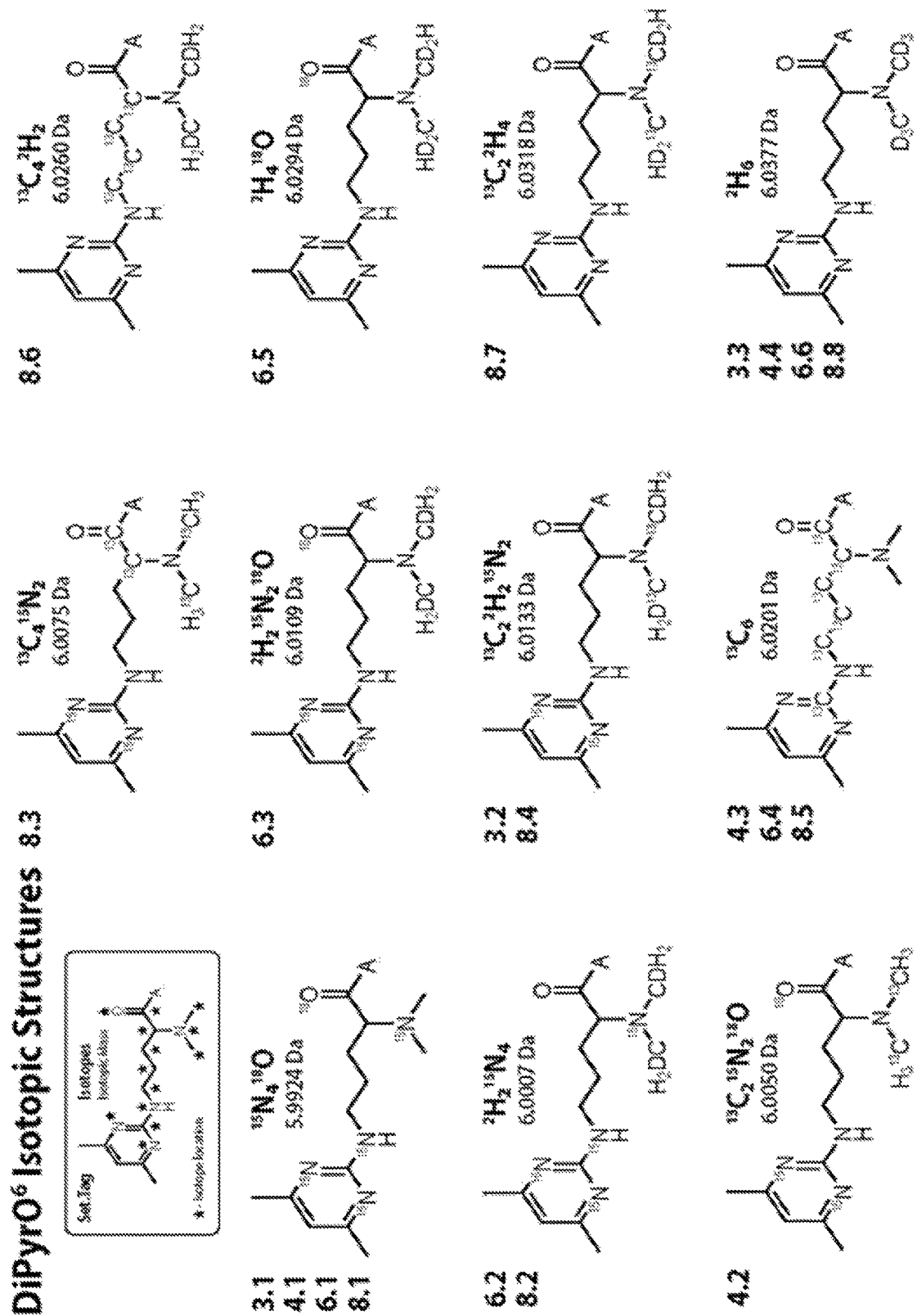

FIG. 15 illustrates exemplary DiPyrO$^6$ isotopic structures with isotopic positions for each isotopologue that make up various multiplex sets in an embodiment of the invention. These exemplary structures are not exhaustive and additional isotopic combinations are available.

Figure 16:
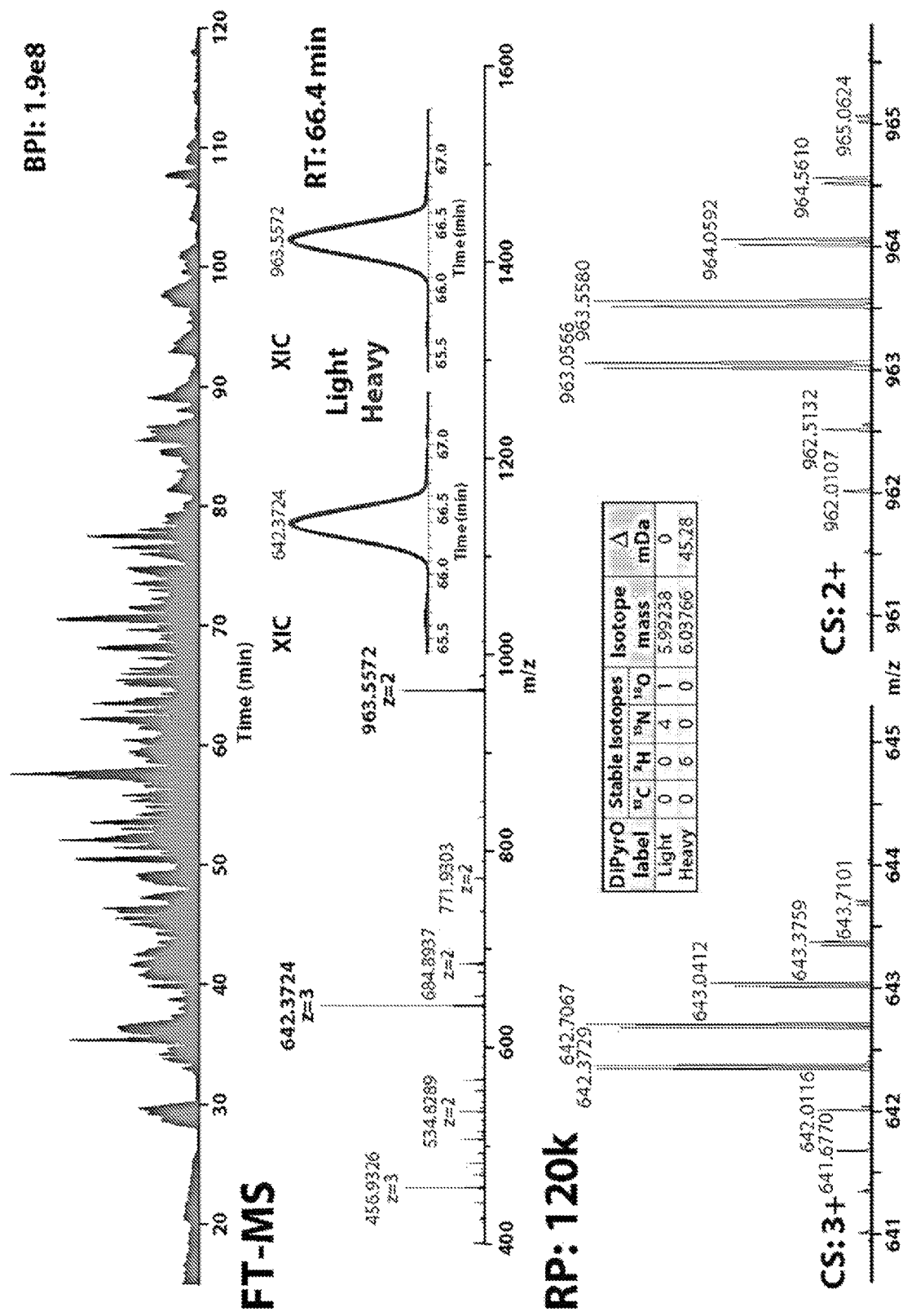

FIG. 16 shows data from a yeast tryptic digest sample labeled in duplex with a light DiPyrO$_{0041}$ ($^{15}$N$_4$$^{18}$O) tag and a heavy DiPyrO$_{0600}$ ($^2$H$_6$) tag, combined, and analyzed via nanoLC-MS$^2$ on an Orbitrap Elite system using a 120 minute elution gradient. An FT-MS scan acquired in the Orbitrap mass analyzer at a resolving power (RP) of 120 k at retention time (RT)=66.4 minutes is also shown along with the extracted ion chromatograms of a DiPyrO-labeled peptide detected with charge state 2+ and 3+ at m/z 642 and 963. The isotopic peak clusters showing baseline-resolved peaks for the light- and heavy-labeled samples are also shown in addition to the base peak ion (BPI) chromatogram.

Figure 17:
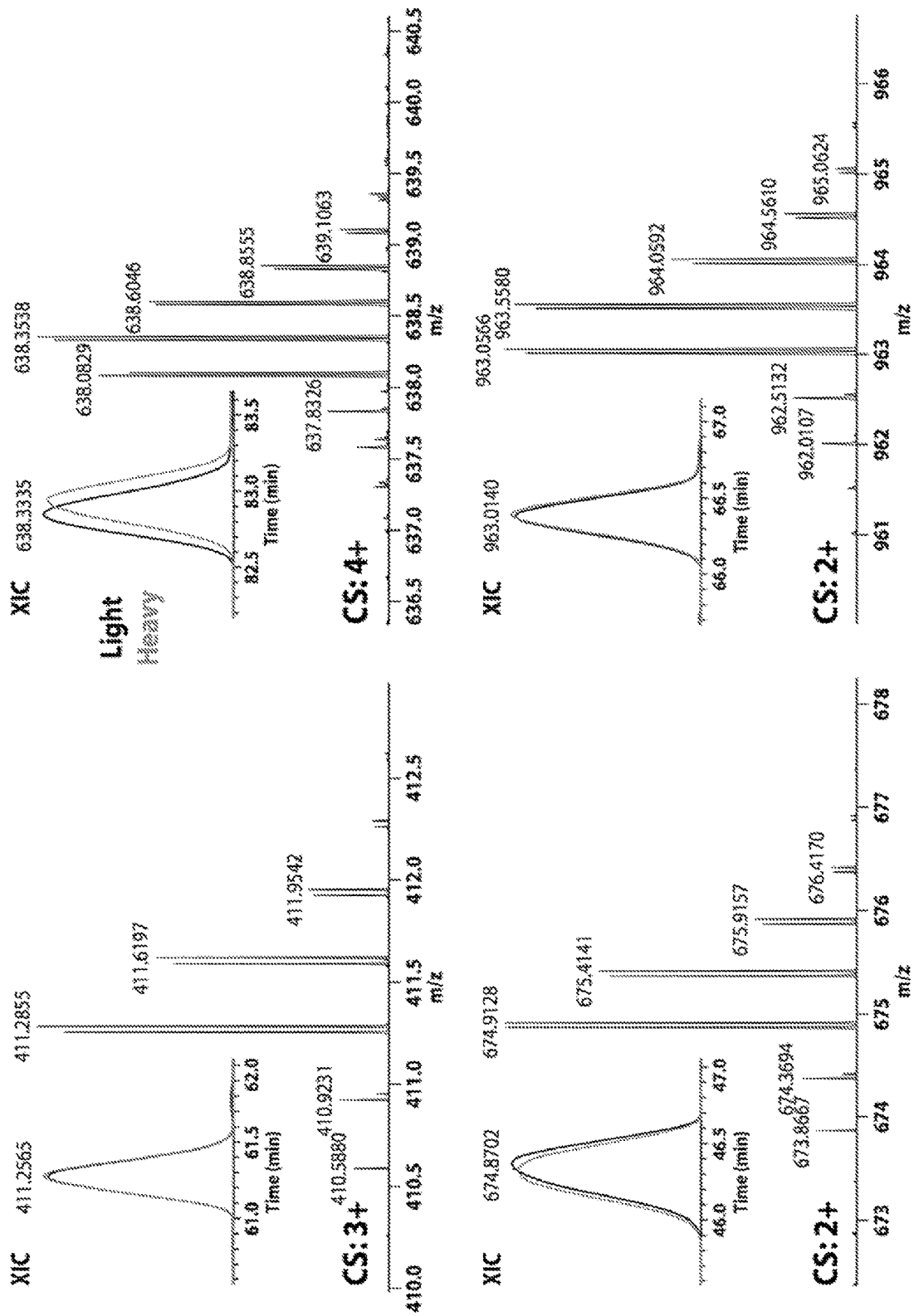

FIG. 17 shows extracted ion chromatograms of several 2-plex DiPyrO$^6$-labeled peptides detected in FIG. 16 alongside the peptides' isotopic peak clusters, showing baseline-resolved peaks for the light- and heavy-labeled samples.

Figure 18:
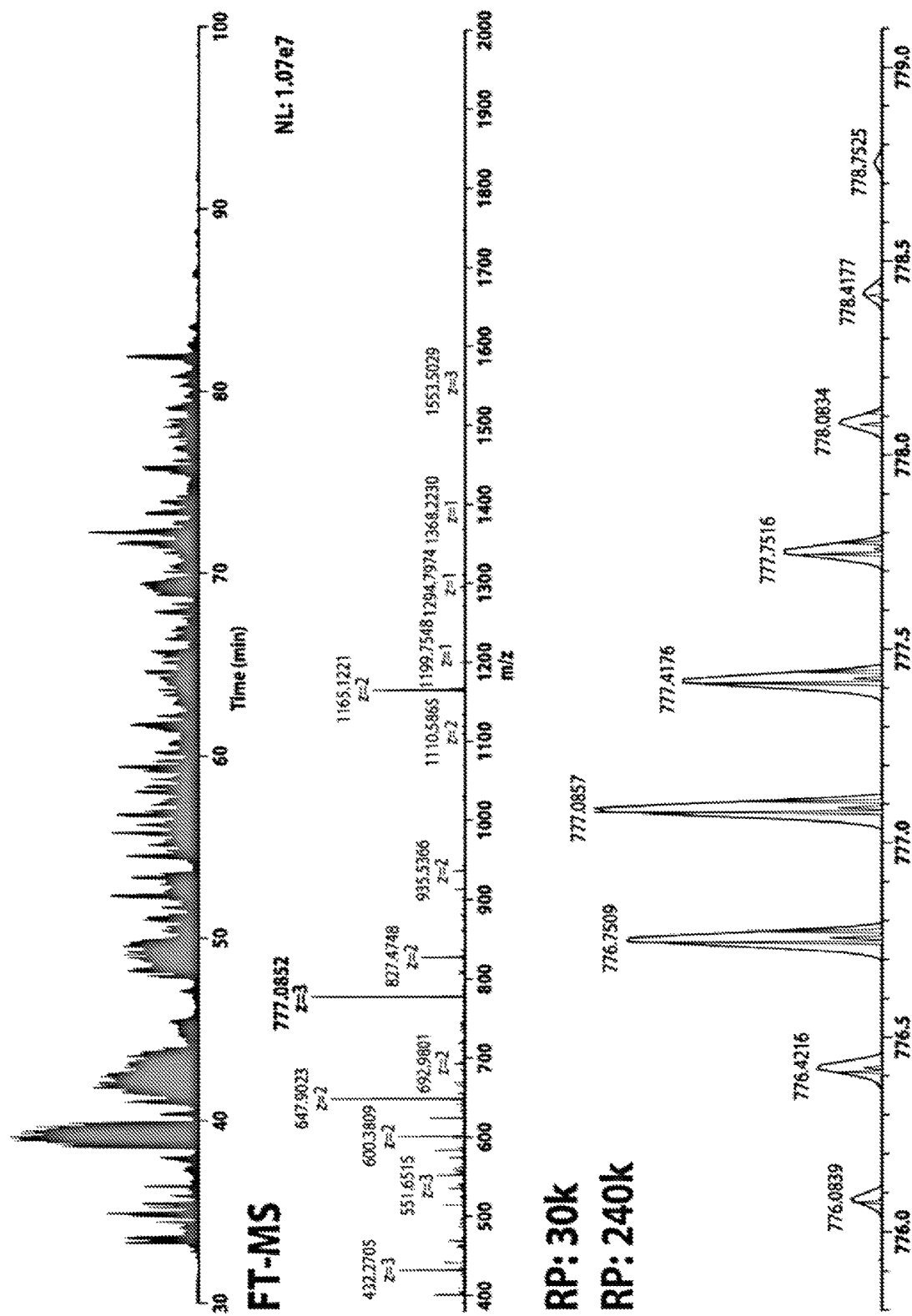

FIG. 18 shows data from a yeast tryptic digest sample labeled in triplex with a light DiPyrO$_{0041}$ ($^{15}$N$_4$$^{18}$O) tag, medium DiPyrO$_{2220}$ ($^{13}$C$_2$$^2$H$_2$$^{15}$N$_2$) tag and heavy DiPyrO$_{0600}$ ($^2$H$_6$) tag, combined, and analyzed via nanoLC-MS$^2$ on an Orbitrap Elite system using a 120 minute elution gradient. The BPI chromatogram is shown along with an FT-MS scan acquired in the Orbitrap mass analyzer. The isotopic peak clusters of a peptide at m/z 777 detected in back-to-back FT-MS scans at RP 30 k and RP 240 k are also shown. The differentially labeled peptide samples are indistinguishable at 30 k, but are evident at 240 k, enabling quantification by comparison of the three peaks arising from the light, medium, and heavy DiPyrO$^6$-labeled samples.

Figure 19:
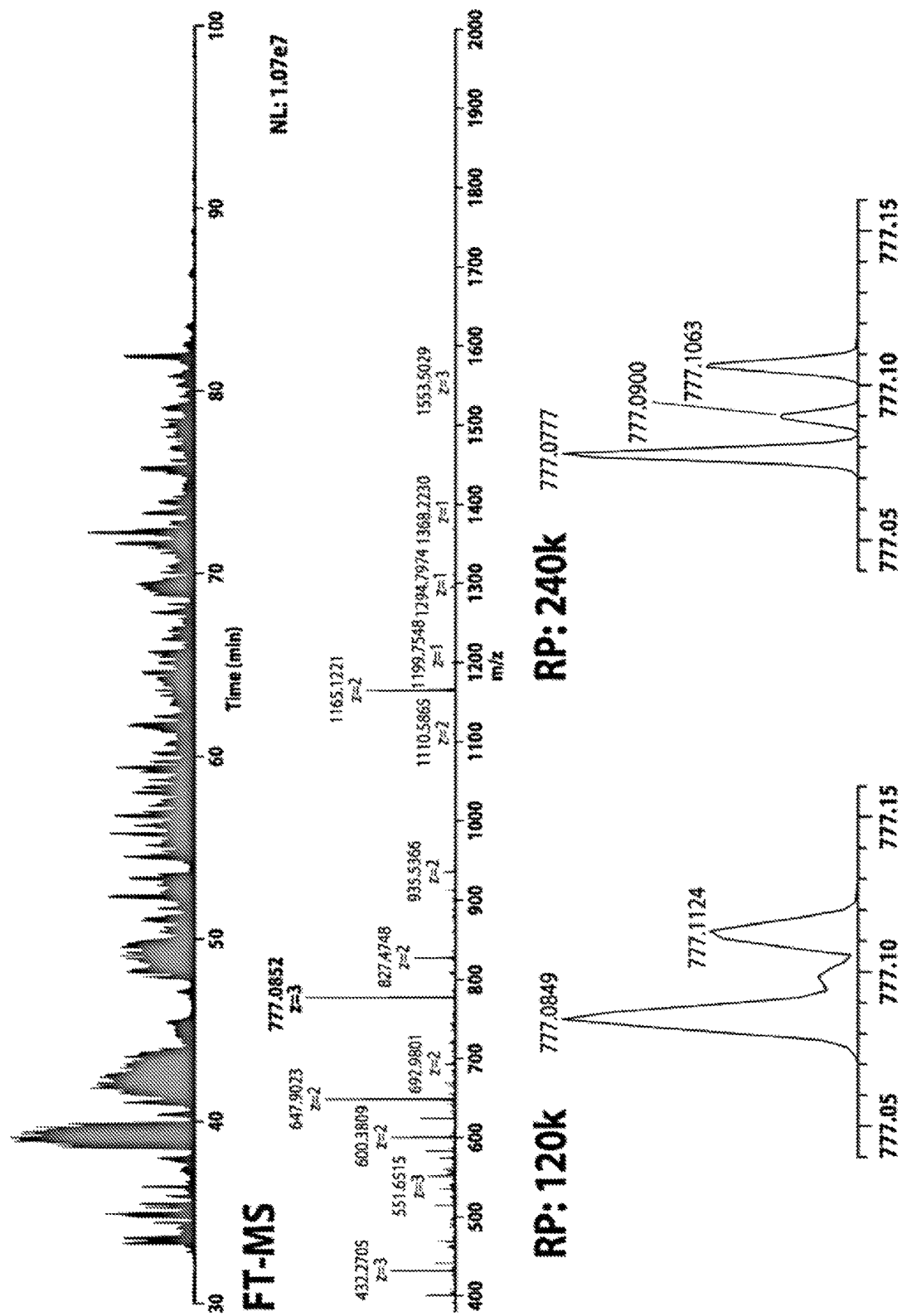

FIG. 19 shows the 3-plex DiPyrO$^6$-labeled peptide peaks of FIG. 18 at m/z 777 which are baseline resolved at 240 k, but not at 120 k. This peptide was detected with a 3+ charge state and is labeled with a single DiPyrO tag at the N-terminus.

Figure 20:
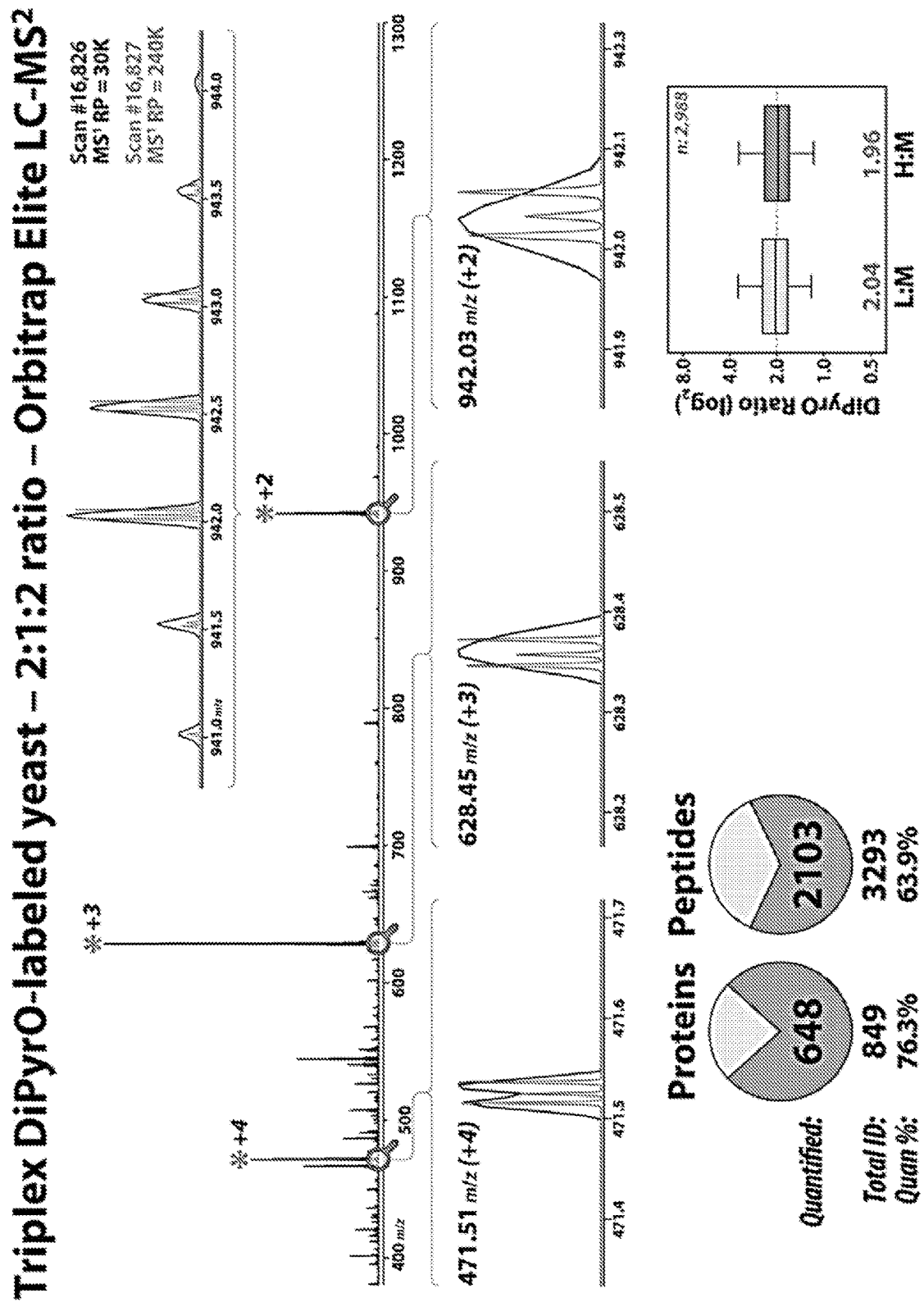

FIG. 20 shows data from a yeast sample labeled in triplex with a light DiPyrO$_{0041}$ ($^{15}$N$_4$$^{18}$O) tag, medium DiPyrO$_{2220}$ ($^{13}$C$_2$$^2$H$_2$$^{15}$N$_2$) tag and heavy DiPyrO$_{0600}$ ($^2$H$_6$) tag in a 2:1:2 ratio, respectively, and analyzed via LC-MS on an Orbitrap Elite system. Isotopic peak clusters of peptides at m/z 471, 628, and 942 detected in back-to-back FT-MS scans at RP 30 k and RP 240 k are shown. The differentially labeled peptide samples are indistinguishable at RP 30 k, but are evident at 240 k, enabling quantification by comparison of the three peaks arising from the light, medium, and heavy DiPyrO$^6$-labeled samples. Over 76% of proteins and 63% of peptides of the identified yeast proteome were successfully quantified using the triplex DiPyrO tags.

Figure 21:
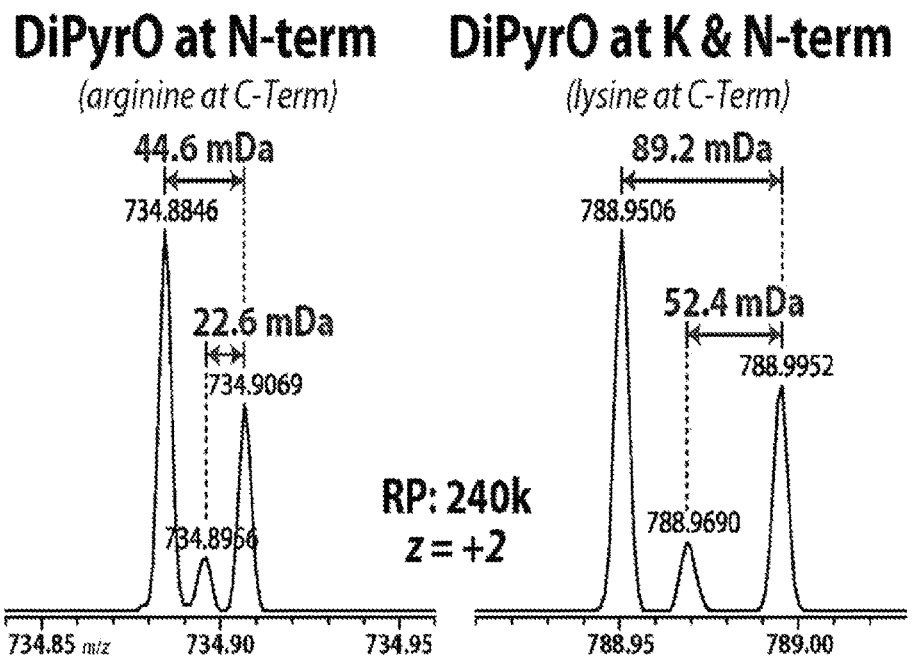

FIG. 21 shows a comparison between a 3-plex DiPyrO$^6$-labeled tryptic peptide carrying a single DiPyrO tag with a tryptic peptide carrying two DiPyrO tags. A tryptic peptide with an N-terminal amine and a C-terminal arginine (R)

residue carries a single tag, while a peptide with an N-terminal amine and a C-terminal lysine (K) residue, with side-chain amine, carries two tags and is more readily baseline resolved at 240 k. Doubling the mass defect difference between channels with two tags can enable higher orders of multiplexed analysis at lower resolving powers.

FIG. 22 shows the combination of 2-plex DiPyrO$^2$, 3-plex DiPyrO$^6$, and 4-plex DiPyrO$^{10}$ sets that enables 9-plex quantification at RP 240 k. The increase in multiplexing is achieved via three clusters, spaced 4 Da apart, of mass defect-based quantitative channels.

Figure 23:
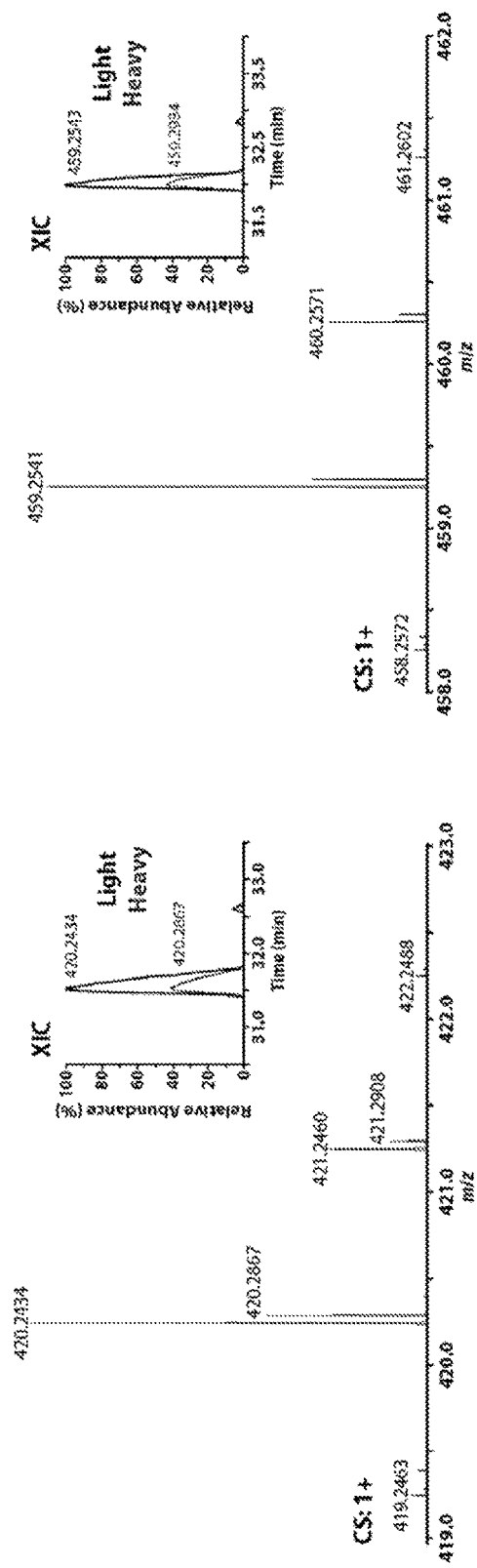
Figure 23:
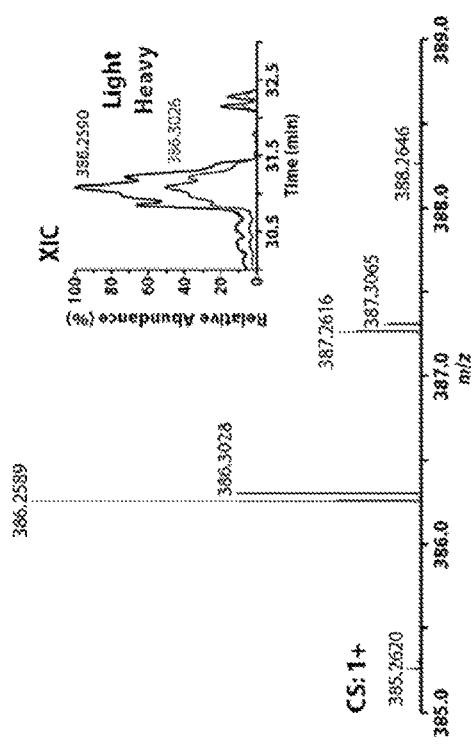

FIG. 23 shows data from an amine-containing metabolite standard mixture sample containing the amino acids phenylalanine (165.0790 Da), tryptophan (204.0899 Da), and leucine/isoleucine (131.0946 Da) labeled in duplex with a light DiPyrO$_{0041}$ ($^{15}$N$_4$$^{18}$O; +254.1561) tag and a heavy DiPyrO$_{0600}$ ($^2$H$_6$; +254.20138) tag, combined at a 2:1 ratio, and analyzed via nanoLC-MS$^2$ on an Orbitrap Elite system using a 30 minute elution gradient. FT-MS scans acquired in the Orbitrap mass analyzer at RP 120 k are shown along with the extracted ion chromatograms of each DiPyrO-labeled amino acid detected with charge state 1+ at m/z 420, 459, and 386. The isotopic peak clusters show baseline-resolved peaks for the light- and heavy-labeled samples.

Figure 24:
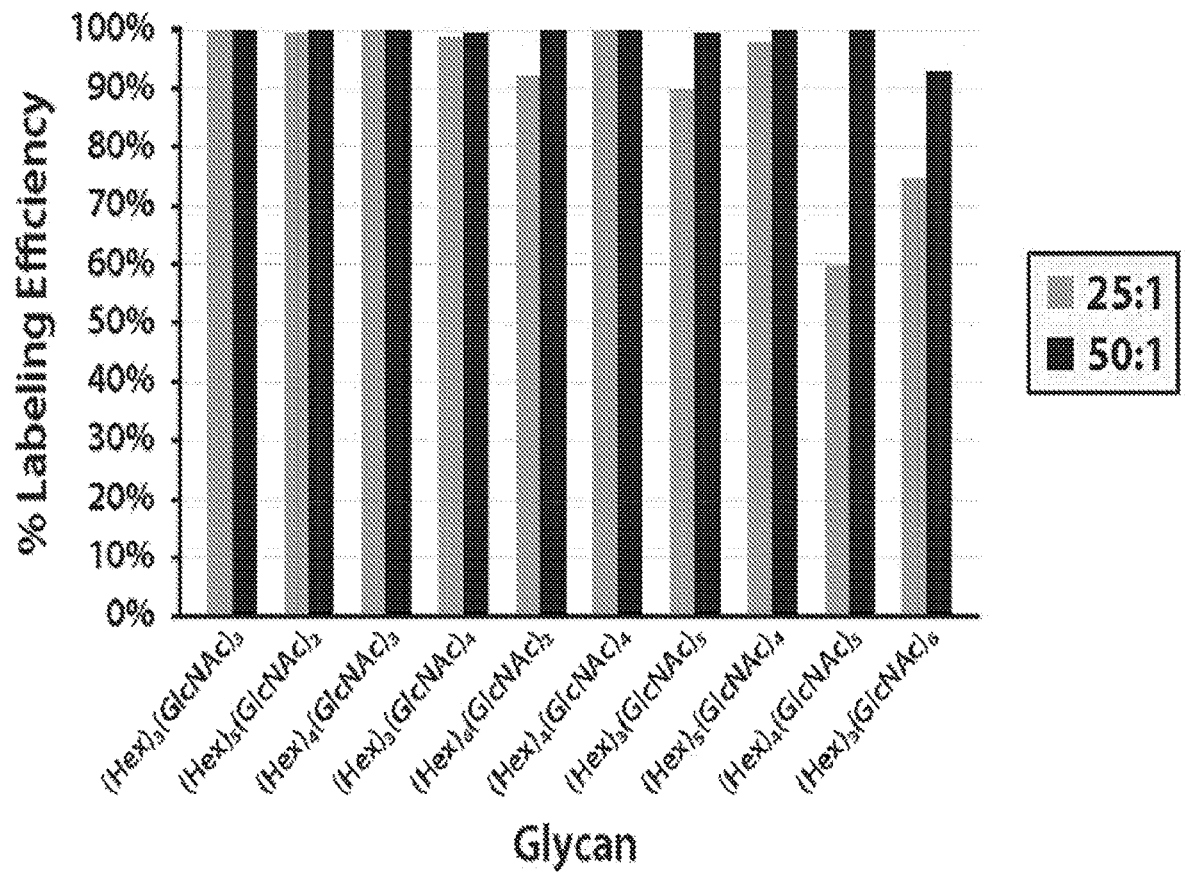

FIG. 24 shows the labeling efficiencies of PNGaseF-released N-glycosylamines that were dried in vacuo, labeled with a nonisotopic DiPyrO tag (in dry DMF) at 25:1 and 50:1 tag to glycoprotein ratio (by weight), and analyzed on a MALDI Orbitrap LTQ XL system. Labeling efficiency % was calculated by dividing the signal intensity of the labeled glycan peak by the combined intensity of the labeled and unlabeled glycan peak (if present). A labeling efficiency of >98% is observed for all but one glycan structure at a 50:1 ratio.

Figure 25:
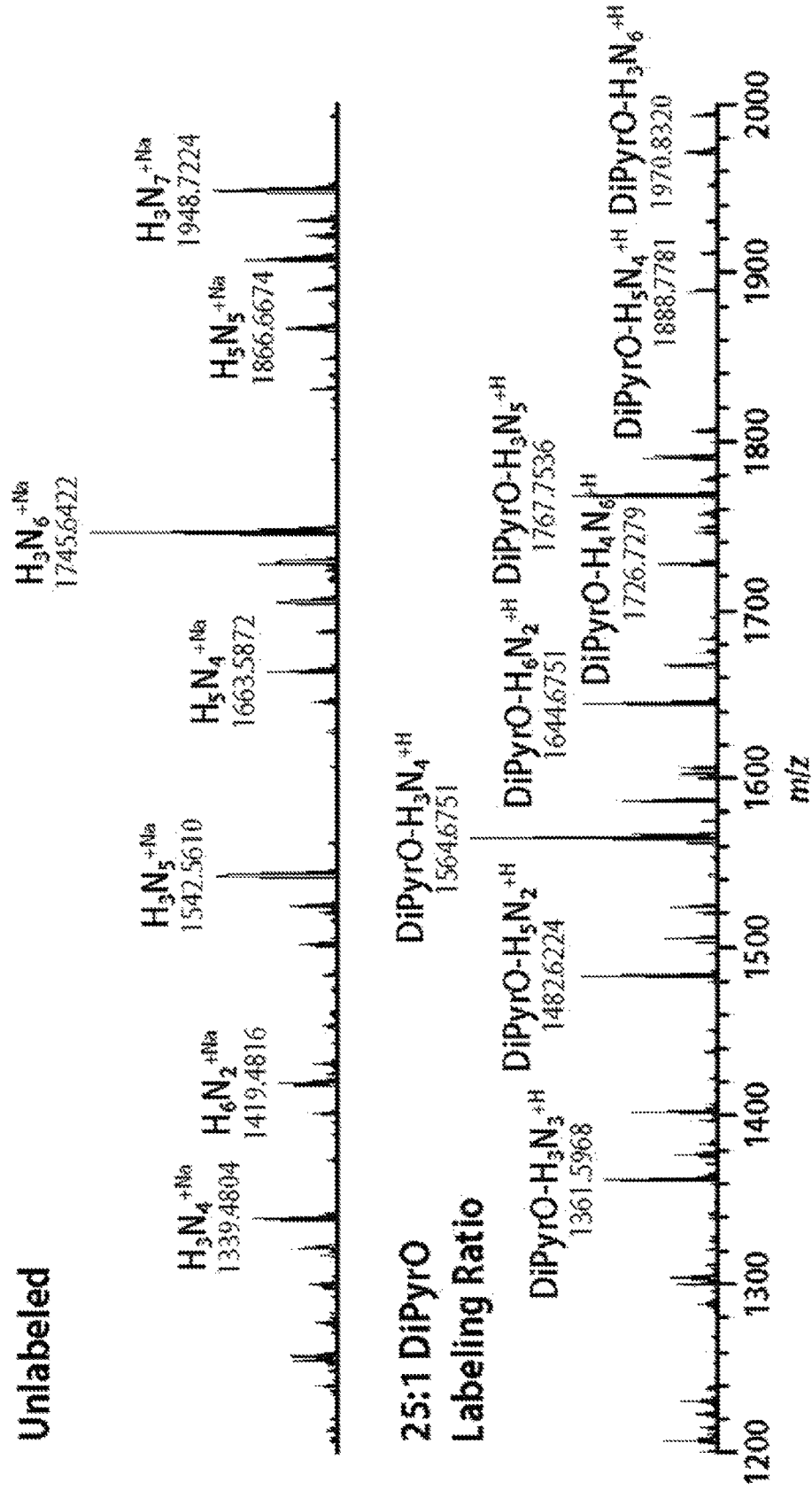

FIG. 25 shows a MALDI-MS spectra of abundant unlabeled and DiPyrO-labeled glycans (released by PNGaseF from Ovalbumin) detected in the mass range of m/z 1200-2000.

Figure 26A:
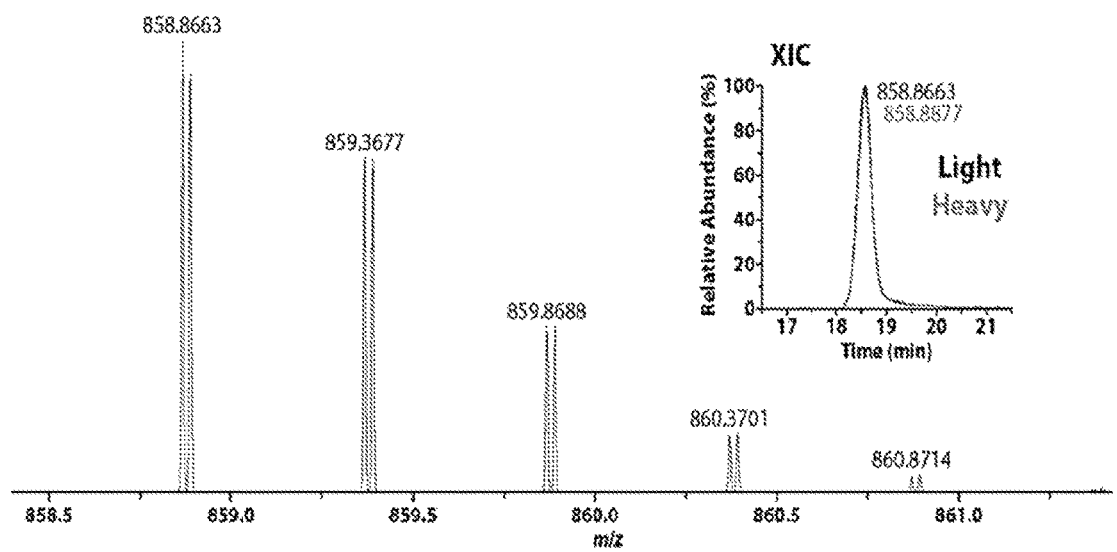
Figure 26B:
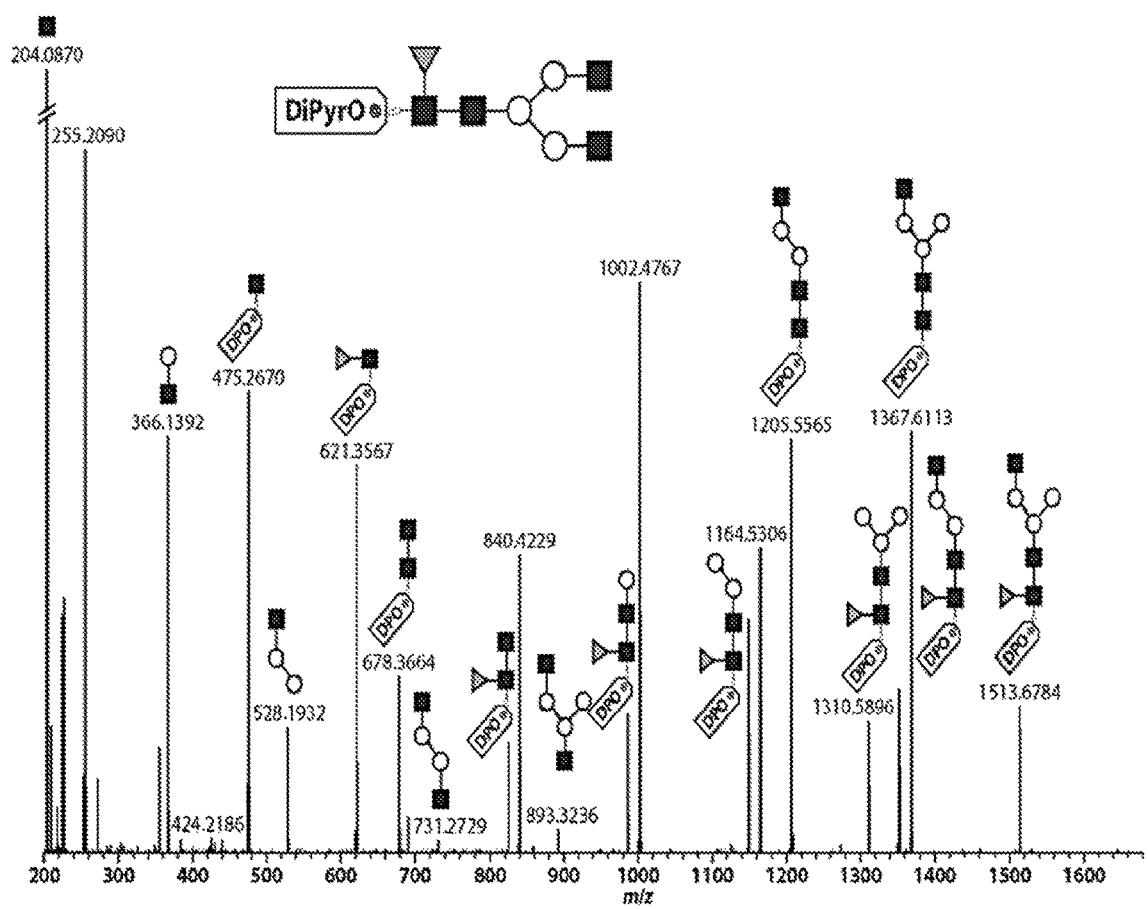

FIG. 26A shows the precursor ion doublet of a duplex DiPyrO$^6$-labeled glycan at m/z 858.9 acquired in the Orbitrap mass analyzer at RP 240 k along with the extracted ion chromatograms of the light- and heavy-labeled species. The isotopic peak cluster shows baseline-resolved peaks for the light- and heavy-labeled species. FIG. 26B shows an annotate MS$^2$ spectrum of a duplex DiPyrO$^6$-labeled glycan at m/z 858.9 acquired in the Orbitrap following HCD fragmentation (NCE 27). A complete set of fragment ions are observed for confident structural identification of the DiPyrO-labeled glycan.

Figure 27:
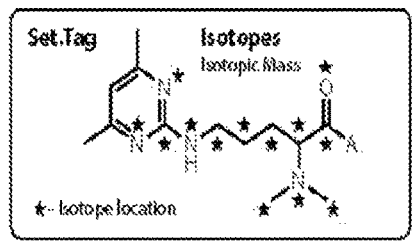
Figure 27:
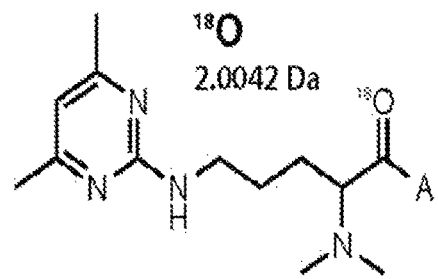
Figure 27:
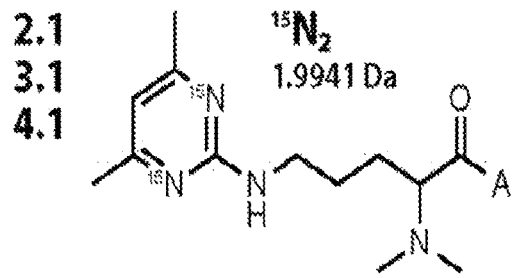
Figure 27:
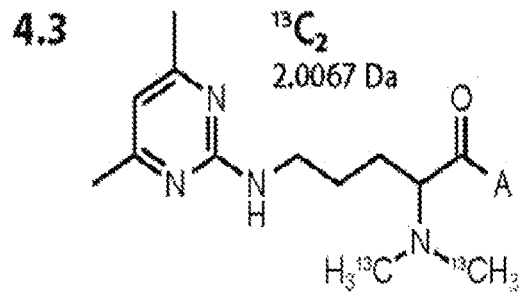
Figure 27:
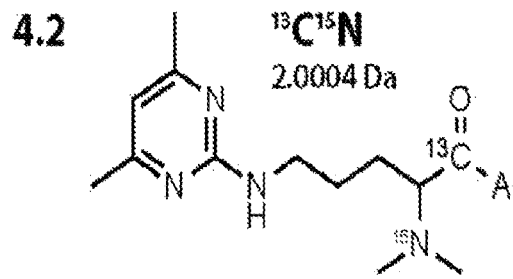
Figure 27:
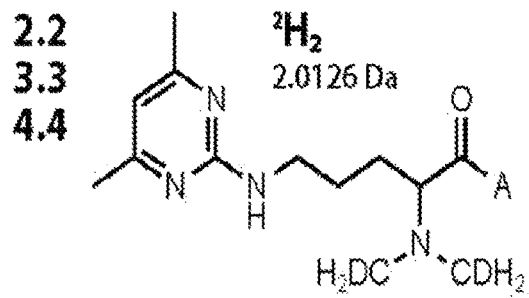

FIG. 27 illustrates exemplary DiPyrO$^2$ isotopic structures with isotopic positions for each isotopologue that make up various multiplex sets in an additional embodiment of the invention. These exemplary structures are not exhaustive and additional isotopic combinations are available.

Figure 28:
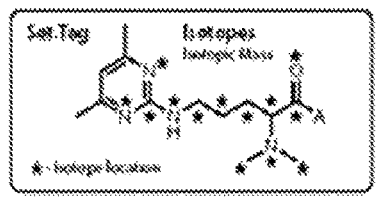
Figure 28:
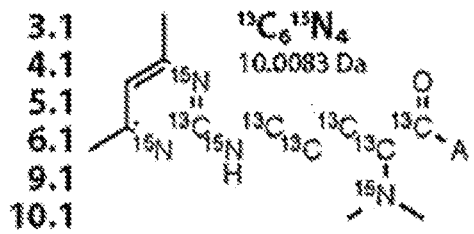
Figure 28:
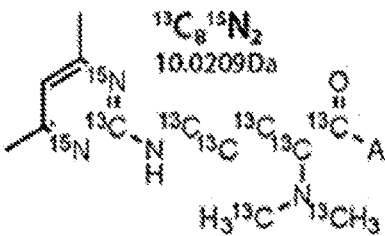
Figure 28:
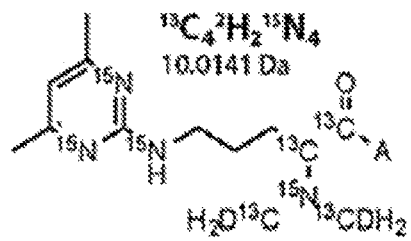
Figure 28:
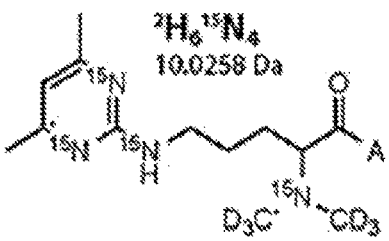
Figure 28:
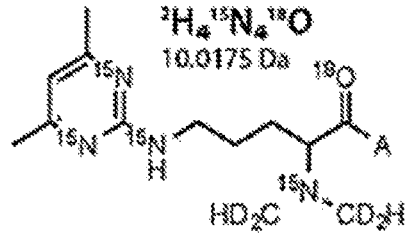
Figure 28:
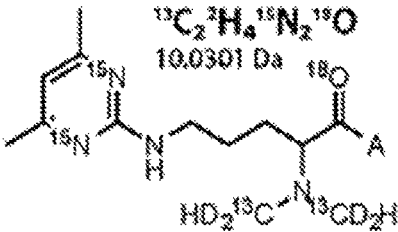
Figure 28:
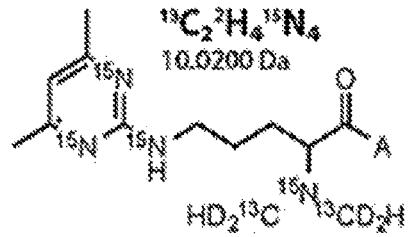
Figure 28:
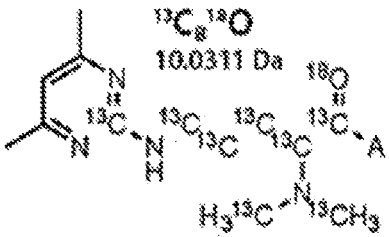
Figure 28:
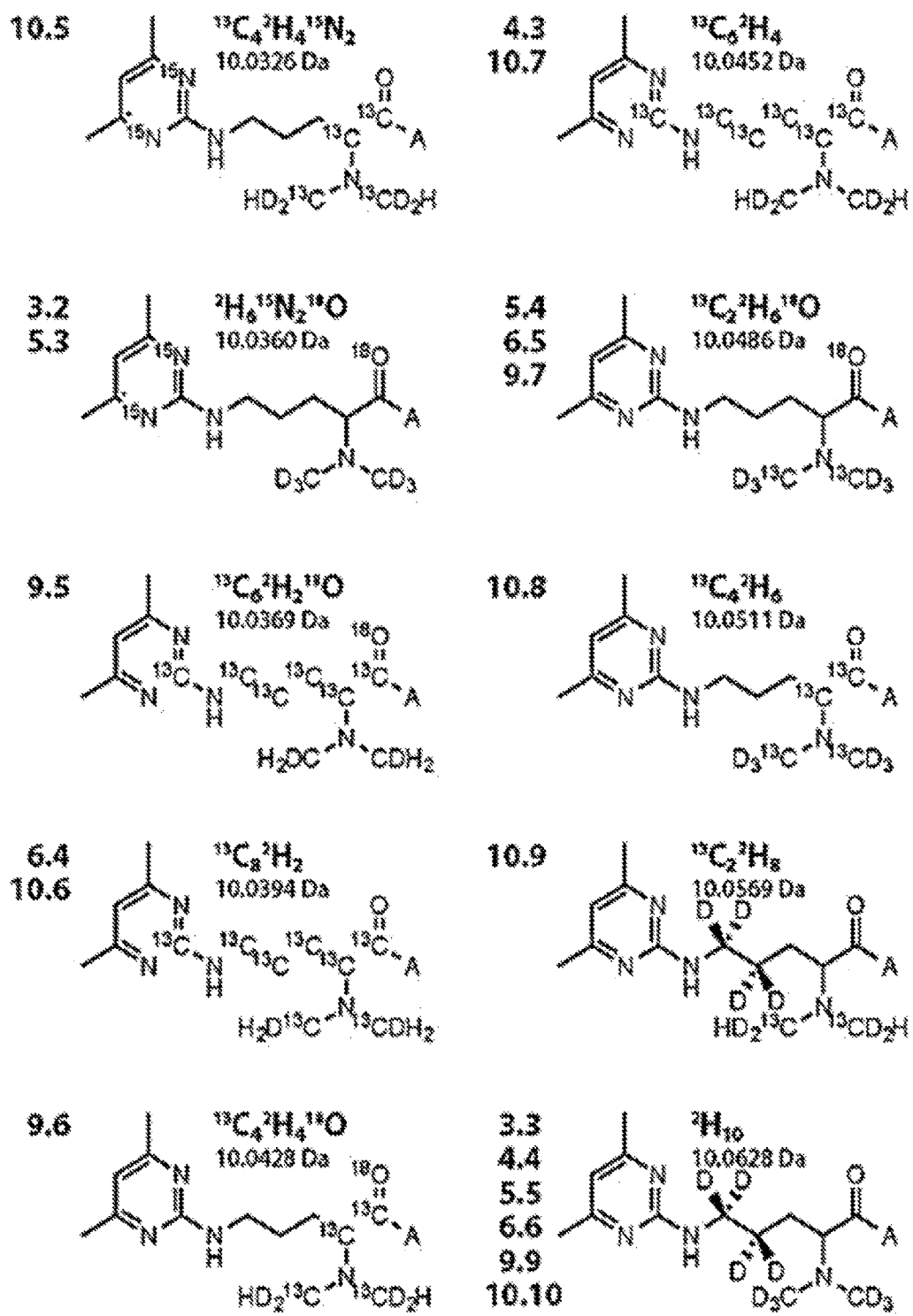

FIG. 28 illustrates exemplary DiPyrO$^{10}$ isotopic structures with isotopic positions for each isotopologue that make up various multiplex sets in an additional embodiment of the invention. These exemplary structures are not exhaustive and additional isotopic combinations are available.

DETAILED DESCRIPTION OF THE INVENTION

Definitions

In general, the terms and phrases used herein have their art-recognized meaning, which can be found by reference to standard texts, journal references and contexts known to those skilled in the art. The following definitions are provided to clarify their specific use in the context of the invention.

In an embodiment, a composition or compound of the invention, such as an isotopically enriched compound including isotopically labeled analytes, isotopic tagging reagents, isotopically labeled amino acids, isotopically labeled standards and/or isotopically labeled peptides or proteins, is isolated or purified. In an embodiment, an isolated or purified compound is at least partially isolated or purified as would be understood in the art. In an embodiment, a composition or compound of the invention has a chemical purity of 90%, optionally for some applications 95%, optionally for some applications 99%, optionally for some applications 99.9%, optionally for some applications 99.99%, and optionally for some applications 99.999% pure.

Many of the molecules disclosed herein contain one or more ionizable groups. Ionizable groups include groups from which a proton can be removed (e.g., —COOH) or added (e.g., amines) and groups which can be quaternized (e.g., amines). All possible ionic forms of such molecules and salts thereof are intended to be included individually in the disclosure herein. With regard to salts of the compounds herein, one of ordinary skill in the art can select from among a wide variety of available counterions that are appropriate for preparation of salts of this invention for a given application. In specific applications, the selection of a given anion or cation for preparation of a salt can result in increased or decreased solubility of that salt.

The compounds of this invention can contain one or more chiral centers. Accordingly, this invention is intended to include racemic mixtures, diasteromers, enantiomers, tautomers and mixtures enriched in one or more stereoisomer. The scope of the invention as described and claimed encompasses the racemic forms of the compounds as well as the individual enantiomers and non-racemic mixtures thereof.

As used herein, the term "group" may refer to a functional group of a chemical compound. Groups of the present compounds refer to an atom or a collection of atoms that are a part of the compound. Groups of the present invention may be attached to other atoms of the compound via one or more covalent bonds. Groups may also be characterized with respect to their valence state. The present invention includes groups characterized as monovalent, divalent, trivalent, etc. valence states.

As used herein, the term "precursor ion" is used herein to refer to an ion which is produced during ionization stage of mass spectrometry analysis, including the MS$^1$ ionization stage of MS/MS analysis.

As used herein, the terms "product ion" and "secondary ion" are used interchangeably in the present description and refer to an ion which is produced during ionization and/or fragmentation process(es) during mass spectrometry analysis. The term "secondary product ion" as used herein refers to an ion which is the product of successive fragmentations.

As used herein, the term "analyzing" refers to a process for determining a property of an analyte. Analyzing can determine, for example, physical properties of analytes, such as mass, mass to charge ratio, concentration, absolute abundance, relative abundance, or atomic or substituent composition. In the context of proteomic analysis, the term analyzing can refer to determining the composition (e.g., sequence) and/or abundance of a protein or peptide in a sample.

As used herein, the term "analyte" refers to a compound, mixture of compounds or other composition which is the subject of an analysis. Analytes include, but are not limited to, proteins, modified proteins, peptides, modified peptides, small molecules, pharmaceutical compounds, oligonucleotides, sugars, polymers, metabolites, lipids, and mixtures thereof.

As used herein, the term "mass spectrometry" (MS) refers to an analytical technique for the determination of the elemental composition, mass to charge ratio, absolute abundance and/or relative abundance of an analyte. Mass spectrometric techniques are useful for elucidating the composition and/or abundance of analytes, such as proteins, peptides and other chemical compounds. Mass spectrometry includes processes comprising ionizing analytes to generate charged species or species fragments, fragmentation of charged species or species fragments, such as product ions, and measurement of mass-to-charge ratios of charged species or species fragments, optionally including additional processes of isolation on the basis of mass to charge ratio, additional fragmentation processing, charge transfer processes, etc. Conducting a mass spectrometric analysis of an analyte results in the generation of mass spectrometry data for example, comprising the mass-to-charge ratios and corresponding intensity data for the analyte and/or analyte fragments. Mass spectrometry data corresponding to analyte ion and analyte ion fragments is commonly provided as intensities of as a function of mass-to-charge (m/z) units representing the mass-to-charge ratios of the analyte ions and/or analyte ion fragments. Mass spectrometry commonly allows intensities corresponding to difference analytes to be resolved in terms of different mass to charge ratios. In tandem mass spectrometry (MS/MS or MS$^2$), multiple sequences of mass spectrometry analysis are performed. For example, samples containing a mixture of proteins and peptides can be ionized and the resulting precursor ions separated according to their mass-to-charge ratio. Selected precursor ions can then be fragmented and further analyzed according to the mass-to-charge ratio of the fragments.

As used herein, the term "interference" refers to a species detected in an analysis which interferes with the detection of a species or analyte of interest. Interference can refer to detection of a protein, or protein fragment, which is not a protein or protein fragment of interest and which interferes with the accurate detection or quantitation of the protein or peptide fragment of interest. Interference can be quantified as an interference ratio, such as a ratio of an amount of interference signal to an amount of analyte signal. In a mass spectral analysis, interference can be manifested as an interference peak which corresponds to detection of a species which is not an analyte of interest.

As described herein, "isolation" or an "isolation window" refers to a range of ions, such as precursor ions that is selectively separated and fragmented, manipulated or isolated.

As used herein, the term "species" refers to a particular molecule, compound, ion, anion, atom, electron or proton. Species include isotopically labeled analytes, isotopic tagging reagents, isotopically labeled amino acids and/or isotopically labeled peptide or proteins.

As used herein, the term "mass-to-charge ratio" refers to the ratio of the mass of a species to the charge state of a species. The term "m/z unit" refers to a measure of the mass to charge ratio. The Thomson unit (abbreviated as Th) is an example of an m/z unit and is defined as the absolute value of the ratio of the mass of an ion (in Daltons) to the charge of the ion (with respect to the elemental charge).

As used herein, the term "mass spectrometer" refers to a device which generates ions from a sample, separates the ions according to mass to charge ratio, and detects ions, such as product ions derived from isotopically enriched compound, isotopic tagging reagents, isotopically labeled amino acids and/or isotopically labeled peptide or proteins. Mass spectrometers include single stage and multistage mass spectrometers. Multistage mass spectrometers include tandem mass spectrometers which fragment the mass-separated ions and separate the product ions by mass once.

The terms "peptide" and "polypeptide" are used synonymously in the present description, and refer to a class of compounds composed of amino acid residues chemically bonded together by amide bonds (or peptide bonds). Peptides and polypeptides are polymeric compounds comprising at least two amino acid residues or modified amino acid residues. Modifications can be naturally occurring or non-naturally occurring, such as modifications generated by chemical synthesis. Modifications to amino acids in peptides include, but are not limited to, phosphorylation, glycosylation, lipidation, prenylation, sulfonation, hydroxylation, acetylation, methylation, methionine oxidation, alkylation, acylation, carbamylation, iodination and the addition of cofactors. Peptides include proteins and further include compositions generated by degradation of proteins, for example by proteolytic digestion. Peptides and polypeptides can be generated by substantially complete digestion or by partial digestion of proteins. Polypeptides include, for example, polypeptides comprising 2 to 100 amino acid units, optionally for some embodiments 2 to 50 amino acid units and, optionally for some embodiments 2 to 20 amino acid units and, optionally for some embodiments 2 to 10 amino acid units.

"Protein" refers to a class of compounds comprising one or more polypeptide chains and/or modified polypeptide chains. Proteins can be modified by naturally occurring processes such as post-translational modifications or co-translational modifications. Exemplary post-translational modifications or co-translational modifications include, but are not limited to, phosphorylation, glycosylation, lipidation, prenylation, sulfonation, hydroxylation, acetylation, methylation, methionine oxidation, the addition of cofactors, proteolysis, and assembly of proteins into macromolecular complexes. Modification of proteins can also include non-naturally occurring derivatives, analogues and functional mimetics generated by chemical synthesis. Exemplary derivatives include chemical modifications such as alkylation, acylation, carbamylation, iodination or any modification that derivatizes the protein.

Quantitative analysis in chemistry is the determination of the absolute or relative abundance of one, several, or all particular substance(s) present in a sample. For biological samples, quantitative analysis performed via mass spectrometry can determine the relative abundances of peptides and proteins. The quantitation process typically involves isotopic labeling of protein and peptide analytes and analysis via mass spectrometry.

A sample can be fractionated according to physical properties such as mass, length, or affinity for another compound, among others using chromatographic techniques as are well known in the art. Fractionation can occur in a separation stage which acts to fractionate a sample of interest by one or more physical properties, as are well known in the art. Separation stages can employ, among other techniques, liquid and gas chromatographic techniques. Separation stages include, but are not limited to, liquid chromatography separation systems, gas chromatography separation systems, affinity chromatography separation systems, and capillary electrophoresis separation systems.

"Fragment" refers to a portion of molecule, such as a peptide. Fragments may be singly or multiply charged ions. Fragments may be derived from bond cleavage in a parent molecule, including site specific cleavage of polypeptide bonds in a parent peptide. Fragments may also be generated from multiple cleavage events or steps. Fragments may be a truncated peptide, either carboxy-terminal, amino-terminal or both, of a parent peptide. A fragment may refer to products generated upon the cleavage of a polypeptide bond, a C—C bond, a C—N bond, a C—O bond or combination of these processes. Fragments may refer to products formed by processes whereby one or more side chains of amino acids are removed, or a modification is removed, or any combination of these processes. Fragments useful in the present invention include fragments formed under metastable conditions or result from the introduction of energy to the precursor by a variety of methods including, but not limited to, collision induced dissociation (CID), surface induced dissociation (SID), laser induced dissociation (LID), electron capture dissociation (ECD), electron transfer dissociation (ETD), or any combination of these methods or any equivalents known in the art of tandem mass spectrometry. Fragments useful in the present invention also include, but are not limited to, x-type fragments, y-type fragments, z-type fragments, a-type fragments, b-type fragments, c-type fragments, internal ion (or internal cleavage ions), immonium ions or satellite ions. The types of fragments derived from a an analyte, such as a isotopically labeled analyte, isotopically labeled standard and/or isotopically labeled peptide or proteins, often depend on the sequence of the parent, method of fragmentation, charge state of the parent precursor ion, amount of energy introduced to the parent precursor ion and method of delivering energy into the parent precursor ion. Properties of fragments, such as molecular mass, may be characterized by analysis of a fragmentation mass spectrum.

An "amine reactive group", "carbonyl reactive group", or "thiol reactive group" of a tagging reagent can be any functional group able to react with an amine group, carbonyl group, and thiol group, respectively, of a peptide, protein or other molecule, thereby forming bond between the isotopically enriched compound or tag and the peptide, protein or other molecule.

An "amino acid" refers to an organic compound containing an amino group ($NH_2$), a carboxylic acid group (COOH), and any of various side chain groups. Amino acids may be characterized by the basic formula $NH_2CHRCOOH$ wherein R is the side chain group. Natural amino acids are those amino acids which are produced in nature, such as isoleucine, alanine, leucine, asparagine, lysine, aspartic acid, methionine, cysteine, phenylalanine, glutamic acid, threonine, glutamine, tryptophan, glycine, valine, proline, serine, tyrosine, arginine, and histidine as well as ornithine and selenocysteine.

As used herein, "isotopically enriched" and "isotopically labeled" refer to compounds (e.g., such as isotopically labeled amino acids, isotopically labeled standards, isotopically labeled analyte, isotopic tagging reagents, and/or isotopically labeled peptide or proteins) having one or more isotopic labels, such as one or more heavy stable isotopes. An "isotopic label" refers to one or more heavy stable isotopes introduced to a compound, such as isotopically labeled amino acids, isotopically labeled standards, isotopically labeled analyte, isotopic tagging reagents, and/or isotopically labeled peptide or proteins, such that the compound generates a signal when analyzed using mass spectrometry that can be distinguished from signals generated from other compounds, for example, a signal that can be distinguished from other isotopologues on the basis of mass-to-charge ratio. "Isotopically-heavy" refers to a compound or fragments/moieties thereof having one or more high mass, or heavy isotopes (e.g., stable heavy isotopes such as $^{13}C$, $^{15}N$, $^{2}H$, $^{17}O$, $^{18}O$, $^{33}S$, $^{34}S$, $^{37}Cl$, $^{81}Br$, $^{29}Si$, and $^{30}Si$.).

In an embodiment, an isotopically enriched composition comprises a compound of the invention having a specific isotopic composition, wherein the compound is present in an abundance that is at least 10 times greater, for some embodiments at least 100 times greater, for some embodiments at least 1,000 times greater, for some embodiments at least 10,000 times greater, than the abundance of the same compound having the same isotopic composition in a naturally occurring sample. In another embodiment, an isotopically enriched composition has a purity with respect to a compound of the invention having a specific isotopic composition that is substantially enriched, for example, a purity equal to or greater than 90%, in some embodiments equal to or greater than 95%, in some embodiments equal to or greater than 99%, in some embodiments equal to or greater than 99.9%, in some embodiments equal to or greater than 99.99%, and in some embodiments equal to or greater than 99.999%. In another embodiment, an isotopically enriched composition is a sample that has been purified with respect to a compound of the invention having a specific isotopic composition, for example using isotope purification methods known in the art.

"Mass spectrometer resolving power", often termed resolution, is a quantitative measure of how well m/z peaks in a mass spectrum are separated (i.e., resolved). There are a variety of conventions to calculate resolving power. The IUPAC definition is: Resolving power (R): $R=m/\Delta m$.

Overview

The field of mass spectrometry enabled proteomics continues to grow as the ease of and utility for protein and peptide identification increases. Several methods are currently used to incorporate a variety of tags, either chemically or metabolically, to impart mass differences that can be detected in mass spectra to differentiate samples and allow for quantitative comparisons of ion intensities. First, stable isotope labeling by amino acids in cell culture (SILAC) relies on the incorporation of normal or heavy amino acids into proteins during cell culture that results in two discrete peaks (due to the $^{13}C$ heavy atom) when analyzed via mass spectrometry. However, attempts to multiplex (compare multiple samples) is limited with this technique due to increased complexity in the resulting mass spectrum (a minimum of 3 Da separation between labeled peptides) that reduces the achievable proteomic coverage. Second, isobaric tagging, with reagents such as the commercially available iTRAQ or TMT, chemically adds a multicomponent tag to the peptide to be analyzed and provide quantification at the $MS^2$ level. However, isobaric labeling suffers from imprecision due to co-isolation of precursors, leading to reduced peptide identification and quantification.

A more recently developed method, mass defect tags or neutron mass tags, add a milliDa mass difference labeling tag to the sample for quantification at the $MS^1$ level. This strategy allows for multiplexing without the increased spectral complexity that accompanies traditional SILAC, and since quantification is done at the $MS^1$ level, it doesn't suffer from poor quantitative accuracy due to precursor co-isolation like isobaric labeling.

design, synthesis, and application of novel mass defect-based tags based on dimethyl pyrimidinyl ornithine (DiPyrO) and derivatives thereof enhance this strategy by providing tagging reagents that are not only compact in size but also enhance fragmentation of labeled peptides. The multiplexed DiPyrO mass defect tags are easy to synthesize in just a few steps using commercially available starting materials (see FIG. 8). No particularly dangerous reaction conditions or reagents are involved. In the examples described below, the DiPyrO$^6$ structure of the tag incorporates six heavy stable isotopes ($^{13}$C, $^2$H, $^{15}$N, $^{18}$O) in various configurations to impart a mass defect of 45.3 mDa between the lightest and heaviest tag to labeled peptides. Alternatively, a DiPyrO$^{10}$ tag incorporates ten heavy stable isotopes in various configuration to impart a mass defect of 54.5 mDa between the lightest and heaviest tag to labeled peptides. For example, up to 10-plex quantification is possible using DiPyrO$^{10}$ isotopologue variants that differ in mass by a minimum of 5.8 mDa.

The mass differences imparted by these tags on the peptide or protein analyte are small (such as 5.8-45.3 mDa for 8-plex quantification) allowing for analysis by high-resolution MS with relative quantification from a single LC-MS experiment. The small mass differences do not increase the complexity of the resulting spectrum, allowing for higher rates of target identification than other techniques.

Previously reported mass defect-based amine-reactive tags have several drawbacks including: a) the tags are very large in size (adding a mass of +435 Da per tag to labeled peptides), which negatively affects chromatographic behavior, ionization, and fragmentation of labeled peptides, especially when double-labeled; b) the tags introduce five additional amide bonds per label, the fragmentation of which generate several sequence-uninformative product ions; c) the tag may contain arginine, which, as the most basic amino acid, sequesters protons and inhibits sequence-informative peptide backbone fragmentation. Certain embodiments of the present invention addresses each of these problems directly: a) the mass defect-based DiPyrO tag is compact in size, adding a modest mass of 250-258 Da per tag to labeled peptides; b) only one additional amide bond is introduced, so sequence-uninformative fragment ions are kept to a minimum; c) the tag does not significantly negatively impact ionization, chromatographic retention/separation; and d) the tag is specifically designed to not sequester protons and to not hinder fragmentation—in fact, an increase in fragmentation efficiency of DiPyrO-labeled peptides has been observed, manifested by an overall increase in peptide cross-correlation (XCorr) scores following Sequest HT database search.

The performance of the DiPyrO tags has been evaluated using a non-isotopic version, and high labeling efficiency of yeast protein extract digests (>99% of all peptides) has been observed along with enhanced fragmentation at reduced normalized collision energies (NCE), and higher XCorr scores of labeled peptides following Sequest HT database search. The optimal NCE required for collision-induced dissociation (CID) and higher-energy collisional dissociation (HCD) fragmentation of DiPyrO-labeled peptides is reduced compared to normal peptides (27-30 vs 35). Combined with the increase in XCorr scores of identified peptides, a marked increase in fragmentation efficiency resulting from DiPyrO labeling has been observed. Additionally, the label enhances detection of smaller peptides (<8 amino acids).

Moreover, the synthetic approach used allows for the formulation of a number of isotopologue variants of the tag allowing for duplex, triplex, 4-plex, 5-plex, 6-plex, 8-plex, 9-plex, and 10-plex sets of the tag to overcome many of the challenges of multiplexing with previous tags and technologies.

EXAMPLES

Chemicals.

All isotopic reagents used for the synthesis of labels were purchased from Isotec (Miamisburg, Ohio). Mass spec grade trypsin/Lys C mix, yeast protein extract, dithiothreitol (DTT) were purchased from Promega (Madison, Wis.). Urea, ACS grade methanol (MeOH), ACS grade dichloromethane (DCM), ACS grade acetonitrile (ACN), Optima UPLC grade ACN, Optima UPLC grade water, and Optima LC/MS grade formic acid were purchased from Fisher Scientific (Pittsburgh, Pa.). Palladium on activated charcoal (Pd/C), hydrogen chloride gas (HCl), deuterium gas (D$_2$), L-arginine HCl, formaldehyde (CH$_2$O), Tris-HCl, triethylamine (TEA), acetylacetone, iodoacetamide (IAA), triethylammonium bicarbonate (TEAB), N,N-dimethylformamide (DMF), 4-(4, 6-dimethoxy-1, 3, 5-triazin-2-yl)-4-methylmorpholinium tetrafluoroborate (DMTMM), N-methylmorpholine (NMM), trifluoroacetic acid (TFA), and dimethyl-sulfoxide (DMSO) were purchased from Sigma-Aldrich (St. Louis, Mo.). Hydroxylamine solution was purchased from Alfa Aesar (Ward Hill, Mass.).

$^{18}$O Exchange.

The light DiPyrO tag ($^{15}$N$_4$$^{18}$O) requires $^{18}$O exchange prior to Pd/C-catalyzed dimethylation. L-Arginine HCl was dissolved in 12N HCl H$_2$$^{18}$O solution (pH 1) and stirred on a hot plate at 65° C. for 4 h. Excess HCl was evaporated from the solution in vacuo to obtain $^{18}$O L-arginine HCl.

N$^\alpha$,N$^\alpha$-dimethyl Arginine.

L-Arginine HCl, L-arginine-$^{15}$N$_4$ HCl, or L-arginine-(guanidineimino-$^{15}$N$_2$) HCl was dissolved in H$_2$O or D$_2$O, and formaldehyde (CH$_2$O, 37% w/w) or isotopic formaldehyde (CD$_2$O or $^{13}$CH$_2$O, 20% w/w) was added in 2.5× molar excess followed by addition of Pd/C. The reaction vessel was evacuated of air, filled with H$_2$ or D$_2$ gas, pressurized to 100 PSI, and stirred at 60° C. for 4 hr. The slurry was filtered and the N$^\alpha$,N$^\alpha$-dimethyl arginine product was dried in vacuo.

Derivatization of N$^\alpha$,N$^\alpha$-dimethyl Arginine.

N$^\alpha$,N$^\alpha$-dimethyl arginine was dissolved in a solution of 1:1:2:2 H$_2$O:TEA:EtOH:acetylacetone and the mixture was stirred on a hot plate at 60° C. for 16 hr. The N$_5$(4,6-dimethyl-2-pyrimidinyl)-N$^\alpha$,N$^\alpha$-dimethylornithine (DiPyrO) product was dried in vacuo, purified by flash column chromatography (MeOH/DCM), and dried in vacuo.

Activation of DiPyrO.

DiPyrO in anhydrous DMF was combined with DMTMM and NMM at 0.9× molar ratios to DiPyrO and vortexed at room temperature for 30 min. The mixture was used immediately for peptide labeling.

Yeast Protein Extract Enzymatic Digestion.

*Saccharomyces cerevisiae* protein extracts (Promega, Madison, Wis.) were digested by trypsin/Lys C mix (Promega), rLys-C (Promega), or Lys-N (Thermo Scientific Pierce, Rockford, Ill.). For the trypsin/Lys-C digestion, proteins were reduced in a solution of 5 mM DTT with 7 M urea in 80 mM ammonium bicarbonate pH 8 at 37° C. for 1 hr followed by alkylation of free thiols by addition of 15 mM IAA and incubation in the dark for 30 min. The alkylation reaction was quenched with 5 mM DTT, and the solution was diluted to 1 M urea with 50 mM Tris-HCl pH 8. Proteins were proteolytically digested by addition of trypsin/Lys C mix at a 1:25 enzyme to protein ratio and incubation at 37°

C. for 16 hr. Lys C and Lys N digests were performed similarly, with the following differences as instructed by the manufacturers' protocols: the urea concentration was not diluted prior to addition of Lys C or Lys N, and incubation of proteins with Lys C and Lys N was at 37° C. for 16 hr and 4 hr, respectively. Digestions were quenched with TFA to pH<3, and peptides were desalted using SepPak $C_{18}$ SPE cartridges (Waters, Milford, Mass.). Digested peptides were divided into equal aliquots in triplicate, dried in vacuo, and dissolved in 60:40 ACN:0.5M TEAB pH 8.5 prior to labeling.

Protein Digest Labeling.

Labeling was performed by addition of activated DiPyrO solution at a 19:1 or 25:1 or 50:1 label to peptide digest ratio by weight and vortexing at room temperature for 1 hr. The labeling reaction was quenched by addition of hydroxylamine to a concentration of 0.25%, and the labeled peptide samples were dried in vacuo. Labeled samples were combined, cleaned with SCX SpinTips (Protea Biosciences), and desalted with Omix C18 pipette tips (Agilent Technologies).

LC-$MS^2$—Peptide Samples.

Labeled peptide samples were analyzed by nanoLC-$MS^2$ using either a Waters nanoAcquity UPLC system (Milford, Mass.) coupled to a Thermo Scientific Orbitrap Elite mass spectrometer (San Jose, Calif.) or a Dionex Ultimate 3000 UPLC system coupled to a Thermo Scientific Orbitrap Fusion Lumos. Samples were dried in vacuo and dissolved in 3% ACN, 0.1% formic acid in water. Peptides were loaded onto a 75 μm inner diameter microcapillary column fabricated with an integrated emitter tip and packed with 15 cm of Bridged Ethylene Hybrid C18 particles (1.7 μm, 130 Å, Waters). Mobile phase A was composed of water and 0.1% formic acid. Mobile phase B was composed of ACN and 0.1% formic acid. Separation was performed using a gradient elution of 5% to 35% mobile phase B over 120 min at a flow rate of 300 nL/min. On the Orbitrap Elite, survey scans of peptide precursors from 380-1600 m/z were performed at a resolving power of 120 k or 240 k (@ 400 m/z) with an AGC target of $5\times10^5$ and maximum injection time of 150 ms. The top fifteen precursors were then selected for CID $MS^2$ analysis in the LTQ in rapid scan mode with an isolation width of 2.0 Da, a normalized collision energy (NCE) of 30, and an AGC target of $1\times10^4$, and maximum injection time of 100 ms. Precursors were subject to dynamic exclusion for 20 s with a ±0.05 m/z tolerance. On the Orbitrap Fusion Lumos, survey scans of peptide precursors from 350-1500 m/z were performed at a resolving power of 500 k (@ 200 m/z) with an AGC target of $1\times10^5$ and maximum injection time of 100 ms. The top fifteen precursors were then selected by quadrupole isolation for HCD $MS^2$ analysis in the LTQ in rapid scan mode with an isolation width of 0.7 Da, an NCE of 30, an AGC target of $1\times10^4$, and maximum injection time of 35 ms. Precursors were subject to dynamic exclusion for 20 s with a ±0.05 m/z tolerance.

Data Analysis—Peptide Samples.

Mass spectra were processed using either Proteome Discoverer (version 1.4.0.288, Thermo Scientific) for the non-isotopic DiPyrO experiments or MaxQuant (version 1.5.5.1) for the triplex DiPyrO experiments. Raw files were searched against the UniProt *Saccharomyces cerevisiae* complete database in Proteome Discover using the Sequest HT algorithm or in MaxQuant using the *Andromeda* algorithm. In Proteome Discoverer, searches were performed with a precursor mass tolerance of 25 ppm and a fragment mass tolerance of 0.6 Da. Static modifications consisted of non-isotopic DiPyrO labels on peptide N-termini (+248.16372 Da) and carbamidomethylation of cysteine residues (+57.02146 Da). Dynamic modifications consisted of non-isotopic DiPyrO labels on lysine (K) residues and oxidation of methionine residues (+248.16372 Da). Peptide spectral matches (PSMs) were validated based on q-values to 1% FDR using percolator. In MaxQuant, modifications for $DiPyrO_{0041}$ (+254.15610 Da), $DiPyrO_{2220}$ (+254.17705 Da), and $DiPyrO_{0600}$ (+254.20138 Da) were specified as N-term and K labels for standard quantification. First search peptide tolerance was set to 20 ppm and main search peptide tolerance was set to 4.5 ppm (Fusion Lumos) or 10 ppm (Elite). Static modification of carbamidomethylation of cysteine residues and variable modification of oxidation of methionine residues were chosen. The ITMS MS/MS match tolerance was set to 0.6 Da. Proteins and PSMs were filtered to 1% FDR. All other parameters remained at default. For quantification, a minimum ratio count of 1 was specified, and all peptides were used.

Filter-Aided N-Glycan Separation.

Glycoprotein (2 μg/μL dissolved in 50 mM TEAB buffer) was mixed with 4 μL 0.5M TCEP. The protein was heat denatured by alternating sample tube between 100° C. and room temperature water baths four times at 15 seconds each. The mixture was then added to a 30K MWCO filter and buffer exchanged with 200 μL 50 mM TEAB buffer (centrifuged at 14,000×g for 20 min at 20° C. three times) and incubated with PNGaseF (1 μL PNGaseF/10 μg protein) for 18 hours at 37° C. The released glycosylamines were separated from the de-glycosylated protein by centrifugation at 14,000×g for 20 minutes at 20° C. The resulting N-glycosylamines were then evaporated to dryness under vacuum and used for labeling immediately.

Glycan Labeling.

Labeling was performed by addition of activated DiPyrO solution to the dried glycans at a 25:1 label to original glycoprotein mass ratio (by weight) and vortexing at room temperature for 1 hr. The labeling reaction was quenched by addition of hydroxylamine to a concentration of 0.25%, the labeled glycan samples were combined, cleaned with an Oasis HLB cartridge (Waters), and dried in vacuo.

LC-$MS^2$—Glycan Samples.

Labeled glycan samples were analyzed by nanoHILIC-LC-$MS^2$ using a Dionex Ultimate 3000 UPLC system coupled to a Thermo Scientific Orbitrap Q-Exactive HF. Samples were dried in vacuo and dissolved in 80% ACN in water. Peptides were loaded onto a 75 μm inner diameter microcapillary column fabricated with an integrated emitter tip and packed with 30 cm of PolyGLYCOPLEX A particles (PolyLC). Mobile phase A was composed of ACN and 0.1% formic acid. Mobile phase B was composed of water and 0.1% formic acid. Separation was performed using a gradient elution of 25% to 45% mobile phase B over 40 min at a flow rate of 300 nL/min. On the Q-Exactive HF, survey scans of precursors from 300-2000 m/z were performed at a resolving power of 240 k (@ 200 m/z) with an AGC target of $1\times10^6$ and maximum injection time of 100 ms. The top five precursors were then selected for HCD $MS^2$ analysis with an isolation width of 2.0 Da and a normalized collision energy (NCE) of 27. Precursors were subject to dynamic exclusion for 10 s.

Rationale and Design Considerations of the DiPyrO Mass Defect Tags.

NeuCode SILAC has established mass defect-based isotopic labeling as a viable MS quantitative approach that possesses several advantages over traditional SILAC. However, the technique is still limited to metabolic incorporation. The application of SILAC to mammals (SILAM), such as transgenic mice for studies of physiology or disease, requires feeding of heavy-labeled diet for weeks or for multiple generations of animals prior to harvesting of tissues (Wu et al., Anal Chem, 2004, 76:4951-4959; McClatchy et al., J Proteome Res, 2007, 6:2005-2010; and Rauniyar et al., Methods, 2013, 61:260-268). The rate of incorporation into tissue occurs at differing rates for differing tissues, and incorporation is not complete. Integrating the NeuCode approach into SILAM requires that a diet of feed containing expensive mass defect-based lysine isotopologues be provided as the only protein source for weeks.

In contrast, a chemical labeling approach can conveniently impart mass defect signatures into any biological sample, regardless of origin, with high labeling efficiency. A chemical labeling approach can also be more cost-effective for mammalian samples, provided that the label is easily synthesized using readily available reagents, since labeling reagents are needed in smaller quantities in proportion to the amount of protein extract rather than the dietary needs of fostering the animals. Further, a chemical tag's structure is not limited to a single amino acid and can be custom designed to carry many more isotopes. Thus, translating the NeuCode strategy to a chemical reagent format would allow it to be applied to a wide variety of samples and increase multiplexing capacity. This logic inspired Herbert et al to develop amine-reactive NeuCode labels featuring mass defect-based isotopologues that differ in mass by 12.6 mDa (Hebert et al., Mol Cell Proteomics, 2013, 12:3360-3369). The tag is comprised of three amino acids—acetylarginine (AcArg), acetyllysine (AcLys), and glycine—and NHS ester amine-reactive group. A total of six heavy carbon and nitrogen isotopes are incorporated onto the AcArg and AcLys groups in four configurations to create a 4-plex set that spans 37.8 mDa. While these labels are suitable for demonstrating the concept, their synthesis is moderately complex and requires multiple protected isotopic amino acids, which are expensive, and the resulting tag is exceedingly bulky, adding a nominal mass of 431 Da per tag to labeled peptides.

Distinguishing between peptides at the $MS^1$ level that carry such mass defect signatures demands resolving powers accessible only to sophisticated Orbitrap and FT-ICR MS platforms. Hebert et al calculate that a resolving power of 240K is required to sufficiently resolve the 36 mDa difference between two particular NeuCode lysine isotopologues, $^{13}C_6{}^2H_0{}^{15}N_2$ and $^{13}C_0{}^2H_8{}^{15}N_0$, and allow quantification of >85% of tryptic peptides in a typical sample.[22] Quantifying ~95% of peptides spaced by 12.6 mDa or 6.3 mDa necessitates resolving powers of 480K and 960K, respectively; as such, the amine-reactive NeuCode labels were restricted to 12.6 mDa mass differences (Hebert et al., Mol Cell Proteomics, 2013, 12:3360-3369).

Mass defect-based multiplexing scales with resolution by allowing more isotopologue variants, and a 12-plex version of the amine-reactive NeuCode tags with isotopologues differing in mass by 6.3 mDa was reported (Hebert et al., "FTMS enabled neturon-encoded chemical tags: 4, 12, and 36 plexes" presentation, 2013, pp. 1-79). These tags carry twelve nitrogen atoms spread across five amino acids to achieve a mass difference of 69.5 mDa between the lightest ($^{13}C_0{}^{15}N_{11}$) and heaviest ($^{13}C_{11}{}^{15}N_0$) variant. Based on theoretical calculations, a resolving power of 960K should be sufficient for distinguishing between peptides with a 6.3 mDa mass defect, but an FT-ICR resolving power of 1.6M was required to overcome coalescence and sufficiently resolve all twelve peaks of a labeled yeast peptide with m/z ~814. The resolution requirement pushes the boundaries of what is currently possible with MS instrumentation, and the immense size of the tag (>650 Da) shows what great lengths are necessary for high levels of mass defect-based multiplexing at the $MS^1$ level. While the tags are certainly functional in narrowly focused, proof-of-principle experiments, they intend only to indicate the potential of mass defect-based quantification rather than serve as practical tools for actual quantitative proteomics experiments. A tag that stays within the reasonable bounds of a typical quantitative proteomics workflow is needed to bridge the gap between NeuCode SILAC and mass defect-based chemical labels and make the approach more accessible.

In terms of practical considerations necessary for chemical tag design, simplicity and accessible synthesis are critical. Several other criteria must also be met for a mass defect-based chemical tag. The structure should be compact and offer a high density of nitrogen atoms, to impart negative mass defects with $^{15}N$, while also providing a straightforward avenue for incorporation of $^{13}C$, $^2H$, and $^{18}O$ to impart positive mass defects. Incorporating these isotopes should also be inexpensive. As a starting point, an amino acid can be a good candidate because of the wide availability of isotopic amino acids as well as the benefit of retaining native fragmentation pathways. Arginine is the best option as it possesses four nitrogen atoms. N,N-dimethylation allows addition of up to six $^2H$ isotopes to impart a substantial combined mass defect of +37.662 mDa, and it also allows the researcher to tailor an isotopologue with two $^{13}C$ isotopes. $^{18}O$ exchange adds two isotopes but contributes a modest +4.245 mDa mass defect, which synergizes well with the four $^{15}N$ isotopes that impart a -11.860 mDa mass defect. These two simple synthetic steps enable the efficient use of six total isotopic positions and create a light tag and a heavy tag that differ in mass by 45.277 mDa. By using as many as ten isotopic positions, light and heavy tags that differ in mass by 54.50 mDa can be created. It should be noted that the use of $^2H$ isotopes is key to achieving a sufficient mass defect difference between the lightest and heaviest labels without requiring coupling several amino acids to increase the number of nitrogen atoms and that incorporating $^2H$ isotopes by formaldehyde dimethylation allows keeping the tag size compact and the synthesis simple and accessible. Deuterium atoms are often a cause for concern due to their effect of chromatographic retention time during reversed-phase liquid chromatography (RPLC), but research has indicated that placing $^2H$ atoms around the polar amine on the second carbon of an amino acid decreases their interaction with RPLC stationary phase and minimizes retention time shifts due to the deuterium effect (Zhang et al., Anal Chem, 2002, 74:3662-3669; and Greer et al., J Am Soc Mass Spectrom, 2015, 26:107-119).

Unfortunately, arginine is not particularly ideal as a chemical tag based on its polarity, basicity, and hydrophilicity. This character is a direct consequence of the side-chain guanidino group and affects other criteria that must be considered: label purification & activation, and chromatographic retention, ionization, & fragmentation of labeled peptides. The synthesized tag needs to be isolated easily and recovered at high yield, but unprotected amino acids, especially polar, hydrophilic ones like arginine, can make purification by traditional small molecule purification techniques (i.e. liquid-liquid extraction, recrystallization, precipitation, flash column chromatography) particularly challenging. The hydrophilicity of arginine would decrease overall hydrophobicity of labeled peptides and reduce their retention during C18 SPE cleanup and RPLC separation. While the basicity of arginine will facilitate ionization of labeled peptides, fragmentation will yield little sequence information since arginine sequesters protons and severely suppresses cleavage of the peptide backbone (Tang et al., Anal Chem, 1993, 65:2824-2834; Dikler et al., J Mass Spectrom, 1997, 32:1337-1349; and Sullivan et al., Int J Mass Spectrom, 2001, 210-211:665-676). Additionally, peptides with low charge states are more successfully sequenced than those with high charge states following CID/HCD fragmentation (Swaney et al., Nat Meth, 2008, 5:959-964); by labeling peptides with one or two basic arginine residues, their charge state would be increased by +1 or +2 and their fragmentation and sequence identification would be hindered. This long list of complications can be addressed by derivatizing the guanidino group to attenuate its basicity and increase hydrophobicity. Such strategies have been employed previously to improve the fragmentation and sequencing of arginine-containing peptides (Dikler et al., J Mass Spectrom, 1997, 32:1337-1349; Sullivan et al., Int J Mass Spectrom, 2001, 210-211:665-676; Morris et al., Biochemical and Biophysical Research Communications 1973, 51: 247-255; Kuyama et al., 2008, 22: 2063-2072; Foettinger et al., J Mass Spectrom, 2006, 41:623-632; Leitner et al., J Mass Spectrom, 2003, 38: 891-899; Lindner et al., Anal Chim Acta, 2005, 528: 165-173; Leitner et al., J Mass Spectrom, 2007, 42:950-959; Onofrejova et al., J Sep Sci, 2008, 31: 499-506; and Dongre et al., J Am Chem Soc, 1996, 118:8365-8374).

Specifically, several researchers have found it useful to convert the guanidinium to a pyrimidine by reaction with acetylacetone (Dikler et al., J Mass Spectrom, 1997, 32:1337-1349; Sullivan et al., Int J Mass Spectrom, 2001, 210-211:665-676; Morris et al., Biochemical and Biophysical Research Communications 1973, 51: 247-255; and Kuyama et al., 2008, 22: 2063-2072). By applying this particular strategy to the design of the present mass defect tag, the resulting dimethyl arginine derivative can actually increase chromatographic retention, improve electrospray ionization, and enhance tandem mass fragmentation of labeled peptides.

The general structure of DiPyrO mass defect tags in an embodiment described herein is composed of an $N_5$(4,6-dimethyl-2-pyrimidinyl)-$N^\alpha,N^\alpha$-dimethylornithine and an amine-reactive triazine ester group for selective modification of peptide N-termini and lysine side chains (FIG. 1A). In an embodiment, the dimethyl pyrimidinyl ornithine structure features a total of six heavy stable isotopes (DiPyrO$^6$) in varying configurations to yield unique mass defect-based isotopologues differing in mass by up to 45.28 mDa. Synthesis of this DiPyrO reagent (FIG. 8) is accomplished in just a few steps: dimethylation of arginine, derivatization of dimethyl arginine with acetylacetone, and activation to form the triazine ester. The unactivated DiPyrO tag is highly pure following synthesis (FIG. 9) and can be stored until needed, at which point activation with DMTMM is performed immediately prior to labeling. Each incorporated DiPyrO$^6$ tag adds a moderate mass of 254 Da to the labeled peptide. Using only commercially available isotopic starting materials, a 2-plex, 3-plex set, a 4-plex set, and a 6-plex set of DiPyrO$^6$ tags can be formulated with respective minimum mass defects of 45.28 mDa, 20.95 mDa, 12.64 mDa, and 8.31 mDa between tags (FIG. 1B-E). An 8-plex DiPyrO$^6$ set with a mass defect of 5.84 mDa (FIG. 1F) is also possible with two custom isotopic arginines. FIG. 15 illustrates 11 DiPyrO$^6$ isotopologues, including the isotopic positions for each isotopologue, which can make up various multiplex sets in an embodiment of the invention.

Additionally, the use of DiPyrO isotopologues with two or ten heavy isotopes, DiPyrO$^2$ and DiPyrO$^{10}$, further allows for the creation of additional multiplex sets of tags with nominal masses of 250 Da and 258 Da (FIG. 2A-B) that can be used in conjunction with the 254 Da tags in a hybrid mass difference/mass defect quantification approach to increase multiplexing with 4 Da mass difference-spaced clusters of mass defect-based channels. Isotopologues of the DiPyrO$^2$ variant can be configured into 2-plex, 3-plex, and 4-plex sets with respective minimum mass defects of 18.48 mDa, 8.31 mDa, and 5.84 mDa. Isotopologues of the DiPyrO$^{10}$ variant can be configured into 2-plex, 3-plex, 4-plex, 5-plex, 6-plex, 9-plex, and 10-plex with with respective minimum mass defects of 54.50 mDa, 26.79 mDa, 17.53 mDa, 12.64 mDa, 9.22 mDa, 5.28 mDa, and 5.84 mDa. In an embodiment, the isotopically enriched compound or compounds are characterized by a formula depicted in FIG. 15, FIG. 27 or FIG. 28.

Possible isotopic configurations and the relative mass defects between the different DiPyrO$^6$ isotopologues of the 2-plex, 3-plex, 4-plex, 6-plex, and 8-plex sets of FIGS. 1B-1F are further shown in FIG. 3. Similarly, FIG. 4 shows heavy isotope configurations and relative mass defect spacing of an isotopically labeled lysine (K) able to be used in NeuCode SILAC. Also shown in FIG. 4 is the resolving power needed to identify different amounts of a yeast proteome using the NeuCode-labeled lysine for the different mass defect spacing (see Merrill et al., Mol Cell Proteomics, 2014, 13:2503-2512). A library of approximately 8,000 unique DiPyrO-labeled yeast tryptic peptides identified by data-dependent LC-MS/MS was used to assess the Orbitrap resolving power necessary to resolve the multiplets of each multiplex set (FIG. 5). A peptide is considered resolvable, and thus quantifiable, if its m/z difference is larger than its width at 10% maximum peak height.

DiPyrO$^6$ quantification is achievable on Orbitrap MS platforms at respective resolving powers of 120-140 k for 2-plex (Orbitrap Fusion, Orbitrap Elite, Q-Exactive HF, Q-Exactive), 240 k for 3-plex (Orbitrap Fusion, Orbitrap Elite, and Q-Exactive HF), and ≥480 k for 4-plex and 6-plex (Orbitrap Elite and Orbitrap Fusion). Quantification with 4-plex DiPyrO$^2$, 8-plex DiPyrO$^6$, or 10-plex DiPyrO$^{10}$ tags would require a future Orbitrap platform or current FT-ICR platform with a resolving power approaching one million in order to quantify >95% of all peptides. Resolving power comparisons between DiPyrO$^6$ labeled yeast digests and NeuCode SILAC yeast tryptic and Lys-C digests are further shown in FIGS. 6 and 7. DiPyrO tags permit greater multiplexing than NeuCode SILAC at each resolving power increment.

The DiPyrO$^2$, DiPyrO$^6$, and DiPyrO$^{10}$ variants with two, six, and ten heavy isotopes may be combined in a hybrid mass difference/mass defect quantification strategy to increase multiplexing at a given resolving power. For example, combining 2-plex DiPyrO$^2$, 3-plex DiPyrO$^6$, and 4-plex DiPyrO$^{10}$ enables 9-plex quantification (FIG. 22) at RP 240 k, which is sufficient for resolving the 17.53-24.33 mDa mass defect between the tags in each of the clusters. Given an instrument capable of RP 960 k, the 4-plex DiPyrO$^2$, 8-plex DiPyrO$^6$, and 10-plex DiPyrO$^{10}$ sets may be combined to achieve 22-plex quantification. FIG. 27 and FIG. 28 illustrate 5 DiPyrO$^2$ isotopologues and 18 DiPyrO$^{10}$ isotopologues, respectively, including the isotopic positions for each isotopologue, which can make up various multiplex sets in an embodiment of the invention. With the exception of three of the 10-plex DiPyrO$^{10}$ isotopologues, the various DiPyrO$^2$ and DiPyrO$^{10}$ multiplex sets can be synthesized with commercially available isotopic starting materials.

Characterization and Application of the DiPyrO Reagent.

Prior to synthesis of the mass defect isotopologues, the DiPyrO reagent was characterized using a light version of the tag for labeling and LC-MS$^2$ analysis of labeled complex protein digest samples. To assess the optimal collision energy for DiPyrO-labeled peptides, a labeled yeast tryptic digest was analyzed via LC-MS$^2$ on the Orbitrap Elite at CID NCE values of 24, 27, 30, 33, 36, and 39. In another experiment, the HCD collision energy was assessed with a labeled BSA tryptic digest at the same NCE values. The resulting numbers of identified PSMs and median XCorr values were plotted as functions of NCE (FIGS. 10A-B). In general, DiPyrO labeled peptides require reduced collision energy for good fragmentation. While the difference in sample used between the two experiments does not allow fair comparison of CID and HCD, it is observed that an NCE value of 30 yields high numbers of high quality spectra and is suitable for both CID and HCD.

To optimize the reaction times for activation and labeling, a yeast tryptic digest was labeled and evaluated under a number of conditions based on the number of identified proteins & peptides and the number PSMs containing the DiPyrO label. Activation reactions were carried out for 30 min or 1 hr, and labeling was carried out for 30 min, 1 hr, 2 hr, and 4 hr. Following LC-MS$^2$ analysis on the Orbitrap Elite using a 120 min gradient for each sample (data not shown), it was determined that 30 min activation was sufficient, whereas 60 min activation yielded 11% fewer protein groups and 15% fewer peptides. The 30 min labeling was sufficient, being fairly on par with the 1 hr labeling, while the 2 hr and 4 hr labelings slightly reduced the number of protein and peptide identifications.

To assess labeling efficiency, yeast digests (trypsin, Lys C) were labeled for 1 hr (see generally FIG. 11) at a 25:1 or 50:1 label to peptide ratio and analyzed on the Orbitrap Elite with an MS$^1$ resolving power of 120K over a 120 min elution gradient with CID fragmentation. The data was searched with DiPyrO tags specified as dynamic or static modifications on N-term and K residues to evaluate labeling efficiency. The numbers of identified protein groups, peptides, and PSMs are summarized in Table 1 below.

taining lysine are labeled with two tags, and nearly 95% of Lys C peptides containing lysine are labeled with two tags.

By incorporating two DiPyrO tags onto each peptide, the measured mass defect signature between channels is doubled, and the resolution required for quantification is reduced. To ensure that all peptides in a sample can accommodate two tags, Lys C or Lys N can be used as the enzyme for digestion to produce proteolytic peptides with lysine on the C-terminal side or N-terminal side, respectively. Since the DiPyrO tag is moderate in size, the presence of two tags does not severely limit analysis of labeled peptides. While the average Lys C and Lys N peptide is longer than the average tryptic peptide, they also tend to carry higher charge states due to internal arginine. The data from the labeling efficiency experiment, summarized previously in Table 1, indicates that trypsin digestion provides a greater number of protein identifications than Lys C digestion, by about 25%, and greater numbers of peptide identifications as well. At a label to peptide ratio of 1:50, labeling with two tags occurred at a slightly lower rate for Lys C peptides (94.9%) than for tryptic peptides (98.8%), though the overall labeling (either N-term or K) efficiencies were equal (99.8%).

The identification rates of CID and HCD fragmentation modes were then compared. During data dependent acquisition on the Orbitrap Elite using HCD, any MS$^1$ scans acquired in the Orbitrap must be completed before subsequent HCD MS$^2$ scans can be acquired. However, the Orbitrap Elite is capable of parallel MS$^1$ acquisition in the Orbitrap (FT) and CID MS$^2$ acquisition in the ion trap (IT). In this configuration, the time-intensive, high resolution MS$^1$ transient (384 ms for 120K, 768 ms for 240 k, ~1.6 ms for 480 k), necessary for distinguishing mass defect signatures, is acquired in Orbitrap while the LTQ simultaneously performs CID MS$^2$ analysis of the top N precursors. This greatly reduces the impact of the high resolution MS$^1$ scan on the overall duty cycle and results in greater numbers of acquired spectra. Three analyses were performed: 120 k FT-MS$^1$ & HCD 15 k FT-MS$^2$; 120 k FT-MS$^1$ & CID rapid scan IT-MS$^2$; 240 k FT-MS$^1$ & CID rapid scan IT-MS$^2$. The numbers of identified protein groups, peptides, and PSMs, and acquired spectra are summarized in Table 2. At an MS$^1$

TABLE 1

DiPyrO-labeled yeast protein & peptide identification rates and labeling efficiency.

|  | Proteins | Peptides | PSMs | w/K | N&K mod | K mod | N mod | N or K |
|---|---|---|---|---|---|---|---|---|
| Trypsin 50:1, Dyn N&K | 978 | 3966 | 8327 | 6012 | 5939 | 5987 | 8261 | 8309 |
| % Efficiency |  |  |  |  | 98.8% | 99.6% | 99.2% | 99.8% |
| Trypsin 25:1, Dyn N&K | 1013 | 4289 | 11119 | 7925 | 4848 | 7332 | 8021 | 10505 |
| % Efficiency |  |  |  |  | 61.2% | 92.5% | 72.1% | 94.5% |
| Trypsin 50:1, Stat N&K | 1007 | 4135 | 8625 | 6136 | 6136 |  |  |  |
| % Efficiency |  |  |  |  | 100.0% |  |  |  |
| Trypsin 25:1, Stat N&K | 927 | 3642 | 7596 | 4763 | 4763 |  |  |  |
| % Efficiency |  |  |  |  | 100.0% |  |  |  |
| Lys C 50:1, Dyn N&K | 777 | 2307 | 5019 | 4881 | 4631 | 4851 | 4787 | 5007 |
| % Efficiency |  |  |  |  | 94.9% | 99.4% | 95.4% | 99.8% |
| Lys C 25:1, Dyn N&K | 799 | 3085 | 8779 | 8646 | 5067 | 8177 | 5503 | 8613 |
| % Efficiency |  |  |  |  | 58.6% | 94.6% | 62.7% | 98.1% |
| Lys C 50:1, Stat N&K | 793 | 2435 | 5090 | 4931 | 4931 |  |  |  |
| % Efficiency |  |  |  |  | 100.0% |  |  |  |
| Lys C 25:1, Stat N&K | 695 | 2359 | 5100 | 4991 | 4991 |  |  |  |
| % Efficiency |  |  |  |  | 100.0% |  |  |  |

When DiPyrO is specified as a dynamic mod on both N-term & K, overall labeling efficiency is excellent at a 50:1 label to peptide ratio, with over 99% of peptides carrying at least one DiPyrO tag. Nearly 99% of tryptic peptides conresolving power of 120 k, parallel CID IT-MS$^2$ acquisition collects nearly twice as many spectra as does HCD FT-MS$^2$ and results in 44% more protein groups, 35% more peptides, and 48% more PSMs. Doubling the MS$^1$ resolving power to 240 k reduces the number of collected spectra by 10% which results in 7% fewer protein groups, 5% fewer peptides, and 10% fewer PSMs.

TABLE 2

DiPyrO-labeled yeast protein & peptide identification rates - HCD vs. CID.

|  | Proteins | Peptides | PSMs | DiPyrO Mod | Spectra |
|---|---|---|---|---|---|
| 120k MS[1] & HCD | 637 | 2987 | 5861 | 5770 | 15527 |
| % w/ mod |  |  |  | 98.4% |  |
| 120k MS[1] & CID | 918 | 4036 | 8693 | 8570 | 30013 |
| % w/ mod |  |  |  | 98.6% |  |
| 240k MS[1] & CID | 851 | 3824 | 7810 | 7689 | 26969 |
| % w/ mod |  |  |  | 98.5% |  |

To evaluate the effect of DiPyrO labeling on peptide identification, nanoLC-MS$^2$ analyses of labeled and unlabeled yeast extract digest samples were compared using HCD fragmentation. Normalized collision energy values of 30 for the labeled sample and 35 for the unlabeled sample were specified while other acquisition parameters were equal. The peptide charge state, peptide length, and XCorr value distributions across identified PSMs were plotted as histograms to compare between samples (FIGS. 12A-C). It was observed that DiPyrO labeling leads to moderate charge state enhancement—labeled peptides are more evenly distributed between 2+ and 3+ charge states at 42% and 47%, respectively, while unlabeled peptides are largely 2+(77%), and 4+ charge state is likewise higher for labeled peptides (9%) than for unlabeled (2%). Labeling also enhances detection and identification of short peptides with 6-8 amino acids (21.6% labeled compared to 12.5% unlabeled). Interestingly, labeling enhances the overall quality of MS$^2$ spectra, as the distribution of XCorr values spreads considerably further towards higher values-31% of PSMs have an XCorr of 3.0 or greater in the labeled sample compared to 11% in the unlabeled sample, while 14% of labeled PSMs have an XCorr of 4.0 or greater compared to 1% of unlabeled PSMs. This increase in identification confidence indicates that the DiPyrO tag enhances the fragmentation of peptides into sequence-informative product ions. An example HCD MS$^2$ spectrum of a DiPyrO yeast tryptic peptide yielding high coverage of b- and y-ions is shown (FIG. 13). The labeled peptides produced a large number of b- and y-ion fragments allowing for more confident peptide sequence identification.

Fragmentation of DiPyrO-labeled peptides yields characteristic fragment ions in the low mass region of HCD MS$^2$ spectra which are analogous to isobaric tag reporter ions (FIG. 14A). The non-isotopic DiPyro tag gives rise to an intense ion at m/z 176.12 and lower intensity ions at m/z 204.11, 221.18, and 249.17. A multiplex set will give rise to several ions in four clusters due to the different isotopic configurations of each tag (FIG. 14B). While these ions could be used for MS$^2$-level quantification in the same manner as isobaric tag reporter ions, they will be subject to the same ratio distortion that arises due to precursor co-isolation. Since multiplex DiPyrO-labeled peptides produce several of these peaks, there is potential for the peaks to complicate peptide sequence identification using database search algorithms, especially if they share their mass with a peptide backbone fragment ion mass. It was recently reported that deconvoluting MS$^2$ spectra and removing reporter ions can increase confidence in identification of labeled peptides (Sheng et al., Mol Cell Proteomics, 2015, 14: 405-417). It would likely benefit identification of DyPyrO-labeled peptides to preprocess MS$^2$ spectra to remove these signature ions.

Application of the Duplex and Triplex DiPyrO$^6$ Tags for Labeling and Analysis of Complex Yeast Digest Samples.

Data was collected from the application of duplex and triplex DiPyrO$^6$ tags for labeling and analysis of complex yeast digest samples. A yeast tryptic digest sample was labeled in duplex with a light DiPyrO$_{0041}$ ($^{18}$O$^{15}$N$_4$) and heavy DiPyrO$_{0600}$ ($^2$H$_6$) tag, combined, and analyzed via nanoLC-MS$^2$ on an Orbitrap Elite system using a 120 minute elution gradient (FIG. 16). The base peak ion (BPI) chromatogram was obtained and an FT-MS scan was acquired in the Orbitrap mass analyzer at a resolving power (RP) of 120 k at retention time (RT)=66.4 minutes. The extracted ion chromatograms of a DiPyrO$^6$-labeled peptide detected with charge state 2+ and 3+ at m/z 642 and 963 are also shown along with the isotopic peak clusters with baseline-resolved peaks for the light- and heavy-labeled samples (FIG. 16). Extracted ion chromatograms of several DiPyrO$^6$-labeled peptides detected in the aforementioned sample are illustrated in FIG. 17 alongside the peptides' isotopic peak clusters, showing baseline-resolved peaks for the light- and heavy-labeled samples.

A yeast tryptic digest sample was labeled in triplex with light DiPyrO$_{0041}$ (18015N$_4$), medium DiPyrO$_{2220}$ ($^{13}$C$_2$$^2$H$_2$$^{15}$N$_2$) and heavy DiPyrO$_{0600}$ ($^2$H$_6$) tags, combined, and analyzed via LC-MS on an Orbitrap Elite system using a 120 minute elution gradient (FIG. 18). The BPI chromatogram was obtained and an FT-MS scan was acquired in the Orbitrap mass analyzer. The isotopic peak clusters of a peptide at m/z 777 detected in back-to-back FT-MS scans at RP 30 k and 240 k are also shown. The differentially labeled peptide samples are indistinguishable at RP 30 k, but are evident at 240 k, enabling quantification by comparison of the three peaks arising from the light, medium, and heavy DiPyrO-labeled samples. This peptide was detected with a 3+ charge state and was labeled with a single DiPyrO tag at the N-terminus. The triplex DiPyrO-labeled peptide peaks are baseline resolved at 240 k, but not at 120 k (FIG. 19).

FIG. 20 shows similar data from a yeast sample labeled in triplex with a light DiPyrO$_{0041}$ tag, medium DiPyrO$_{2220}$ tag and heavy DiPyrO$_{0600}$ tag in a 2:1:2 ratio, respectively, and analyzed via LC-MS on an Orbitrap Elite system. Isotopic peak clusters of peptides at m/z 471, 628 and 942 detected in back-to-back FT-MS scans at RP 30 k and 240 k are shown. The differentially labeled peptide samples are indistinguishable at RP 30 k, but are evident at 240 k, enabling quantification by comparison of the three peaks arising from the light, medium, and heavy DiPyrO$^6$-labeled samples. After processing with MaxQuant (version 1.5.5.1) software, approximately 76% of identified proteins and 64% of identified peptides were successfully quantified using the triplex DiPyrO$^6$ tags.

A comparison was performed between a tryptic peptide carrying a single DiPyrO tag with a tryptic peptide carrying two DiPyrO tags (FIG. 21). The tryptic peptide with an N-terminal amine and a C-terminal arginine (R) residue carried a single tag, while the peptide with an N-terminal amine and a C-terminal lysine (K) residue, with side-chain amine, carried two tags thereby doubling the imparted mass defect and was more readily baseline resolved at RP 240 k. Doubling the mass defect difference between channels can enable multiplexed analysis at lower resolving powers.

Application of the Duplex DiPyrO⁶ Tags for Labeling and Analysis of Metabolite Standards.

A sample containing a mixture of amine-containing metabolite standards—amino acids phenylalanine (165.0790 Da), tryptophan (204.0899 Da), and leucine/isoleucine (131.0946 Da)—was dissolved in in 0.5 M TEAB buffer and labeled in duplex with a light $DiPyrO_{0041}$ ($^{16}N_4{}^{18}O$; +254.1561) tag and a heavy $DiPyrO_{0600}$ ($^2H_6$; +254.20138) tag at a 25:1 ratio (by weight) of tag to metabolite standard for 1 hour. The labeled samples were combined at a 2:1 ratio and analyzed via nanoLC-MS² on an Orbitrap Elite system using a 30 minute elution gradient. FIG. 23 shows FT-MS scan spectra acquired in the Orbitrap mass analyzer at RP 120 k along with the extracted ion chromatograms of each DiPyrO-labeled amino acid detected with charge state 1+ at m/z 420, 459, and 386. The isotopic peak clusters show baseline-resolved peaks for the light- and heavy-labeled samples.

Application of the Duplex DiPyrO⁶ Tags for Labeling and Analysis of Glycans.

Ovalbumin glycoprotein standard was denatured and glycans were released with PNGaseF overnight. Released N-glycosylamines were separated from the deglycosylated protein by centrifugation at 14,000×g. To determine appropriate labeling conditions, the freshly released glycans were either dissolved in 05 M TEAB buffer or dried completely prior to addition of freshly activated nonisotopic DiPyrO tag (in dry DMF) at 25:1 or 50:1 ratio (by weight) of tag to original glycoprotein mass. Labeling of dried glycans resulted in efficient labeling in 1 hour. FIG. 24 shows the labeling efficiencies of the identified glycans for the 25:1 and 50:1 ratio samples following MALDI-MS analysis on a MALDI Orbitrap LTQ XL system and comparison of signal intensities of unlabeled and labeled glycan peaks. A 50:1 ratio provides nearly complete labeling for all but one high-mass N-glycosylamine. MALDI-MS spectra of abundant unlabeled and labeled glycans detected in the mass range of 1200-2000 m/z are shown in FIG. 25.

Freshly released glycan samples were then dried and labeled in duplex with a light $DiPyrO_{0041}$ ($^{15}N_4{}^{18}O$; +254.1561) tag and a heavy $DiPyrO_{0600}$ ($^2H_6$; +254.20138) tag, combined at a 1:1 ratio, and analyzed via nanoHILIC-LC-MS² on an Orbitrap Q-Exactive HF system using a 40 minute elution gradient. FIG. 26A shows an example FT-MS scan spectrum acquired in the Orbitrap mass analyzer at RP 240 k of a DiPyrO-labeled glycan doublet at m/z 858.9 along with the extracted ion chromatograms of the light- and heavy-labeled samples. The isotopic peak clusters show baseline-resolved peaks for the light- and heavy-labeled samples. FIG. 26B shows the annotated HCD FT-MS² spectrum of the doublet at m/z 858.9 containing a complete set of fragment ions for confident structural identification of the DiPyrO⁶-labeled glycan.

CONCLUSIONS

The synthetic reaction steps and conditions for the DiPyrO tags have been determined and several isobaric multiplex sets comprised of isotopologues carrying six heavy isotopes have been successfully synthesized. Complex yeast digest samples have been labeled and analyzed by nanoLC-MS² on the Orbitrap Elite to evaluate fragmentation of labeled peptides. Optimization of the label to peptide ratio for complete labeling of both N-termini and lysine side-chains to double the mass defect and reduce the resolution required for analysis has been performed for trypsin and Lys C digest samples. Quantification of tryptic peptide samples as well as double-labeled Lys C peptide samples was performed to compare resolving power requirements and proteomic coverage. The mass defect-based duplex and triplex DiPyrO⁶ sets have been used to demonstrate the performance of the tags for complex proteome quantification, amine-containing metabolite quantification, and N-glycosylamine quantification using high-resolution (RP 240 k) Orbitrap MS acquisition. The work accomplished thus far has yielded promising results and established the viability of the DiPyrO mass defect tags as a robust MS quantification approach.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

REFERENCES (1) Oda, Y.; Huang, K.; Cross, F. R.; Cowburn, D.; Chait, B. T. Accurate quantitation of protein expression and site-specific phosphorylation. Proceedings of the National Academy of Sciences 1999, 96, 6591-6596.
(2) Ong, S.-E.; Blagoev, B.; Kratchmarova, I.; Kristensen, D. B.; Steen, H.; Pandey, A.; Mann, M. Stable isotope labeling by amino acids in cell culture, SILAC, as a simple and accurate approach to expression proteomics. Mol Cell Proteomics 2002, 1, 376-386.
(3) Pan, S.; Gu, S.; Bradbury, E. M.; Chen, X. Single peptide-based protein identification in human proteome through MALDI-TOF MS coupled with amino acids coded mass tagging. Anal Chem 2003, 75, 1316-1324.
(4) Wu, C. C.; MacCoss, M. J.; Howell, K. E.; Matthews, D. E.; Yates, J. R. Metabolic Labeling of Mammalian Organisms with Stable Isotopes for Quantitative Proteomic Analysis. Anal Chem 2004, 76, 4951-4959.
(5) Gygi, S. P.; Rist, B.; Gerber, S. A.; Turecek, F.; Gelb, M. H.; Aebersold, R. Quantitative analysis of complex protein mixtures using isotope-coded affinity tags. Nat Biotechnol 1999, 17, 994-999.
(6) Thompson, A.; Schafer, J.; Kuhn, K.; Kienle, S.; Schwarz, J.; Schmidt, G.; Neumann, T.; Hamon, C. Tandem Mass Tags: A Novel Quantification Strategy for Comparative Analysis of Complex Protein Mixtures by MS/MS. Anal Chem 2003, 75, 1895-1904.
(7) Ross, P. L.; Huang, Y. N.; Marchese, J. N.; Williamson, B.; Parker, K.; Hattan, S.; Khainovski, N.; Pillai, S.; Dey, S.; Daniels, S.; Purkayastha, S.; Juhasz, P.; Martin, S.; Bartlet-Jones, M.; He, F.; Jacobson, A.; Pappin, D. J. Multiplexed protein quantitation in *Saccharomyces cerevisiae* using amine-reactive isobaric tagging reagents. Mol Cell Proteomics 2004, 3, 1154-1169.
(8) Hsu, J.-L.; Huang, S.-Y.; Chow, N.-H.; Chen, S.-H. Stable-isotope dimethyl labeling for quantitative proteomics. Anal Chem 2003, 75, 6843-6852.
(9) Boersema, P. J.; Raijmakers, R.; Lemeer, S.; Mohammed, S.; Heck, A. J. R. Multiplex peptide stable isotope dimethyl labeling for quantitative proteomics. Nat Protoc 2009, 4, 484-494.

(10) Molina, H.; Yang, Y.; Ruch, T.; Kim, J.-W.; Mortensen, P.; Otto, T.; Nalli, A.; Tang, Q.-Q.; Lane, M. D.; Chaerkady, R.; Pandey, A. Temporal profiling of the adipocyte proteome during differentiation using a five-plex SILAC based strategy. J Proteome Res 2009, 8, 48-58.

(11) Wu, Y.; Wang, F.; Liu, Z.; Qin, H.; Song, C.; Huang, J.; Bian, Y.; Wei, X.; Dong, J.; Zou, H. Five-plex isotope dimethyl labeling for quantitative proteomics. Chem. Commun. 2014, 50, 1708.

(12) Choe, L.; D'Ascenzo, M.; Relkin, N. R.; Pappin, D.; Ross, P.; Williamson, B.; Guertin, S.; Pribil, P.; Lee, K. H. 8-plex quantitation of changes in cerebrospinal fluid protein expression in subjects undergoing intravenous immunoglobulin treatment for Alzheimer's disease. Proteomics 2007, 7, 3651-3660.

(13) Dayon, L.; Hainard, A.; Licker, V.; Turck, N.; Kuhn, K.; Hochstrasser, D. F.; Burkhard, P. R.; Sanchez, J.-C. Relative Quantification of Proteins in Human Cerebrospinal Fluids by MS/MS Using 6-Plex Isobaric Tags. Anal Chem 2008, 80, 2921-2931.

(14) Xiang, F.; Ye, H.; Chen, R.; Fu, Q.; Li, L. N,N-dimethyl leucines as novel isobaric tandem mass tags for quantitative proteomics and peptidomics. Anal Chem 2010, 82, 2817-2825.

(15) Frost, D. C.; Greer, T.; Xiang, F.; Liang, Z.; Li, L. Development and characterization of novel 8-plex DiLeu isobaric labels for quantitative proteomics and peptidomics. Rapid Commun Mass Spectrom 2015, 29, 1115-1124.

(16) Ow, S. Y.; Salim, M.; Noirel, J.; Evans, C.; Rehman, I.; Wright, P. C. iTRAQ underestimation in simple and complex mixtures: "the good, the bad and the ugly". J Proteome Res 2009, 8, 5347-5355.

(17) Wenger, C. D.; Lee, M. V.; Hebert, A. S.; McAlister, G. C.; Phanstiel, D. H.; Westphall, M. S.; Coon, J. J. Gas-phase purification enables accurate, multiplexed proteome quantification with isobaric tagging. Nat Meth 2011, 8, 933-935.

(18) Vincent, C. E.; Rensvold, J. W.; Westphall, M. S.; Pagliarini, D. J.; Coon, J. J. Automated gas-phase purification for accurate, multiplexed quantification on a stand-alone ion-trap mass spectrometer. Anal Chem 2013, 85, 2079-2086.

(19) Ting, L.; Rad, R.; Gygi, S. P.; Haas, W. MS3 eliminates ratio distortion in isobaric multiplexed quantitative proteomics. Nat Meth 2011, 8, 937-940.

(20) McAlister, G. C.; Nusinow, D. P.; Jedrychowski, M. P.; Wühr, M.; Huttlin, E. L.; Erickson, B. K.; Rad, R.; Haas, W.; Gygi, S. P. MultiNotch MS3 Enables Accurate, Sensitive, and Multiplexed Detection of Differential Expression across Cancer Cell Line Proteomes. Anal Chem 2014, 86, 7150-7158.

(21) Zhou, Y.; Shan, Y.; Wu, Q.; Zhang, S.; Zhang, L.; Zhang, Y. Mass defect-based pseudo-isobaric dimethyl labeling for proteome quantification. Anal Chem 2013, 85, 10658-10663.

(22) Hebert, A. S.; Merrill, A. E.; Bailey, D. J.; Still, A. J.; Westphall, M. S.; Strieter, E. R.; Pagliarini, D. J.; Coon, J. J. Neutron-encoded mass signatures for multiplexed proteome quantification. Nat Meth 2013, 10, 332-334.

(23) Merrill, A. E.; Hebert, A. S.; Macgilvray, M. E.; Rose, C. M.; Bailey, D. J.; Bradley, J. C.; Wood, W. W.; Masri, El, M.; Westphall, M. S.; Gasch, A. P.; Coon, J. J. NeuCode labels for relative protein quantification. Mol Cell Proteomics 2014, 13, 2503-2512.

(24) Rose, C. M.; Merrill, A. E.; Bailey, D. J.; Hebert, A. S.; Westphall, M. S.; Coon, J. J. Neutron Encoded Labeling for Peptide Identification. Anal Chem 2013, 130502121401004.

(25) Richards, A. L.; Vincent, C. E.; Guthals, A.; Rose, C. M.; Westphall, M. S.; Bandeira, N.; Coon, J. J. Neutron-encoded signatures enable product ion annotation from tandem mass spectra. Mol Cell Proteomics 2013, 12, 3812-3823.

(26) Rhoads, T. W.; Rose, C. M.; Bailey, D. J.; Riley, N. M.; Molden, R. C.; Nestler, A. J.; Merrill, A. E.; Smith, L. M.; Hebert, A. S.; Westphall, M. S.; Pagliarini, D. J.; Garcia, B. A.; Coon, J. J. Neutron-Encoded Mass Signatures for Quantitative Top-Down Proteomics. Anal Chem 2014, 86, 2314-2319.

(27) Rose, C. M.; Baughman, J. M.; Rhoads, T. W.; Williams, C. E.; Merrill, A. E.; Stapleton, D. S.; Keller, M. P.; Hebert, A. S.; Westphall, M. S.; Attie, A. D.; Kirkpatrick, D. S.; Dey, A.; Coon, J. J. NeuCode Mouse: Multiplexed Proteomics Analysis Reveals Tissue Specific Effects of Deubiquitinase Deletion. In; Baltimore, Md., 2014; pp. 1-65.

(28) Ulbrich, A.; Merrill, A. E.; Hebert, A. S.; Westphall, M. S.; Keller, M. P.; Attie, A. D.; Coon, J. J. Neutron-encoded protein quantification by Peptide carbamylation. J Am Soc Mass Spectrom 2014, 25, 6-9.

(29) Ulbrich, A.; Bailey, D. J.; Westphall, M. S.; Coon, J. J. Organic acid quantitation by NeuCode methylamidation. Anal Chem 2014, 86, 4402-4408.

(30) Hebert, A. S.; Merrill, A. E.; Stefely, J. A.; Bailey, D. J.; Wenger, C. D.; Westphall, M. S.; Pagliarini, D. J.; Coon, J. J. Amine-reactive Neutron-encoded Labels for Highly Plexed Proteomic Quantitation. Mol Cell Proteomics 2013, 12, 3360-3369.

(31) Tang, X. J.; Thibault, P.; Boyd, R. K. Fragmentation reactions of multiply-protonated peptides and implications for sequencing by tandem mass spectrometry with low-energy collision-induced dissociation. 1993.

(32) Dikler, S.; Kelly, J. W.; Russell, D. H. Improving mass spectrometric sequencing of arginine-containing peptides by derivatization with acetylacetone. J Mass Spectrom 1997, 32, 1337-1349.

(33) McClatchy, D. B.; Dong, M.-Q.; Wu, C. C.; Venable, J. D.; Yates, J. R. 15N Metabolic Labeling of Mammalian Tissue with Slow Protein Turnover. J Proteome Res 2007, 6, 2005-2010.

(34) Rauniyar, N.; McClatchy, D. B.; Yates, J. R. Stable isotope labeling of mammals (SILAM) for in vivo quantitative proteomic analysis. Methods 2013, 61, 260-268.

(35) Hebert, A. S.; Merrill, A. E.; Rose, C. M.; Bailey, D. J.; Stefely, J. A.; Vincent, C. E.; He, H.; Young, N.; Pagliarini, D. J.; Canterbury, J.; Zabrouskov, V.; Senko, M.; Denisov, E.; Makarov, A.; Marshall, A. G.; Westphall, M. S.; Coon, J. J. FTMS enabled neturon-encoded chemical tags: 4, 12, and 36 plexes. In; 2013; pp. 1-79.

(36) Zhang, R.; Sioma, C. S.; Thompson, R. A.; Xiong, L.; Regnier, F. E. Controlling deuterium isotope effects in comparative proteomics. Anal Chem 2002, 74, 3662-3669.

(37) Greer, T.; Lietz, C. B.; Xiang, F.; Li, L. Novel isotopic N,N-dimethyl leucine (iDiLeu) reagents enable absolute quantification of peptides and proteins using a standard curve approach. J Am Soc Mass Spectrom 2015, 26, 107-119.

(38) Sullivan, A. G.; Brancia, F. L.; Tyldesley, R.; Bateman, R.; Sidhu, K.; Hubbard, S. J.; Oliver, S. G.; Gaskell, S. J. The exploitation of selective cleavage of singly proto-

(39) Swaney, D. L.; McAlister, G. C.; Coon, J. J. Decision tree-driven tandem mass spectrometry for shotgun proteomics. Nat Meth 2008, 5, 959-964.
(40) Morris, H. R.; Dickinson, R. J.; Williams, D. H. Studies towards the complete sequence determination of proteins by mass spectrometry: Derivatisation of methionine, cysteine and arginine containing peptides. Biochemical and Biophysical Research Communications 1973, 51, 247-255.
(41) Kuyama, H.; Sonomura, K.; Shima, K.; Nishimura, O.; Tsunasawa, S. An improved method for de novo sequencing of arginine-containing, Nalpha-tris(2,4,6-trimethoxyphenyl)phosphonium-acetylated peptides. Rapid Commun Mass Spectrom 2008, 22, 2063-2072.
(42) Foettinger, A.; Leitner, A.; Lindner, W. Derivatisation of arginine residues with malondialdehyde for the analysis of peptides and protein digests by LC-ESI-MS/MS. J Mass Spectrom 2006, 41, 623-632.
(43) Leitner, A.; Lindner, W. Probing of arginine residues in peptides and proteins using selective tagging and electrospray ionization mass spectrometry. J Mass Spectrom 2003, 38, 891-899.
(44) Lindner, W. Effects of an arginine-selective tagging procedure on the fragmentation. Anal Chim Acta 2005, 528, 165-173.
(45) Leitner, A.; Foettinger, A.; Lindner, W. Improving fragmentation of poorly fragmenting peptides and phosphopeptides during collision-induced dissociation by malondialdehyde modification of arginine residues. J Mass Spectrom 2007, 42, 950-959.
(46) Onofrejova, L.; Leitner, A.; Lindner, W. Malondialdehyde tagging improves the analysis of arginine oligomers and arginine-containing dendrimers by HPLC-MS. J. Sep. Sci. 2008, 31, 499-506.
(47) Dongre, A. R.; Jones, J. L.; Somogyi, A.; Wysocki, V. H. Influence of peptide composition, gas-phase basicity, and chemical modification on fragmentation efficiency: Evidence for the mobile proton model. J Am Chem Soc 1996, 118, 8365-8374.
(48) Sheng, Q.; Li, R.; Dai, J.; Li, Q.; Su, Z.; Guo, Y.; Li, C.; Shyr, Y.; Zeng, R. Preprocessing significantly improves the peptide/protein identification sensitivity of high-resolution isobarically labeled tandem mass spectrometry data. Mol Cell Proteomics 2015, 14, 405-417.

We claim:
1. A composition comprising a compound having the following formula:

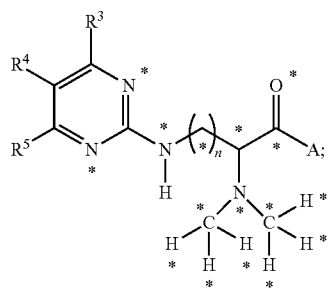

wherein A is:
—OH or

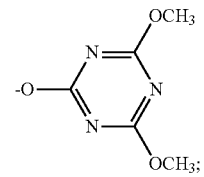

wherein each of $R^3$-$R^5$ is independently a hydrogen, a $C_1$-$C_4$ alkyl, or an acetyl group, or
wherein $R^3$ and $R^4$ or $R^4$ and $R^5$ combine to form a 5 or 6 membered aromatic or alicyclic ring;
wherein n is an integer selected from the range of 1 to 5;
provided that at least two atoms of the formula are heavy isotopes that are present in an amount in excess of the natural isotopic abundance; and
wherein said at least two atoms are selected from atoms designated by the *symbol of the formula.

2. The composition of claim 1, wherein said compound is characterized by the formula having:
at least two $^{13}O$ isotopes; or
at least one $^{13}O$ isotope and at least one $^{15}N$ isotope; or
at least one $^{13}O$ isotope and at least one $^{2}H$ isotope; or
at least one $^{13}O$ isotope and at least one $^{18}O$ isotope; or
at least two $^{15}N$ isotopes; or
at least one $^{15}N$ isotope and at least one $^{2}H$ isotope; or
at least one $^{15}N$ isotope and at least one $^{18}O$ isotope; or
at least two $^{2}H$ isotopes; or
at least one $^{2}H$ isotope and at least one $^{18}O$ isotope; or
at least one $^{13}O$ isotope, at least one $^{15}N$ isotope and at least one $^{2}H$ isotope; or
at least one $^{13}O$ isotope, at least one $^{15}N$ isotope and at least one $^{18}O$ isotope.

3. The composition of claim 1, wherein said compound is characterized by the formula:

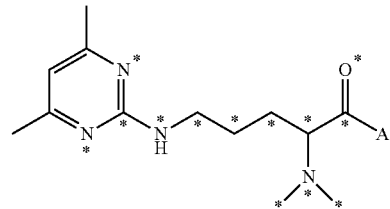

wherein said at least two atoms that are heavy isotopes are selected from atoms designated by the *symbol.

4. The composition of claim 1, wherein said compound is characterized by formula (FX7), (FX8), (FX9), (FX10), (FX11), (FX12), (FX13), (FX14), (FX15), (FX16), or (FX17):

(FX7)

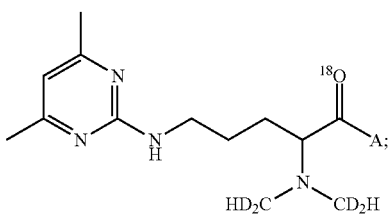

(FX8) 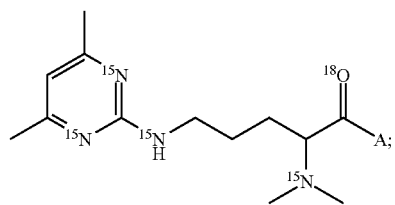

(FX9) 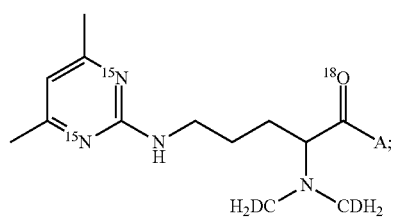

(FX10) 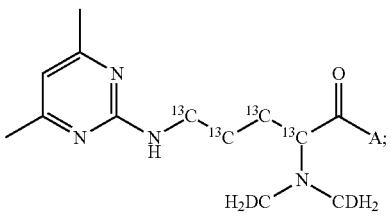

(FX11) 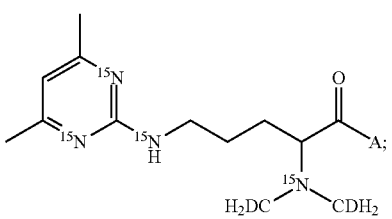

(FX12) 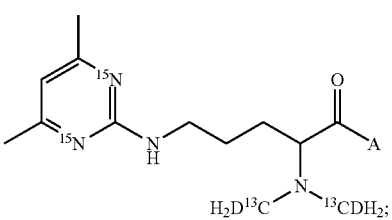

(FX13) 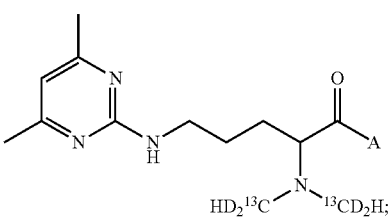

(FX14) 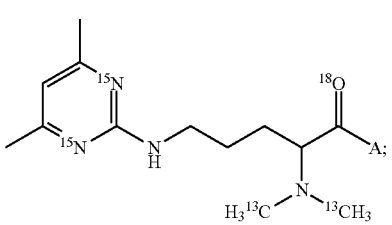

(FX15) 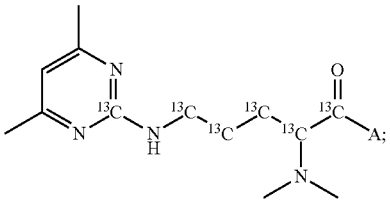

(FX16) 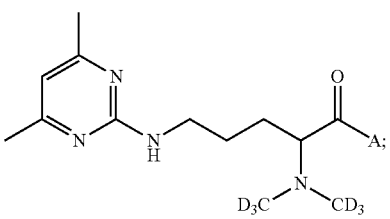

(FX17) 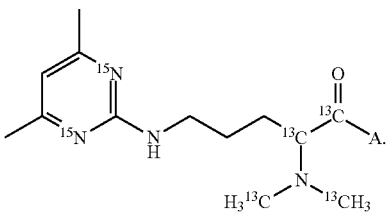

5. A kit comprising a plurality of different isotopologues each of said plurality of different isotopologues independently having the formula:

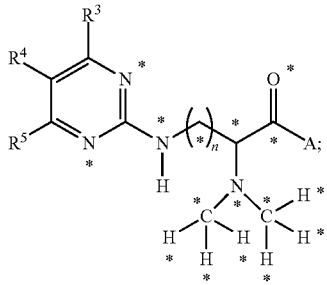

wherein A is:
—OH or

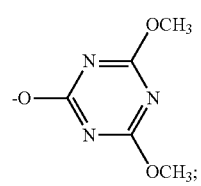

wherein each of $R^3$-$R^5$ is independently a hydrogen, a $C_1$-$C_4$ alkyl, or an acetyl group, or
wherein $R^3$ and $R^4$ or $R^4$ and $R^5$ combine to form a 5 or 6 membered aromatic or alicyclic ring;
wherein n is an integer selected from the range of 1 to 5;
provided that at least two atoms of the formula are heavy isotopes that are present in an amount in excess of the natural isotopic abundance;
wherein said at least two atoms are selected from atoms designated by the *symbol of the formula; and wherein two or more of said different isotopologues are characterized by a mass difference from one another that is less than or equal to 55 mDa.

6. The kit of claim 5, comprising 4 or more of said different isotopologues.

7. The kit of claim 5, wherein two or more of said different isotopologues are characterized by a mass difference from one another that is less than or equal to 25 mDa.

8. The kit of claim 5, wherein said different isotopologues are reactive with an amine group of a peptide, a protein, a glycan, or a metabolite.

9. A method of labeling target molecules containing one or more amine groups, said method comprising:
a) providing said target molecules; and
b) reacting said target molecules with one or more compounds, thereby generating isotopically labeled target molecules; wherein each of said one or more compounds independently has the formula:

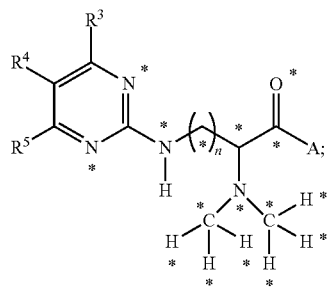

wherein A is:

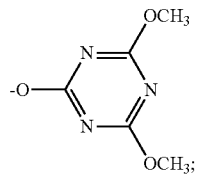

wherein each of $R^3$-$R^5$ is independently a hydrogen, a $C_1$-$C_4$ alkyl, or an acetyl group, or
wherein $R^3$ and $R^4$ or $R^4$ and $R^5$ combine to form a 5 or 6 membered aromatic or alicyclic ring;
wherein n is an integer selected from the range of 1 to 5;
provided that at least two atoms of the formula are heavy isotopes that are present in an amount in excess of the natural isotopic abundance, and wherein said at least two atoms are selected from atoms designated by the *symbol of the formula.

10. A method of analyzing target molecules using a mass spectrometry technique, said method comprising:
a) providing said target molecules in a plurality of different samples; and
b) providing a plurality of isotopologues and reacting said target molecules in each of said different samples with an isotopologue that is different than isotopologues reacted with other samples of the plurality of different samples, thereby generating samples comprising isotopically labeled target molecules, wherein each of the plurality of isotopologues independently has the formula:

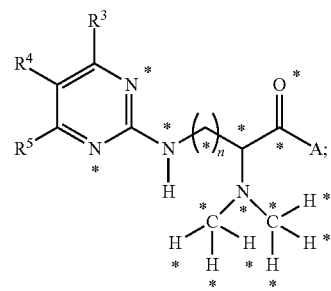

wherein A is:

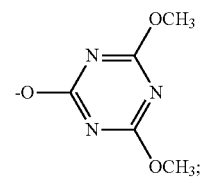

wherein each of $R^3$-$R^5$ is independently a hydrogen, a $C_1$-$C_4$ alkyl, or an acetyl group, or
wherein $R^3$ and $R^4$ or $R^4$ and $R^5$ combine to form a 5 or 6 membered aromatic or alicyclic ring;
wherein n is an integer selected from the range of 1 to 5;
provided that at least two atoms of the formula are heavy isotopes that are present in an amount in excess of the natural isotopic abundance, and wherein said at least two atoms are selected from atoms designated by the *symbol of the formula; and wherein two or more isotopologues of said plurality of isotopically enriched isotopologues are characterized by a mass difference from one another that is less than or equal to 55 mDa; and
c) analyzing said isotopically labeled target molecules for each sample using said mass spectrometry technique.

11. The method of claim 10, comprising reacting 4 or more different samples with different isotopologues.

12. The method of claim 10, wherein two or more isotopologues of said plurality of isotopologues are characterized by a mass difference from one another that is less than or equal to 25 mDa.

13. The method of claim 10, wherein each isotopologue of said plurality of isotopologues is independently characterized by formula:

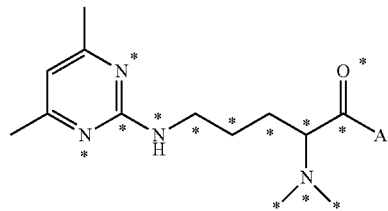

wherein said at least two atoms that are heavy isotopes are selected from atoms designated by the *symbol.

14. The method of claim 10, wherein at least five atoms of the formula are, independently from one another, selected from a carbon atom, a nitrogen atom, an oxygen atom and a hydrogen atom that is respectively a heavy isotope.

15. The method of claim 10, wherein said plurality of isotopologues are independently characterized by the formula having:
at least two $^{13}O$ isotopes; or
at least one $^{13}O$ isotope and at least one $^{15}N$ isotope; or
at least one $^{13}O$ isotope and at least one $^{2}H$ isotope; or
at least one $^{13}O$ isotope and at least one $^{18}O$ isotope; or
at least two $^{15}N$ isotopes; or
at least one $^{15}N$ isotope and at least one $^{2}H$ isotope; or
at least one $^{15}N$ isotope and at least one $^{18}O$ isotope; or
at least two $^{2}H$ isotopes; or
at least one $^{2}H$ isotope and at least one $^{18}O$ isotope; or
at least one $^{13}O$ isotope, at least one $^{15}N$ isotope and at least one $^{2}H$ isotope; or
at least one $^{13}O$ isotope, at least one $^{15}N$ isotope and at least one $^{18}O$ isotope.

16. The method of claim 10 further comprising a step of quantifying the relative amounts of the isotopically labeled target molecules in said samples.

17. A method of making a labeling reagent, comprising the steps of:
providing an amino acid precursor;
chemically reacting said amino acid precursor with a first reagent so as to provide an optionally substituted pyrimidine group; and
chemically reacting a carboxylic acid group of said amino acid precursor with a second reagent to form said labeling reagent having the formula:

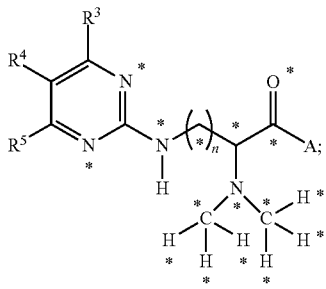

wherein A is:

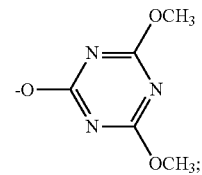

wherein each of $R^3$-$R^5$ is independently a hydrogen, a $C_1$-$C_4$ alkyl, or an acetyl group, or wherein $R^3$ and $R^4$ or $R^4$ and $R^5$ combine to form a 5 or 6 membered aromatic or alicyclic ring;

wherein n is an integer selected from the range of 1 to 5;

provided that at least two atoms of the formula are heavy isotopes that are present in an amount in excess of the natural isotopic abundance; and wherein said at least two atoms are selected from atoms designated by the *symbol of the formula.

18. The method of claim 17, wherein said amino acid precursor contains at least two atoms that are heavy isotopes, wherein said heavy isotopes are present in an amount in excess of the natural isotopic abundance.

19. The method of claim 17 further comprising a step of performing palladium-catalyzed dimethylation with formaldehyde on said amino acid precursor prior to forming the optionally substituted pyrimidine group.

20. The method of claim 19, wherein said amino acid precursor is isotopically enriched arginine.

21. The method of claim 20 comprising a step of derivatizing the guanidine group of the isotopically enriched arginine to form the optionally substituted pyrimidine group.

* * * * *